(12) United States Patent
Bierlmaier et al.

(10) Patent No.: US 8,513,272 B2
(45) Date of Patent: Aug. 20, 2013

(54) FORMS OF A FUSED PYRROLOCARBAZOLE COMPOUND

(75) Inventors: Stephen Bierlmaier, Thorndale, PA (US); Laurent Courvoisier, Thorndale, PA (US); Veronique Courvoisier, legal representative, Thorndale, PA (US); Raymond Scott Field, West Chester, PA (US); R. Curtis Haltiwanger, West Chester, PA (US); Martin J. Jacobs, West Chester, PA (US); Robert E. McKean, Chester Springs, PA (US); Mehran Yazdanian, Philadelphia, PA (US)

(73) Assignee: Cephalon, Inc., Frazer, PA (US)

( * ) Notice: Subject to any disclaimer, the term of this patent is extended or adjusted under 35 U.S.C. 154(b) by 49 days.

(21) Appl. No.: 13/105,457

(22) Filed: May 11, 2011

(65) Prior Publication Data

US 2011/0230508 A1  Sep. 22, 2011

Related U.S. Application Data

(63) Continuation of application No. PCT/US2009/065099, filed on Nov. 19, 2009.

(60) Provisional application No. 61/116,134, filed on Nov. 19, 2008.

(51) Int. Cl.
*A61K 31/505* (2006.01)
*C07D 401/14* (2006.01)

(52) U.S. Cl.
USPC .......................................... 514/275; 544/331

(58) Field of Classification Search
USPC .......................................... 514/275; 544/331
See application file for complete search history.

(56) References Cited

U.S. PATENT DOCUMENTS

| | | | |
|---|---|---|---|
| 5,475,110 A | 12/1995 | Hudkins et al. | 546/256 |
| 5,591,855 A | 1/1997 | Hudkins et al. | 546/256 |
| 5,594,009 A | 1/1997 | Hudkins et al. | 514/338 |
| 5,616,724 A | 4/1997 | Hudkins et al. | 548/417 |
| 5,705,511 A | 1/1998 | Hudkins et al. | 514/338 |
| 6,630,500 B2 | 10/2003 | Gingrich et al. | 514/410 |
| 7,109,229 B2 | 9/2006 | Engler et al. | 514/410 |
| 7,169,802 B2 | 1/2007 | Hudkins et al. | 514/410 |
| 7,241,779 B2 | 7/2007 | Hudkins et al. | 514/338 |
| 7,671,064 B2 * | 3/2010 | Hudkins et al. | 514/275 |
| 8,044,064 B2 * | 10/2011 | Becknell et al. | 514/275 |
| 2008/0125377 A1 | 5/2008 | Bartels et al. | 514/23 |
| 2011/0224436 A1 | 9/2011 | Prat-Lacondemine | 544/331 |

FOREIGN PATENT DOCUMENTS

| | | |
|---|---|---|
| EP | 0 545 195 B1 | 11/1995 |
| WO | WO 96/11933 A1 | 4/1996 |
| WO | WO 98/07433 A1 | 2/1998 |
| WO | WO 00/47583 A1 | 8/2000 |
| WO | WO 01/14380 | 3/2001 |
| WO | WO 02/17914 A2 | 3/2002 |
| WO | WO 02/28861 A2 | 4/2002 |
| WO | WO 02/28874 A3 | 4/2002 |
| WO | WO 02/30942 A3 | 4/2002 |
| WO | WO 02/092065 A2 | 11/2002 |
| WO | WO 2005/063763 | 7/2005 |
| WO | WO 2011/146488 | 11/2011 |

OTHER PUBLICATIONS

Brittain et al., Polymorphism in Pharmaceutical Solids, vol. 95; Drugs and Pharmaceutical Sciences. 1999, pp. 1-17.*
Hudkins, R.L., "Synthesis of indeno[2,1-*a*]pyrrolo[3,4-*c*]carbzole lactam regioisomers using ethyl cis-β-cyanoacrylate as a dienophile and lactam precursor," *J. Heterocyclic Chemistry*, 2003, 40, 135-142.
*J. Chem. Res.*, 1986, 1401-1445.
Lehninger, A.L., "The amino acid building blocks of proteins," The Molecular Basis of Cell Structure and Function, *Biochemistry*, 2$^{nd}$ Ed. Worth Publishers, NY, 1975, 71-77.
Peet, N., et al., "Synthesis of angular benzodipyrazoles and related systems," *Heterocycles*, 1991, 32(1), 41-72.
Wynne, J.H., et al., "Facile one-pot synthesis of S-alkyl thiocarbamates," *J. Org. Chem.*, 2003, 68, 3733-3735.
Angeles, et al., "Enzyme-linked immunosorbent assay for trkA tyrosine kinase activity," *Anal. Biochem.*, 1996, 236, 49-55.
Dermer, *Bio/Technology*, 1994, 12, 320.
Engler, T.A., et al., "Novel, potent and selective cynclin D1/CDK4 inhibitors: indolo[6,7-*a*]pyrrolo[3,4-*c*]carbazoles," *Bioorganic & Medicinal Chem. Letts.*, 2003, 13, 2261-2267.
Freshney, R.I., Culture of Animal Cells—a Manual of Basic Technique, Alan R. Liss, Inc., 1983, p. 4.
Gingrich, D.E., et al., "A new class of potent vascular endothelial growth factor receptor tyrosine kinase inhibitors: structure-activity relationships for a series of 9-alkoxymethyl-12-(3-hydroxypropyl)indeno[2,1-*a*]pyrrolo[3,4-*c*]carbazole-5-ones and the identification of CEP-5214 and its dimethylglycine ester prodrug clinical candidate CEP-7055," *J. Med. Chem.*, 2003, 46, 5375-5388.
Hudkins, R.L., et al., "Synthesis of benzo[*b*]furano-[2,3-*a*]pyrrolo[3,4-*c*]carbazole-5, -7-dione," *J. Heterocyclic Chemistry*, 2001, 38, 591-595.
Laird, A.D., et al., "Small molecule tyrosine kinase inhibitors: clinical development of anticancer agents," *Expert. Opin. Investig. Drugs*, 2003, 12(1), 51-64.
Merritt, S.E., et al., "The mixed lineage kinase DLK utilizes MKK7 and not MKK4 as substrate," *J. of Biol. Chem.*, 1999, 274(15), 10195-10202.
Pitt, A.M., et al., "High throughput screening protein kinase assays optimized for reaction, binding, and detection totally within a 96-well plate," *J. of Biomol. Screening*, 1996, 1(1), 47-51.
Rotin, et al., "SH2 domains prevent tyrosine dephosphorylation of the EGF receptor: identification of Tyr992 as the high-affinity biding site for SH2 domains of phospholipase C-γ," *EMBO J.*, 1992, 11(2), 559-567.

(Continued)

*Primary Examiner* — James O. Wilson
*Assistant Examiner* — Ebenezer O Sackey

(57) ABSTRACT

Alternative chemical and/or solid state forms of Compound I, processes to reproducibly make them and methods of treating patients using them.

25 Claims, 55 Drawing Sheets

(56) References Cited

OTHER PUBLICATIONS

Rovin, L.J., "Preformulation," *Remington's Pharmaceutical Sciences*, 17th Ed., Mack Publishing Co., Easton, PA, 1985, Chapter 76, 1409-1423.

Ruggeri, B., et al., "CEP-7055: A novel, orally active pan inhibitor of vascular endothelial growth factor receptor tyrosine kinases with potent antiangiogenic activity and antitumor efficacy in preclinical models," *Cancer Res.*, 2003, 63, 5978-5991.

Sanchez-Martinez, C., et al., "Aryl[a]pyrrolo[3,4-c]carbazoles as selective cyclin D1-CDK4 inhibitors," *Bioorganic & Medicinal Chem. Letts.*, 2003, 13, 3835-3839.

Schenone, P., et al., "Reaction of 2-dimethylaminomethylene-1,3-diones with dinucleophiles. I. Synthesis of 1,5-disubstituted 4-acylpyrazoles," *J. Heterocyclic Chem.*, 1982, 19, 1355-1361.

Becknell et al., *Bioorganic & Med. Chem. Lett.*, 2006, 16, 5368-5372.

Underiner et al., *Bioorganic & Med. Chem. Lett.*, 2008, 18, 2368-2372.

Dandu et al., *Bioorganic & Med. Chem. Lett.*, 2008, 18, 1916-1921.

* cited by examiner

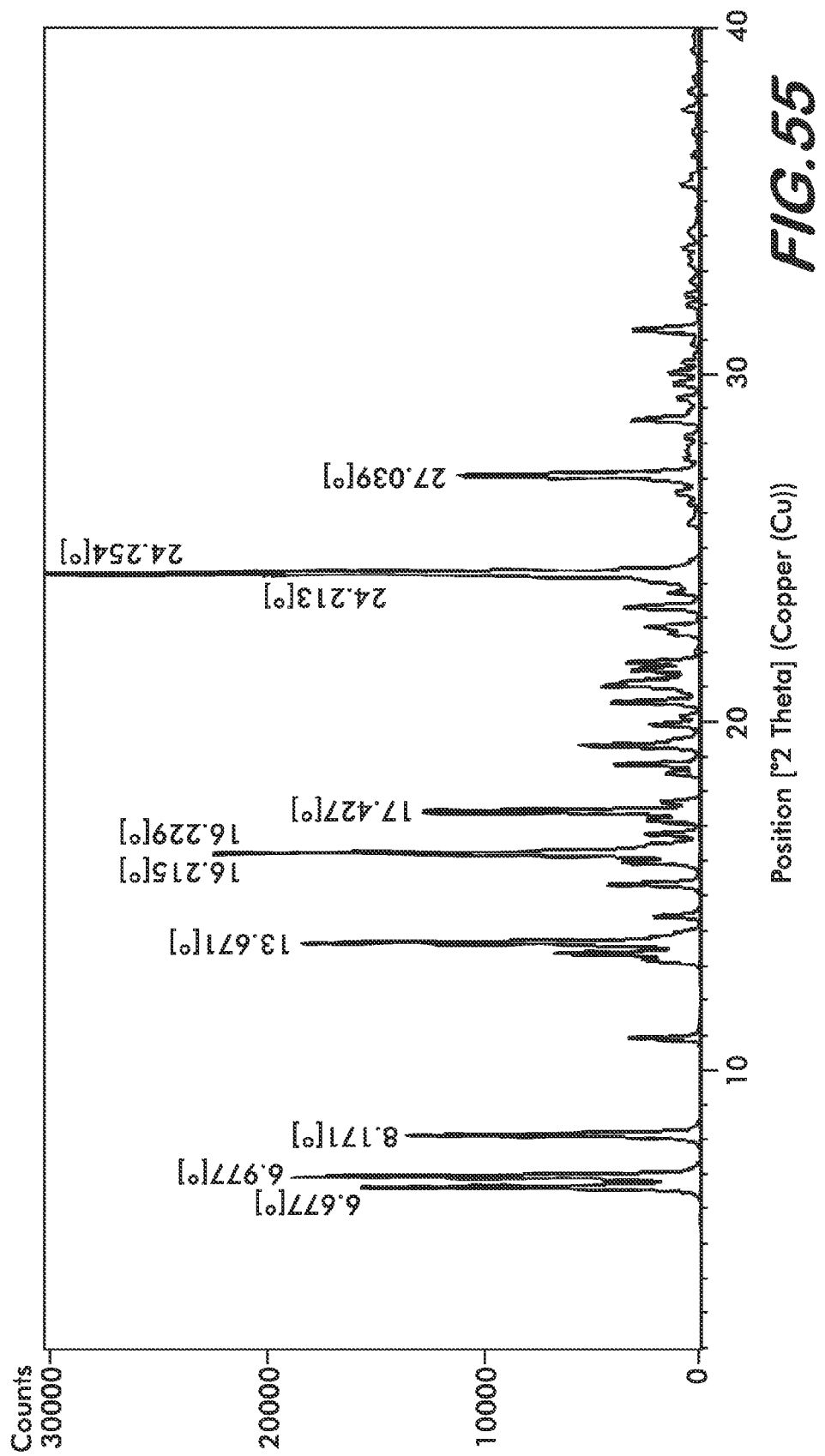

FORMS OF A FUSED PYRROLOCARBAZOLE COMPOUND

CROSS REFERENCE TO RELATED APPLICATIONS

This application is a continuation application of International Application No. PCT/US2009/065099, filed Nov. 19, 2009, which claims priority to U.S. Provisional Application Ser. No. 61/116,134, filed Nov. 19, 2008. The disclosures of the aforementioned applications are incorporated herein by reference in their entireties for all purposes.

FIELD OF THE INVENTION

The present invention relates to compositions which contain the novel fused pyrrolocarbazole compound Compound I, pharmaceutical compositions comprising Compound I, processes to reproducibly make them and methods of treating patients using them.

BACKGROUND OF THE INVENTION

Active pharmaceutical ingredients (APIs) can be prepared in a variety of different forms, for example, chemical derivatives, solvates, hydrates, co-crystals, or salts. APIs may also be amorphous, may have different crystalline polymorphs, or may exist in different solvation or hydration states. By varying the form of an API, it is possible to vary the physical properties thereof. For instance, crystalline polymorphs typically have different solubilities such that a more thermodynamically stable polymorph is less soluble than a less thermodynamically stable polymorph. Polymorphs can also differ in properties such as stability, bioavailability, morphology, vapor pressure, density, color, and compressibility. Accordingly, variation of the crystalline state of an API is one of many ways in which to modulate the physical and pharmacological properties thereof.

Various synthetic small organic molecules that are biologically active and generally known in the art as "fused pyrrolocarbazoles" have been prepared (See U.S. Pat. Nos. 5,475,110; 5,591,855; 5,594,009; 5,616,724; and 6,630,500). In addition, U.S. Pat. No. 5,705,511 discloses fused pyrrolocarbazole compounds which possess a variety of functional pharmacological activities. The fused pyrrolocarbazoles were disclosed to be used in a variety of ways, including: enhancing the function and/or survival of cells of neuronal lineage, either singularly or in combination with neurotrophic factor(s) and/or indolocarbazoles; enhancing trophic factor-induced activity; inhibition of protein kinase C ("PKC") activity; inhibition of trk tyrosine kinase activity; inhibition of proliferation of a prostate cancer cell-line; inhibition of the cellular pathways involved in the inflammation process; and enhancement of the survival of neuronal cells at risk of dying.

A specific fused pyrrolocarbazole compound, having the chemical designation 11-isobutyl-2-methyl-8-(2-pyrimidinylamino)-2,5,6,11,12,13-hexahydro-4H-indazolo[5,4-a]pyrrolo[3,4-c]carbazol-4-one is a potent, orally-active TIE-2/VEGF-R inhibitor having anti-tumor and anti-angiogenic activity, and is represented by the following formula (I):

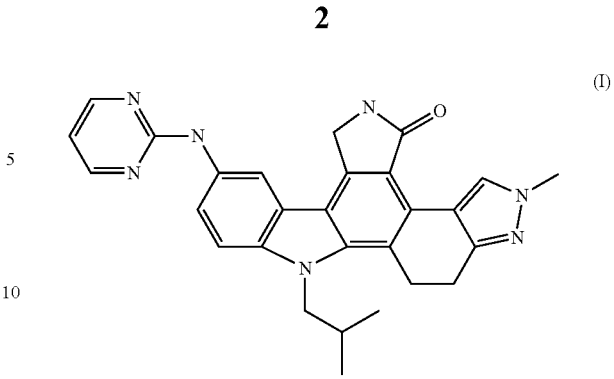

This Compound is referred to hereinafter as "Compound I". U.S. Pat. No. 7,169,802 describes Compound I and utility thereof.

Different chemical or solid state forms of Compound I can have different melting points, solubilities or rates of dissolution; these physical properties, either alone or in combination, can affect bioavailability. The physical properties of the various chemical/solid state forms of Compound I can also affect other aspects of drug development, such as manufacturing, processing, and storage characteristics. In light of the potential benefits of alternative forms of APIs, a need exists to identify and prepare alternative forms of Compound I.

SUMMARY OF THE INVENTION

Various chemical forms of Compound I are described, as well as methods of their preparation. Pharmaceutical compositions comprising one or more of these chemical forms are also described, as are methods of treatment utilizing such compositions.

The pharmaceutical compositions of the present invention may be used in a variety of ways, including: for inhibition of angiogenesis; as antitumor agents; for enhancing the function and/or survival of cells of neuronal lineage, either singularly or in combination with neurotrophic factor(s) and/or indolocarbazoles; for enhancing trophic factor-induced activity; inhibition of kinase activity, such as trk tyrosine kinase ("trk"), vascular endothelial growth factor receptor ("VEGFR") kinase, preferably VEGFR1 and VEGFR2, mixed lineage kinase ("MLK"), dual leucine zipper bearing kinase ("DLK"), platelet derived growth factor receptor kinase ("PDGFR"), protein kinase C ("PKC"), Tie-2, or CDK-1, -2, -3, -4, -5, -6; for inhibition of NGF-stimulated trk phosphorylation; for inhibition of proliferation of a prostate cancer cell-line; for inhibition of the cellular pathways involved in the inflammation process; and for enhancement of the survival of neuronal cells at risk of dying. In addition, the pharmaceutical compositions may useful for inhibition of c-met, c-kit, and mutated Flt-3 containing internal tandem duplications in the juxtamembrane domain. Because of these varied activities, the disclosed pharmaceutical compositions find utility in a variety of settings, including research and therapeutic environments.

In other embodiments, the pharmaceutical compositions of the present invention are useful for treating or preventing angiogenesis and angiogenic disorders such as cancer of solid tumors, endometriosis, retinopathy, diabetic retinopathy, psoriasis, hemangioblastoma, ocular disorders or macular degeneration. In another embodiment, the pharmaceutical compositions of the present invention are useful for treating or preventing neoplasia, rheumatoid arthritis, chronic arthritis, pulmonary fibrosis, myelofibrosis, abnormal wound healing, atherosclerosis, or restenosis. In further embodiments, the pharmaceutical compositions of the present invention are useful for treating or preventing neurodegenerative diseases and disorders, such as Alzheimer's disease, amyotrophic lateral sclerosis, Parkinson's disease, stroke, ischemia, Huntington's disease, AIDS dementia, epilepsy, multiple sclerosis, peripheral neuropathy, chemotherapy-induced peripheral neuropathy, AIDS related peripheral neuropathy, or injuries of the brain or spinal chord. In additional embodiments, the pharmaceutical compositions of the present invention are useful for treating or preventing prostate disorders such as prostate cancer or benign prostate hyperplasia. In still other embodiments, the pharmaceutical compositions of the present invention are useful for treating or preventing multiple myeloma and leukemias including, but not limited to, acute myelogenous leukemia, chronic myelogenous leukemia, acute lymphocytic leukemia, and chronic lymphocytic leukemia.

In a further aspect, the present invention is directed to pharmaceutical compositions which comprise one or more pharmaceutically acceptable excipients and a therapeutically effective amount of a form of the present invention.

BRIEF DESCRIPTION OF THE DRAWINGS

FIG. 55 is an X-ray Powder Diffractogram (XRPD) of the Compound I single crystal structure Form $A_0$.

DETAILED DESCRIPTION OF THE INVENTION

Figure 1:
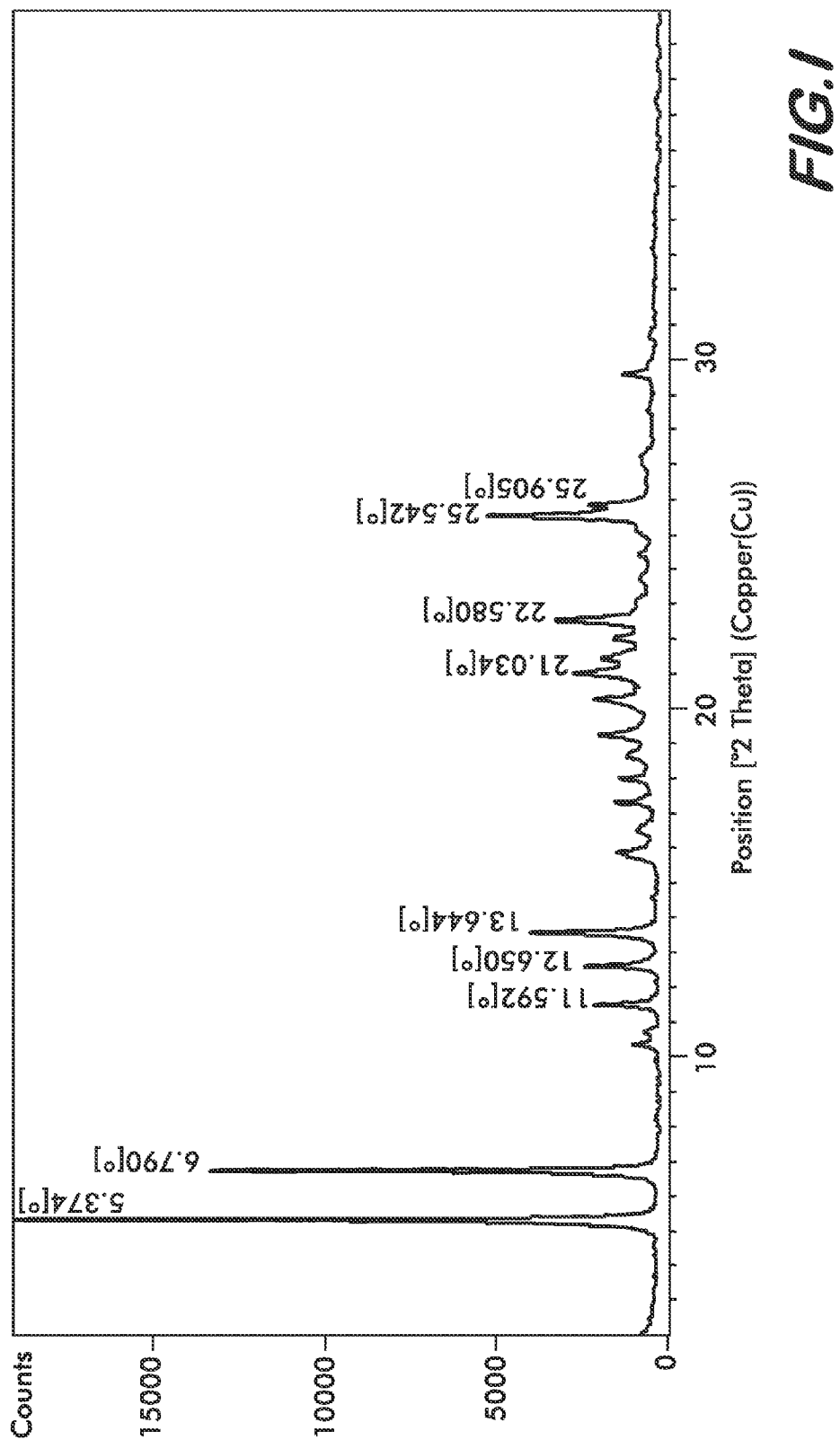
FIG. 1 is an X-ray Powder Diffractogram (XRPD) of Form pTSA-$A_1$

The existence has now been found of a number of chemical forms of Compound I. The preparation and description of these forms is described herein. Spectral data and structural depictions relating to these forms are shown in FIGS. 1-55.

More specifically, the existence has been found of several different crystalline forms of Compound I-para-toluenesulfonic acid (pTSA) 1:1 salt and Compound I-pTSA 1:2 salt drug substances. Specifically, the polymorph screening and isolation work described herein using Compound I-pTSA salt 1:X (X=1 or X=2) drug substances has resulted in the identification of 4 crystal forms: $pTSA-A_1$, $pTSA-A_2$, $pTSA-B_2$ and $pTSA-C_2$. No polymorphism has been detected for the Compound I-pTSA 1:1 salt ($pTSA-A_1$). Three polymorphs of Compound I-pTSA 1:2 salt ($pTSA-A_2$, $pTSA-B_2$, $pTSA-C_2$) have been prepared from different solvents using a crystallization technique.

Representative XRPD peaks for the $pTSA-A_1$ form are listed in the following Table 1.

TABLE 1

$pTSA-A_1$ form XRPD peaks

| Peak No. | Angle [°2 Theta] | d-spacing [Angstrom] | Intensity [%] |
|---|---|---|---|
| 1 | 5.37 | 16.45 | 100 |
| 2 | 6.79 | 13.02 | 70 |
| 3 | 11.59 | 7.63 | 8 |
| 4 | 12.65 | 6.99 | 11 |
| 5 | 12.70 | 6.98 | 10 |
| 6 | 13.64 | 6.48 | 20 |
| 7 | 15.94 | 5.56 | 6 |
| 8 | 17.37 | 5.10 | 6 |
| 9 | 19.26 | 4.60 | 7 |
| 10 | 20.34 | 4.36 | 6 |
| 11 | 21.03 | 4.22 | 9 |
| 12 | 22.58 | 3.93 | 13 |
| 13 | 25.54 | 3.48 | 25 |
| 14 | 25.91 | 3.44 | 8 |

Representative XRPD peaks for the $pTSA-A_2$ form are listed in the following Table 2.

TABLE 2

$pTSA-A_2$ form XRPD peaks

| Peak No. | Angle [°2 Theta] | d-spacing [Angstrom] | Intensity [%] |
|---|---|---|---|
| 1 | 3.71 | 23.80 | 26 |
| 2 | 5.63 | 15.69 | 100 |
| 3 | 8.48 | 10.43 | 90 |
| 4 | 11.30 | 7.83 | 26 |
| 5 | 12.46 | 7.11 | 34 |
| 6 | 13.26 | 6.68 | 13 |
| 7 | 14.05 | 6.30 | 5 |
| 8 | 14.49 | 6.11 | 11 |
| 9 | 14.94 | 5.93 | 12 |
| 10 | 15.52 | 5.71 | 13 |
| 11 | 16.99 | 5.22 | 25 |
| 12 | 17.02 | 5.21 | 24 |
| 13 | 17.46 | 5.08 | 6 |
| 14 | 18.21 | 4.87 | 31 |
| 15 | 20.28 | 4.38 | 20 |
| 16 | 20.56 | 4.32 | 7 |
| 17 | 21.97 | 4.05 | 13 |
| 18 | 22.52 | 3.95 | 11 |
| 19 | 22.91 | 3.88 | 10 |
| 20 | 23.95 | 3.72 | 29 |
| 21 | 25.18 | 3.54 | 23 |
| 22 | 25.55 | 3.49 | 12 |
| 23 | 26.60 | 3.35 | 7 |

Representative XRPD peaks for the $pTSA-B_2$ form are listed in the following Table 3.

TABLE 3

$pTSA-B_2$ form XRPD peaks

| Peak No. | Angle [°2 Theta] | d-spacing [Angstrom] | Intensity [%] |
|---|---|---|---|
| 1 | 3.76 | 23.54 | 39 |
| 2 | 5.63 | 15.69 | 100 |
| 3 | 7.53 | 11.74 | 6 |
| 4 | 8.40 | 10.52 | 87 |
| 5 | 11.31 | 7.83 | 36 |
| 6 | 12.11 | 7.31 | 13 |
| 7 | 12.46 | 7.10 | 8 |
| 8 | 12.75 | 6.94 | 7 |
| 9 | 13.17 | 6.72 | 18 |
| 10 | 14.12 | 6.27 | 8 |
| 11 | 14.73 | 6.01 | 25 |
| 12 | 15.12 | 5.86 | 32 |
| 13 | 16.42 | 5.40 | 6 |
| 14 | 16.87 | 5.26 | 22 |
| 15 | 17.00 | 5.22 | 21 |
| 16 | 17.29 | 5.13 | 8 |
| 17 | 17.87 | 4.97 | 8 |
| 18 | 18.14 | 4.89 | 6 |
| 19 | 18.61 | 4.77 | 7 |
| 20 | 20.15 | 4.41 | 20 |
| 21 | 22.52 | 3.95 | 5 |
| 22 | 24.03 | 3.70 | 20 |
| 23 | 24.60 | 3.62 | 21 |
| 24 | 24.78 | 3.59 | 11 |

TABLE 3-continued pTSA-B$_2$ form XRPD peaks

| Peak No. | Angle [°2 Theta] | d-spacing [Angstrom] | Intensity [%] |
|---|---|---|---|
| 25 | 25.47 | 3.50 | 12 |
| 26 | 26.12 | 3.41 | 5 |

Representative XRPD peaks for the pTSA-C$_2$ form are listed in the following Table 4.

TABLE 4 pTSA-C$_2$ form XRPD peaks

| Peak No. | Angle [°2 Theta] | d-spacing [Angstrom] | Intensity [%] |
|---|---|---|---|
| 1 | 3.84 | 23.00 | 6 |
| 2 | 5.72 | 15.45 | 50 |
| 3 | 8.49 | 10.41 | 100 |
| 4 | 11.37 | 7.77 | 35 |
| 5 | 12.13 | 7.29 | 5 |
| 6 | 13.26 | 6.67 | 29 |
| 7 | 14.19 | 6.24 | 8 |
| 8 | 14.81 | 5.98 | 7 |
| 9 | 15.17 | 5.84 | 14 |
| 10 | 16.95 | 5.23 | 40 |
| 11 | 17.06 | 5.19 | 22 |
| 12 | 17.37 | 5.10 | 16 |
| 13 | 21.55 | 4.12 | 7 |
| 14 | 24.11 | 3.69 | 6 |

The existence has also been found of four additional polymorphs of Compound I, A$_0$, B$_0$, C$_0$, and D$_0$, which have been prepared by quick cool and re-crystallization from different solvents. In addition, seventeen solvates of Compound I (S$_1$, S$_2$, S$_3$, S$_4$, S$_6$, S$_7$, S$_8$, S$_9$, S$_{10}$, S$_{13}$, S$_{14}$, S$_{15}$, S$_{16}$, S$_{17}$, S$_{18}$, S$_{19}$ and S$_{29}$) have been crystallized, and an amorphous solid (AS) has also been obtained. Finally, single crystal data for Compound I Form A$_0$, ethanol solvate, NMP 1:1 water solvate, tetrahydrofuran solvate and 2-propanol solvate has been obtained and characterized.

Representative XRPD peaks for the A$_0$ form are listed in the following Table 5.

TABLE 5

A$_0$ form XRPD peaks

| Peak No. | Angle [°2 Theta] | d-spacing [Angstrom] | Intensity [%] |
|---|---|---|---|
| 1 | 6.70 | 13.19 | 100 |
| 2 | 7.00 | 12.62 | 67 |
| 3 | 8.19 | 10.78 | 63 |
| 4 | 10.97 | 8.06 | 16 |
| 5 | 13.22 | 6.69 | 15 |
| 6 | 13.39 | 6.61 | 51 |
| 7 | 13.69 | 6.46 | 84 |
| 8 | 14.45 | 6.12 | 8 |
| 9 | 15.35 | 5.77 | 6 |
| 10 | 15.98 | 5.54 | 11 |
| 11 | 16.24 | 5.45 | 59 |
| 12 | 16.80 | 5.27 | 16 |
| 13 | 17.19 | 5.15 | 5 |
| 14 | 17.44 | 5.08 | 41 |
| 15 | 18.79 | 4.72 | 11 |
| 16 | 19.34 | 4.59 | 35 |
| 17 | 19.94 | 4.45 | 5 |
| 18 | 20.57 | 4.31 | 15 |
| 19 | 21.04 | 4.22 | 13 |
| 20 | 21.19 | 4.19 | 7 |
| 21 | 21.51 | 4.13 | 13 |
| 22 | 21.72 | 4.09 | 13 |

TABLE 5-continued

A$_0$ form XRPD peaks

| Peak No. | Angle [°2 Theta] | d-spacing [Angstrom] | Intensity [%] |
|---|---|---|---|
| 23 | 22.72 | 3.91 | 8 |
| 24 | 23.30 | 3.82 | 10 |
| 25 | 23.72 | 3.75 | 5 |
| 26 | 24.27 | 3.67 | 91 |
| 27 | 27.05 | 3.29 | 23 |
| 28 | 28.64 | 3.11 | 7 |
| 29 | 31.26 | 2.86 | 6 |

Representative XRPD peaks for the B$_0$ form are listed in the following Table 6.

TABLE 6

B$_0$ form XRPD peaks

| Peak No. | Angle [°2 Theta] | d-spacing [Angstrom] | Intensity [%] |
|---|---|---|---|
| 1 | 6.02 | 14.68 | 100 |
| 2 | 6.71 | 13.17 | 5 |
| 3 | 9.27 | 9.54 | 92 |
| 4 | 10.56 | 8.37 | 6 |
| 5 | 10.75 | 8.23 | 7 |
| 6 | 12.34 | 7.17 | 25 |
| 7 | 13.30 | 6.65 | 16 |
| 8 | 13.39 | 6.61 | 14 |
| 9 | 15.40 | 5.75 | 27 |
| 10 | 16.72 | 5.30 | 17 |
| 11 | 18.53 | 4.78 | 13 |
| 12 | 19.32 | 4.59 | 17 |
| 13 | 24.81 | 3.59 | 19 |
| 14 | 25.43 | 3.50 | 11 |
| 15 | 27.18 | 3.28 | 33 |

Representative XRPD peaks for the C$_0$ form are listed in the following Table 7.

TABLE 7

C$_0$ form XRPD peaks

| Peak No. | Angle [°2 Theta] | d-spacing [Angstrom] | Intensity [%] |
|---|---|---|---|
| 1 | 6.76 | 13.09 | 2 |
| 2 | 8.18 | 10.80 | 100 |
| 3 | 8.67 | 10.19 | 2 |
| 4 | 12.27 | 7.21 | 3 |
| 5 | 13.56 | 6.52 | 2 |
| 6 | 15.48 | 5.72 | 8 |
| 7 | 16.41 | 5.40 | 11 |
| 8 | 18.11 | 4.90 | 2 |
| 9 | 19.82 | 4.47 | 2 |
| 10 | 20.87 | 4.25 | 5 |
| 11 | 23.30 | 3.82 | 3 |
| 12 | 28.15 | 3.17 | 3 |

Representative XRPD peaks for the D$_0$ form are listed in the following Table 8.

TABLE 8

D$_0$ form XRPD peaks

| Peak No. | Angle [°2 Theta] | d-spacing [Angstrom] | Intensity [%] |
|---|---|---|---|
| 1 | 7.16 | 12.34 | 17 |
| 2 | 7.51 | 11.76 | 100 |
| 3 | 8.22 | 10.75 | 4 |
| 4 | 12.25 | 7.22 | 9 |
| 5 | 12.75 | 6.94 | 15 |
| 6 | 13.16 | 6.72 | 10 |

TABLE 8-continued

D$_0$ form XRPD peaks

| Peak No. | Angle [°2 Theta] | d-spacing [Angstrom] | Intensity [%] |
|---|---|---|---|
| 7 | 13.35 | 6.63 | 10 |
| 8 | 13.60 | 6.50 | 3 |
| 9 | 14.33 | 6.18 | 9 |
| 10 | 15.03 | 5.89 | 10 |
| 11 | 15.50 | 5.71 | 4 |
| 12 | 17.22 | 5.15 | 11 |
| 13 | 17.46 | 5.07 | 5 |
| 14 | 18.10 | 4.90 | 3 |
| 15 | 19.04 | 4.66 | 8 |
| 16 | 20.35 | 4.36 | 10 |
| 17 | 21.04 | 4.22 | 29 |
| 18 | 23.31 | 3.81 | 11 |
| 19 | 25.20 | 3.53 | 3 |
| 20 | 26.86 | 3.32 | 19 |
| 21 | 27.64 | 3.22 | 4 |
| 22 | 28.16 | 3.17 | 5 |

Representative XRPD peaks for the S$_1$ form are listed in the following Table 9.

TABLE 9

S$_1$ form XRPD peaks

| Peak No. | Angle [°2 Theta] | d-spacing [Angstrom] | Intensity [%] |
|---|---|---|---|
| 1 | 5.50 | 16.05 | 100 |
| 2 | 7.21 | 12.26 | 22 |
| 3 | 7.76 | 11.39 | 61 |
| 4 | 8.75 | 10.10 | 6 |
| 5 | 10.99 | 8.04 | 10 |
| 6 | 12.21 | 7.24 | 14 |
| 7 | 13.02 | 6.79 | 16 |
| 8 | 17.33 | 5.11 | 8 |
| 9 | 19.69 | 4.51 | 30 |
| 10 | 20.84 | 4.26 | 5 |
| 11 | 21.52 | 4.13 | 7 |
| 12 | 22.04 | 4.03 | 12 |
| 13 | 23.05 | 3.86 | 8 |
| 14 | 25.26 | 3.52 | 28 |
| 15 | 26.31 | 3.39 | 5 |
| 16 | 27.53 | 3.24 | 6 |

Representative XRPD peaks for the S$_2$ form are listed in the following Table 10.

TABLE 10

S$_2$ form XRPD peaks

| Peak No. | Angle [°2 Theta] | d-spacing [Angstrom] | Intensity [%] |
|---|---|---|---|
| 1 | 7.26 | 12.17 | 100 |
| 2 | 13.11 | 6.75 | 2 |
| 3 | 13.25 | 6.68 | 2 |
| 4 | 14.52 | 6.10 | 15 |
| 5 | 18.11 | 4.90 | 2 |
| 6 | 19.91 | 4.46 | 4 |
| 7 | 21.63 | 4.11 | 8 |
| 8 | 21.84 | 4.07 | 2 |
| 9 | 27.62 | 3.23 | 2 |

Representative XRPD peaks for the S$_3$ form are listed in the following Table 11.

TABLE 11

S$_3$ form XRPD peaks

| Peak No. | Angle [°2 Theta] | d-spacing [Angstrom] | Intensity [%] |
|---|---|---|---|
| 1 | 6.68 | 13.23 | 100 |
| 2 | 7.06 | 12.51 | 4 |
| 3 | 7.54 | 11.72 | 7 |
| 4 | 12.34 | 7.16 | 6 |
| 5 | 12.98 | 6.81 | 4 |
| 6 | 17.40 | 5.09 | 37 |
| 7 | 18.39 | 4.82 | 8 |
| 8 | 20.04 | 4.43 | 21 |
| 9 | 20.58 | 4.31 | 25 |
| 10 | 25.43 | 3.50 | 20 |
| 11 | 26.35 | 3.38 | 6 |
| 12 | 30.42 | 2.94 | 4 |
| 13 | 30.97 | 2.89 | 7 |

Representative XRPD peaks for the S$_4$ form are listed in the following Table 12.

TABLE 12

S$_4$ form XRPD peaks

| Peak No. | Angle [°2 Theta] | d-spacing [Angstrom] | Intensity [%] |
|---|---|---|---|
| 1 | 5.55 | 15.92 | 100 |
| 2 | 7.84 | 11.26 | 23 |
| 3 | 12.41 | 7.13 | 7 |
| 4 | 13.05 | 6.78 | 14 |
| 5 | 15.23 | 5.81 | 6 |
| 6 | 16.68 | 5.31 | 6 |
| 7 | 17.58 | 5.04 | 7 |
| 8 | 18.86 | 4.70 | 16 |
| 9 | 19.71 | 4.50 | 19 |
| 10 | 20.09 | 4.42 | 14 |
| 11 | 22.31 | 3.98 | 18 |
| 12 | 23.00 | 3.86 | 7 |
| 13 | 23.36 | 3.80 | 8 |
| 14 | 25.60 | 3.48 | 13 |

Representative XRPD peaks for the S$_6$ form are listed in the following Table 13.

TABLE 13

S$_6$ form XRPD peaks

| Peak No. | Angle [°2 Theta] | d-spacing [Angstrom] | Intensity [%] |
|---|---|---|---|
| 1 | 6.38 | 13.85 | 24 |
| 2 | 6.69 | 13.20 | 45 |
| 3 | 8.10 | 10.91 | 89 |
| 4 | 8.56 | 10.33 | 32 |
| 5 | 12.12 | 7.30 | 36 |
| 6 | 12.58 | 7.03 | 10 |
| 7 | 13.14 | 6.73 | 32 |
| 8 | 13.46 | 6.57 | 48 |
| 9 | 13.76 | 6.43 | 8 |
| 10 | 14.83 | 5.97 | 25 |
| 11 | 15.39 | 5.75 | 39 |
| 12 | 16.22 | 5.46 | 19 |
| 13 | 17.06 | 5.19 | 26 |
| 14 | 17.30 | 5.12 | 79 |
| 15 | 17.71 | 5.00 | 5 |
| 16 | 18.02 | 4.92 | 13 |
| 17 | 18.41 | 4.81 | 13 |
| 18 | 18.70 | 4.74 | 13 |
| 19 | 18.98 | 4.67 | 9 |
| 20 | 20.78 | 4.27 | 100 |
| 21 | 21.69 | 4.09 | 32 |
| 22 | 22.34 | 3.98 | 10 |

TABLE 13-continued

S₆ form XRPD peaks

| Peak No. | Angle [°2 Theta] | d-spacing [Angstrom] | Intensity [%] |
|---|---|---|---|
| 23 | 22.96 | 3.87 | 26 |
| 24 | 23.43 | 3.79 | 24 |
| 25 | 24.19 | 3.68 | 11 |
| 26 | 24.65 | 3.61 | 5 |
| 27 | 27.13 | 3.28 | 8 |
| 28 | 28.03 | 3.18 | 76 |
| 29 | 28.98 | 3.08 | 5 |
| 30 | 29.76 | 3.00 | 10 |
| 31 | 36.76 | 2.44 | 5 |

Representative XRPD peaks for the S₇ form are listed in the following Table 14.

TABLE 14

S₇ form XRPD peaks

| Peak No. | Angle [°2 Theta] | d-spacing [Angstrom] | Intensity [%] |
|---|---|---|---|
| 1 | 6.87 | 12.87 | 100 |
| 2 | 12.80 | 6.91 | 3 |
| 3 | 13.93 | 6.35 | 21 |
| 4 | 18.14 | 4.89 | 4 |
| 5 | 18.35 | 4.83 | 3 |
| 6 | 19.27 | 4.60 | 16 |
| 7 | 20.87 | 4.25 | 10 |
| 8 | 21.06 | 4.22 | 10 |
| 9 | 23.25 | 3.82 | 3 |
| 10 | 24.96 | 3.56 | 3 |
| 11 | 26.86 | 3.32 | 8 |
| 12 | 27.05 | 3.29 | 3 |
| 13 | 29.56 | 3.02 | 2 |
| 14 | 33.24 | 2.69 | 2 |

Representative XRPD peaks for the S₈ form are listed in the following Table 15.

TABLE 15

S₈ form XRPD peaks

| Peak No. | Angle [°2 Theta] | d-spacing [Angstrom] | Intensity [%] |
|---|---|---|---|
| 1 | 6.35 | 13.91 | 58 |
| 2 | 7.32 | 12.08 | 100 |
| 3 | 7.52 | 11.75 | 11 |
| 4 | 12.31 | 7.19 | 7 |
| 5 | 12.59 | 7.03 | 16 |
| 6 | 12.70 | 6.96 | 9 |
| 7 | 13.07 | 6.77 | 19 |
| 8 | 14.22 | 6.22 | 9 |
| 9 | 14.70 | 6.02 | 15 |
| 10 | 17.32 | 5.12 | 8 |
| 11 | 17.69 | 5.01 | 16 |
| 12 | 18.08 | 4.90 | 11 |
| 13 | 18.68 | 4.75 | 9 |
| 14 | 18.79 | 4.72 | 8 |
| 15 | 19.08 | 4.65 | 8 |
| 16 | 19.21 | 4.62 | 5 |
| 17 | 19.91 | 4.46 | 19 |
| 18 | 20.90 | 4.25 | 8 |
| 19 | 21.33 | 4.16 | 11 |
| 20 | 21.54 | 4.12 | 42 |
| 21 | 21.65 | 4.10 | 52 |
| 22 | 23.88 | 3.72 | 15 |
| 23 | 24.12 | 3.69 | 11 |
| 24 | 26.27 | 3.39 | 5 |
| 25 | 26.37 | 3.38 | 5 |
| 26 | 27.40 | 3.25 | 26 |
| 27 | 28.05 | 3.18 | 5 |
| 28 | 28.16 | 3.17 | 7 |

Representative XRPD peaks for the S₉ form are listed in the following Table 16.

TABLE 16

S₉ form XRPD peaks

| Peak No. | Angle [°2 Theta] | d-spacing [Angstrom] | Intensity [%] |
|---|---|---|---|
| 1 | 6.77 | 13.04 | 100 |
| 2 | 12.69 | 6.97 | 1 |
| 3 | 13.53 | 6.54 | 13 |
| 4 | 18.23 | 4.86 | 2 |
| 5 | 18.81 | 4.71 | 5 |
| 6 | 20.17 | 4.40 | 2 |
| 7 | 20.84 | 4.26 | 4 |
| 8 | 22.63 | 3.93 | 1 |
| 9 | 26.66 | 3.34 | 1 |
| 10 | 26.80 | 3.32 | 3 |

Representative XRPD peaks for the S₁₀ form are listed in the following Table 17.

TABLE 17

S₁₀ form XRPD peaks

| Peak No. | Angle [°2 Theta] | d-spacing [Angstrom] | Intensity [%] |
|---|---|---|---|
| 1 | 5.84 | 15.13 | 35 |
| 2 | 7.64 | 11.57 | 100 |
| 3 | 9.54 | 9.27 | 10 |
| 4 | 10.86 | 8.15 | 7 |
| 5 | 11.49 | 7.70 | 18 |
| 6 | 12.76 | 6.94 | 5 |
| 7 | 15.04 | 5.89 | 6 |
| 8 | 15.42 | 5.75 | 6 |
| 9 | 17.55 | 5.05 | 9 |
| 10 | 17.96 | 4.94 | 12 |
| 11 | 18.56 | 4.78 | 11 |
| 12 | 19.90 | 4.46 | 5 |
| 13 | 20.23 | 4.39 | 20 |
| 14 | 21.61 | 4.11 | 10 |
| 15 | 22.19 | 4.01 | 6 |
| 16 | 23.43 | 3.80 | 5 |
| 17 | 23.84 | 3.73 | 23 |
| 18 | 26.26 | 3.39 | 16 |
| 19 | 28.81 | 3.10 | 6 |

Representative XRPD peaks for the S₁₃ form are listed in the following Table 18.

TABLE 18

S₁₃ form XRPD peaks

| Peak No. | Angle [°2 Theta] | d-spacing [Angstrom] | Intensity [%] |
|---|---|---|---|
| 1 | 5.46 | 16.18 | 13 |
| 2 | 6.75 | 13.09 | 35 |
| 3 | 7.08 | 12.48 | 100 |
| 4 | 7.26 | 12.17 | 64 |
| 5 | 7.60 | 11.62 | 93 |
| 6 | 8.18 | 10.80 | 12 |
| 7 | 11.73 | 7.54 | 8 |
| 8 | 12.96 | 6.83 | 17 |
| 9 | 13.54 | 6.53 | 5 |
| 10 | 14.16 | 6.25 | 18 |
| 11 | 14.57 | 6.07 | 14 |
| 12 | 15.39 | 5.75 | 12 |
| 13 | 16.48 | 5.38 | 19 |
| 14 | 17.55 | 5.05 | 5 |
| 15 | 18.32 | 4.84 | 13 |
| 16 | 18.69 | 4.74 | 10 |
| 17 | 19.46 | 4.56 | 19 |
| 18 | 22.05 | 4.03 | 8 |
| 19 | 22.70 | 3.91 | 23 |
| 20 | 23.02 | 3.86 | 15 |

TABLE 18-continued

| | $S_{13}$ form XRPD peaks | | |
|---|---|---|---|
| Peak No. | Angle [°2 Theta] | d-spacing [Angstrom] | Intensity [%] |
| 21 | 25.13 | 3.54 | 7 |
| 22 | 26.37 | 3.38 | 8 |
| 23 | 28.53 | 3.13 | 12 |

Representative XRPD peaks for the $S_{14}$ form are listed in the following Table 19.

TABLE 19

| | $S_{14}$ form XRPD peaks | | |
|---|---|---|---|
| Peak No. | Angle [°2 Theta] | d-spacing [Angstrom] | Intensity [%] |
| 1 | 6.02 | 14.68 | 7 |
| 2 | 7.15 | 12.36 | 4 |
| 3 | 7.44 | 11.87 | 100 |
| 4 | 12.41 | 7.13 | 4 |
| 5 | 13.31 | 6.65 | 3 |
| 6 | 14.29 | 6.19 | 4 |
| 7 | 14.88 | 5.95 | 20 |
| 8 | 18.86 | 4.70 | 4 |
| 9 | 19.21 | 4.62 | 6 |
| 10 | 20.20 | 4.39 | 12 |
| 11 | 21.61 | 4.11 | 9 |
| 12 | 22.39 | 3.97 | 10 |
| 13 | 27.19 | 3.28 | 3 |
| 14 | 27.45 | 3.25 | 4 |

Representative XRPD peaks for the $S_{15}$ form are listed in the following Table 20.

TABLE 20

| | $S_{15}$ form XRPD peaks | | |
|---|---|---|---|
| Peak No. | Angle [°2 Theta] | d-spacing [Angstrom] | Intensity [%] |
| 1 | 7.29 | 12.11 | 100 |
| 2 | 7.59 | 11.64 | 4 |
| 3 | 12.30 | 7.19 | 11 |
| 4 | 14.31 | 6.18 | 6 |
| 5 | 14.59 | 6.07 | 10 |
| 6 | 18.77 | 4.72 | 4 |
| 7 | 18.95 | 4.68 | 5 |
| 8 | 19.79 | 4.48 | 11 |
| 9 | 21.27 | 4.17 | 12 |
| 10 | 21.96 | 4.04 | 6 |
| 11 | 26.98 | 3.30 | 5 |

Representative XRPD peaks for the $S_{16}$ form are listed in the following Table 21.

TABLE 21

| | $S_{16}$ form XRPD peaks | | |
|---|---|---|---|
| Peak No. | Angle [°2 Theta] | d-spacing [Angstrom] | Intensity [%] |
| 1 | 6.50 | 13.60 | 100 |
| 2 | 7.28 | 12.13 | 28 |
| 3 | 7.96 | 11.09 | 55 |
| 4 | 8.49 | 10.41 | 6 |
| 5 | 12.11 | 7.30 | 35 |
| 6 | 12.77 | 6.93 | 9 |
| 7 | 14.81 | 5.98 | 10 |
| 8 | 15.28 | 5.79 | 23 |
| 9 | 16.19 | 5.47 | 11 |
| 10 | 17.19 | 5.15 | 64 |
| 11 | 18.22 | 4.87 | 16 |
| 12 | 19.14 | 4.63 | 7 |

TABLE 21-continued

| | $S_{16}$ form XRPD peaks | | |
|---|---|---|---|
| Peak No. | Angle [°2 Theta] | d-spacing [Angstrom] | Intensity [%] |
| 13 | 19.83 | 4.47 | 13 |
| 14 | 20.36 | 4.36 | 71 |
| 15 | 20.68 | 4.29 | 96 |
| 16 | 21.65 | 4.10 | 9 |
| 17 | 23.06 | 3.85 | 9 |
| 18 | 24.53 | 3.63 | 5 |
| 19 | 25.21 | 3.53 | 37 |
| 20 | 26.13 | 3.41 | 17 |
| 21 | 26.47 | 3.36 | 15 |
| 22 | 27.92 | 3.19 | 55 |
| 23 | 30.74 | 2.91 | 15 |

Representative XRPD peaks for the $S_{17}$ form are listed in the following Table 22.

TABLE 22

| | $S_{17}$ form XRPD peaks | | |
|---|---|---|---|
| Peak No. | Angle [°2 Theta] | d-spacing [Angstrom] | Intensity [%] |
| 1 | 5.34 | 16.52 | 40 |
| 2 | 6.24 | 14.16 | 100 |
| 3 | 7.66 | 11.53 | 9 |
| 4 | 12.68 | 6.98 | 85 |
| 5 | 13.43 | 6.59 | 5 |
| 6 | 15.66 | 5.65 | 6 |
| 7 | 16.25 | 5.45 | 9 |
| 8 | 17.37 | 5.10 | 66 |
| 9 | 18.12 | 4.89 | 76 |
| 10 | 19.16 | 4.63 | 9 |
| 11 | 19.83 | 4.47 | 15 |
| 12 | 20.51 | 4.33 | 54 |
| 13 | 21.51 | 4.13 | 55 |
| 14 | 22.07 | 4.02 | 16 |
| 15 | 22.71 | 3.91 | 43 |
| 16 | 24.34 | 3.65 | 16 |
| 17 | 25.70 | 3.46 | 27 |
| 18 | 26.28 | 3.39 | 14 |
| 19 | 27.13 | 3.28 | 22 |
| 20 | 27.57 | 3.23 | 39 |
| 21 | 28.63 | 3.12 | 38 |
| 22 | 30.72 | 2.91 | 30 |
| 23 | 35.49 | 2.53 | 6 |
| 24 | 38.96 | 2.31 | 6 |

Representative XRPD peaks for the $S_{18}$ form are listed in the following Table 23.

TABLE 23

| | $S_{18}$ form XRPD peaks | | |
|---|---|---|---|
| Peak No. | Angle [°2 Theta] | d-spacing [Angstrom] | Intensity [%] |
| 1 | 5.91 | 14.93 | 72 |
| 2 | 6.66 | 13.27 | 45 |
| 3 | 7.37 | 11.99 | 19 |
| 4 | 11.85 | 7.46 | 16 |
| 5 | 13.40 | 6.60 | 7 |
| 6 | 14.34 | 6.17 | 14 |
| 7 | 14.94 | 5.92 | 8 |
| 8 | 15.38 | 5.76 | 9 |
| 9 | 16.25 | 5.45 | 38 |
| 10 | 17.59 | 5.04 | 100 |
| 11 | 18.79 | 4.72 | 15 |
| 12 | 19.71 | 4.50 | 32 |
| 13 | 21.03 | 4.22 | 9 |
| 14 | 23.82 | 3.73 | 42 |

TABLE 23-continued

S$_{18}$ form XRPD peaks

| Peak No. | Angle [°2 Theta] | d-spacing [Angstrom] | Intensity [%] |
|---|---|---|---|
| 15 | 24.51 | 3.63 | 16 |
| 16 | 25.37 | 3.51 | 6 |
| 17 | 26.75 | 3.33 | 6 |
| 18 | 28.37 | 3.14 | 5 |

Representative XRPD peaks for the S$_{19}$ form are listed in the following Table 24.

TABLE 24

S$_{19}$ form XRPD peaks

| Peak No. | Angle [°2 Theta] | d-spacing [Angstrom] | Intensity [%] |
|---|---|---|---|
| 1 | 6.75 | 13.09 | 2 |
| 2 | 8.27 | 10.69 | 100 |
| 3 | 8.32 | 10.62 | 68 |
| 4 | 11.41 | 7.75 | 3 |
| 5 | 11.59 | 7.63 | 4 |
| 6 | 13.06 | 6.77 | 2 |
| 7 | 16.53 | 5.36 | 12 |
| 8 | 16.59 | 5.34 | 5 |
| 9 | 17.50 | 5.06 | 2 |
| 10 | 18.22 | 4.87 | 2 |
| 11 | 20.69 | 4.29 | 5 |
| 12 | 20.81 | 4.26 | 2 |
| 13 | 22.66 | 3.92 | 2 |
| 14 | 22.89 | 3.88 | 2 |
| 15 | 23.28 | 3.82 | 5 |
| 16 | 24.89 | 3.57 | 5 |
| 17 | 26.16 | 3.40 | 3 |
| 18 | 26.23 | 3.39 | 2 |
| 19 | 33.38 | 2.68 | 3 |

Representative XRPD peaks for the S$_{20}$ form are listed in the following Table 25.

TABLE 25

S$_{20}$ form XRPD peaks

| Peak No. | Angle [°2 Theta] | d-spacing [Angstrom] | Intensity [%] |
|---|---|---|---|
| 1 | 3.74 | 23.61 | 31 |
| 2 | 6.64 | 13.31 | 99 |
| 3 | 6.77 | 13.05 | 100 |
| 4 | 7.04 | 12.54 | 24 |
| 5 | 7.36 | 12.00 | 41 |
| 6 | 7.54 | 11.71 | 34 |
| 7 | 8.23 | 10.73 | 28 |
| 8 | 11.03 | 8.02 | 49 |
| 9 | 11.35 | 7.79 | 16 |
| 10 | 11.74 | 7.53 | 25 |
| 11 | 12.73 | 6.95 | 44 |
| 12 | 13.45 | 6.58 | 25 |
| 13 | 13.71 | 6.45 | 47 |
| 14 | 14.48 | 6.11 | 20 |
| 15 | 15.27 | 5.80 | 62 |
| 16 | 15.77 | 5.61 | 34 |
| 17 | 16.30 | 5.43 | 25 |
| 18 | 17.51 | 5.06 | 21 |
| 19 | 18.38 | 4.82 | 25 |
| 20 | 18.74 | 4.73 | 32 |
| 21 | 19.38 | 4.58 | 17 |
| 22 | 21.31 | 4.17 | 32 |
| 23 | 22.06 | 4.03 | 17 |
| 24 | 23.76 | 3.74 | 22 |
| 25 | 24.27 | 3.66 | 48 |
| 26 | 25.39 | 3.50 | 24 |
| 27 | 25.62 | 3.47 | 24 |
| 28 | 25.98 | 3.43 | 44 |
| 29 | 26.35 | 3.38 | 32 |
| 30 | 26.86 | 3.32 | 43 |

Accordingly, in one aspect, the present invention provides a crystalline form of Compound I that is Form pTSA-A$_1$, Form pTSA-A$_2$, Form pTSA-B$_2$, Form pTSA-C$_2$ or a mixture thereof. In another aspect, the crystalline form is Form pTSA-A$_1$. In an additional aspect, the crystalline form is Form pTSA-A$_2$. In yet another aspect, the crystalline form is Form pTSA-B$_2$. In still another aspect, the crystalline form is Form pTSA-C$_2$.

An additional aspect of the present invention pertains to a crystalline form of Compound I that is Form pTSA-A$_1$, characterized by an X-ray powder diffraction pattern comprising one or more of the following peaks: 5.37±0.2 degrees 2-theta, 6.79±0.2 degrees 2-theta, 13.64±0.2 degrees 2-theta, 22.58±0.2 degrees 2-theta and/or 25.54±0.2 degrees 2-theta when measured using Cu—Kα radiation (λ=1.54056 Å). In one aspect, the X-ray powder diffraction pattern of Form pTSA-A$_1$ comprises a peak at 5.37±0.2 degrees 2-theta and one or more of the following peaks 6.79±0.2 degrees 2-theta, 13.64±0.2 degrees 2-theta, 22.58±0.2 degrees 2-theta and/or 25.54±0.2 degrees 2-theta when measured using Cu—Kα radiation (λ=1.54056 Å). In another aspect, the X-ray powder diffraction pattern of Form pTSA-A$_1$ comprises peaks at 5.37±0.2 degrees 2-theta and 6.79±0.2 degrees 2-theta and one or more of the following peaks: 13.64±0.2 degrees 2-theta, 22.58±0.2 degrees 2-theta and/or 25.54±0.2 degrees 2-theta when measured using Cu—Kα radiation (λ=1.54056 Å). In yet another aspect, the X-ray powder diffraction pattern of Form pTSA-A$_1$ comprises peaks at 5.37±0.2 degrees 2-theta, 6.79±0.2 degrees 2-theta, and 25.54±0.2 degrees 2-theta and one or more of the following peaks: 13.64±0.2 degrees 2-theta and/or 22.58±0.2 degrees 2-theta when measured using Cu—Kα radiation (λ=1.54056 Å). In still another aspect, the X-ray powder diffraction pattern of Form pTSA-A$_1$ comprises peaks at 5.37±0.2 degrees 2-theta, 6.79±0.2 degrees 2-theta, 13.64±0.2 degrees 2-theta, 22.58±0.2 degrees 2-theta and/or 25.54±0.2 degrees 2-theta when measured using Cu—Kα radiation (λ=1.54056 Å). In yet another aspect, the crystalline form Form pTSA-A$_1$ has an X-ray powder diffraction pattern substantially as depicted in FIG. 1.

Figure 3:
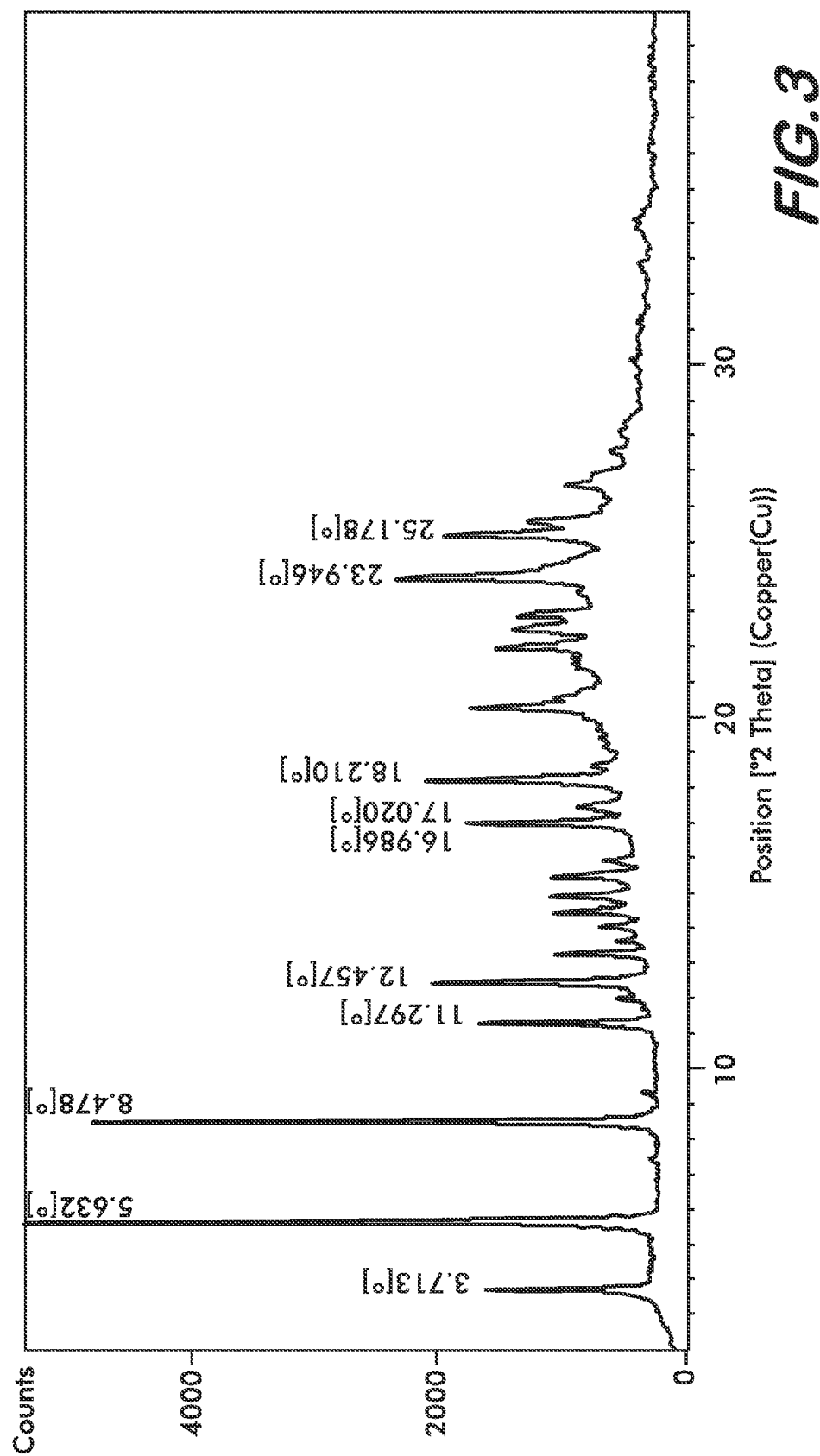
FIG. 3 is an X-ray Powder Diffractogram (XRPD) of Form pTSA-$A_2$

Another aspect of the present invention pertains to a crystalline form of Compound I that is Form pTSA-A$_2$, characterized by an X-ray powder diffraction pattern comprising one or more of the following peaks: 5.63±0.2 degrees 2-theta, 8.48±0.2 degrees 2-theta, 12.46±0.2 degrees 2-theta, 18.21±0.2 degrees 2-theta and/or 23.95±0.2 degrees 2-theta when measured using Cu—Kα radiation (λ=1.54056 Å). In another aspect, the crystalline form has an X-ray powder diffraction pattern substantially as depicted in FIG. 3.

Figure 5:
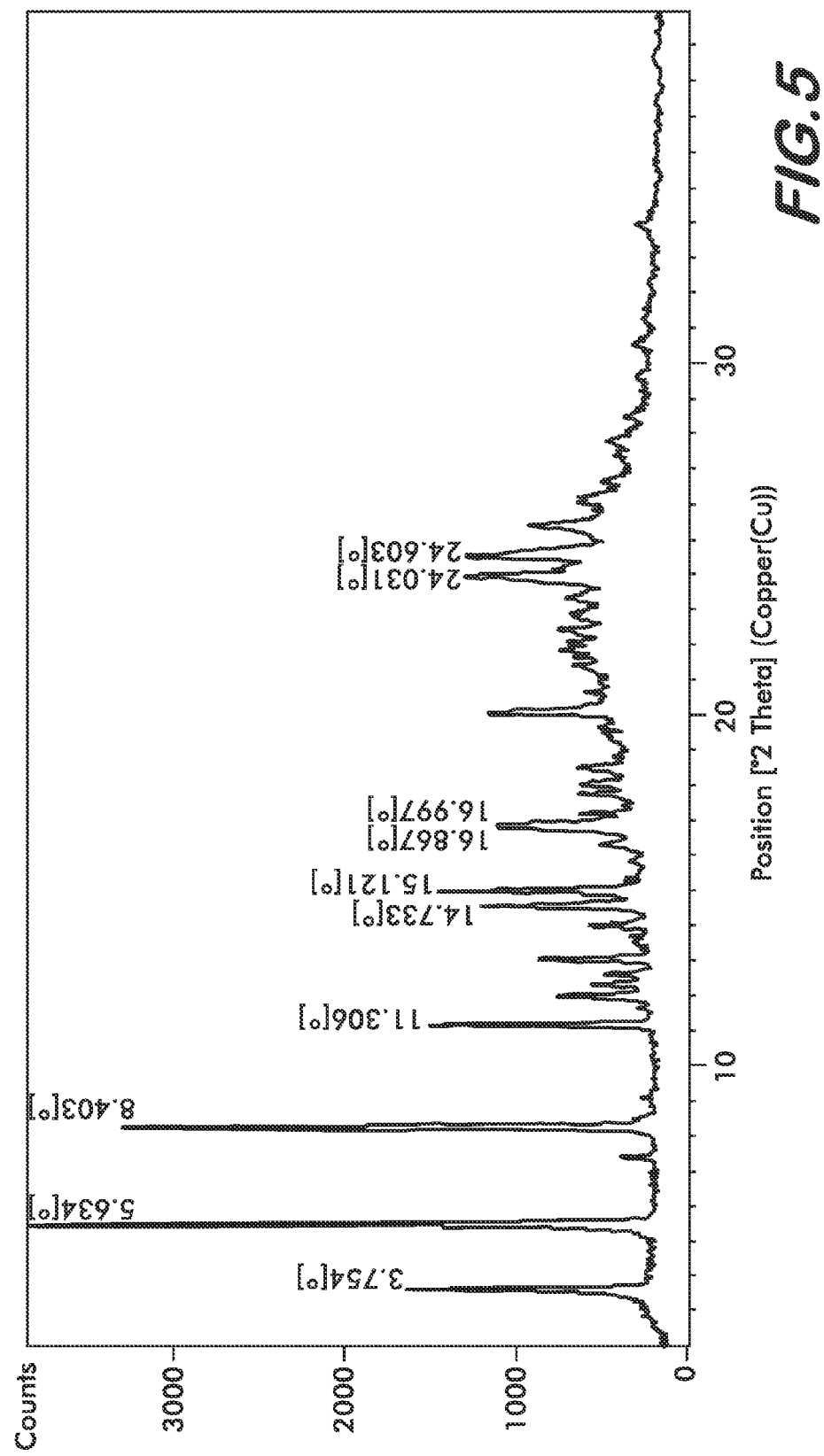
FIG. 5 is an X-ray Powder Diffractogram (XRPD) of Form pTSA-$B_2$

A further aspect pertains to a crystalline form of Compound I that is Form pTSA-B$_2$, characterized by an X-ray powder diffraction pattern comprising one or more of the following peaks: 3.75, 5.63, 8.40, 11.31 and/or 15.12±0.2 degrees 2-theta. In an additional aspect, the crystalline form has an X-ray powder diffraction pattern substantially as depicted in FIG. 5.

Figure 7:
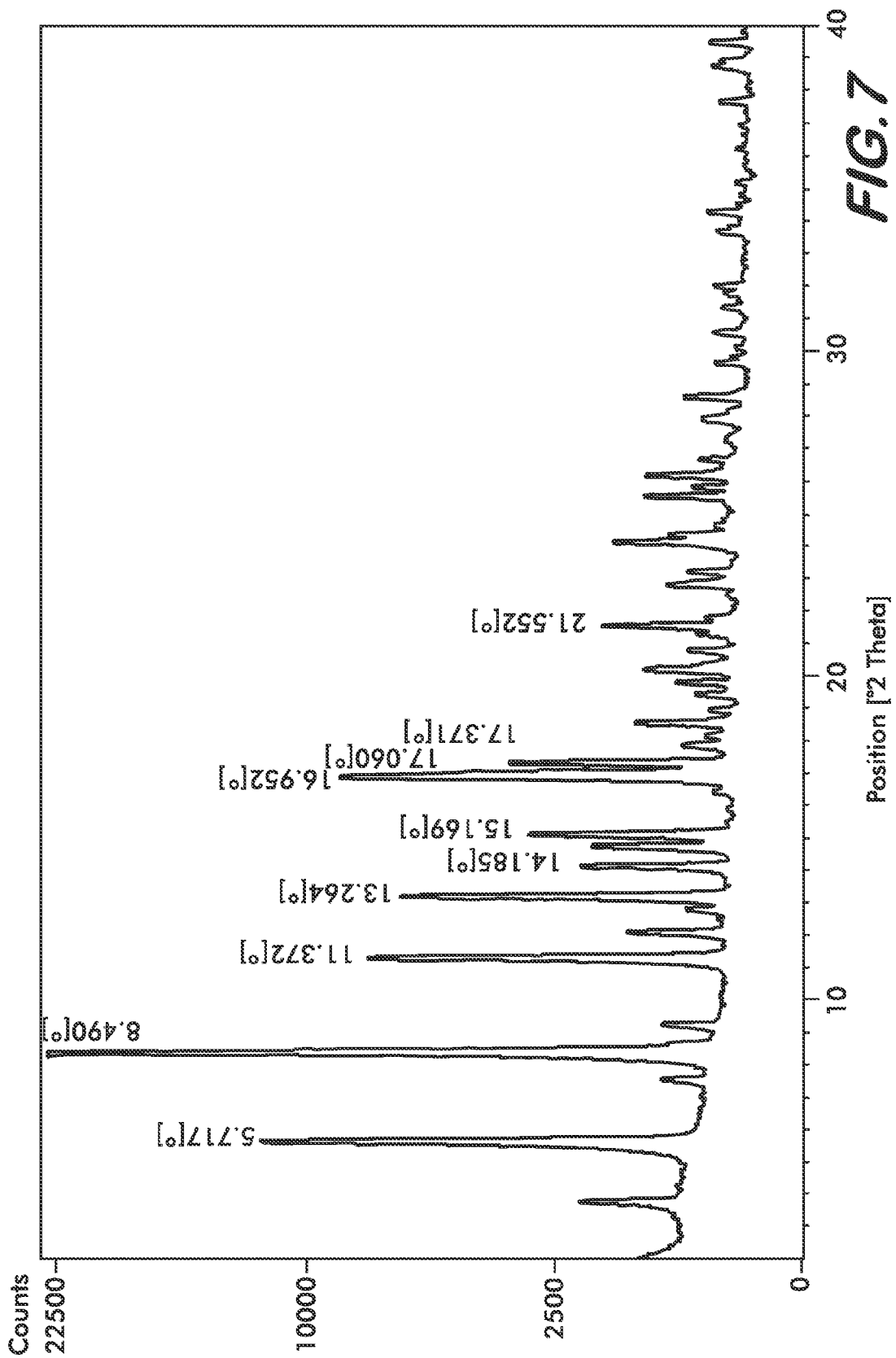
FIG. 7 is an X-ray Powder Diffractogram (XRPD) of Form pTSA-$C_2$
Figure 8:
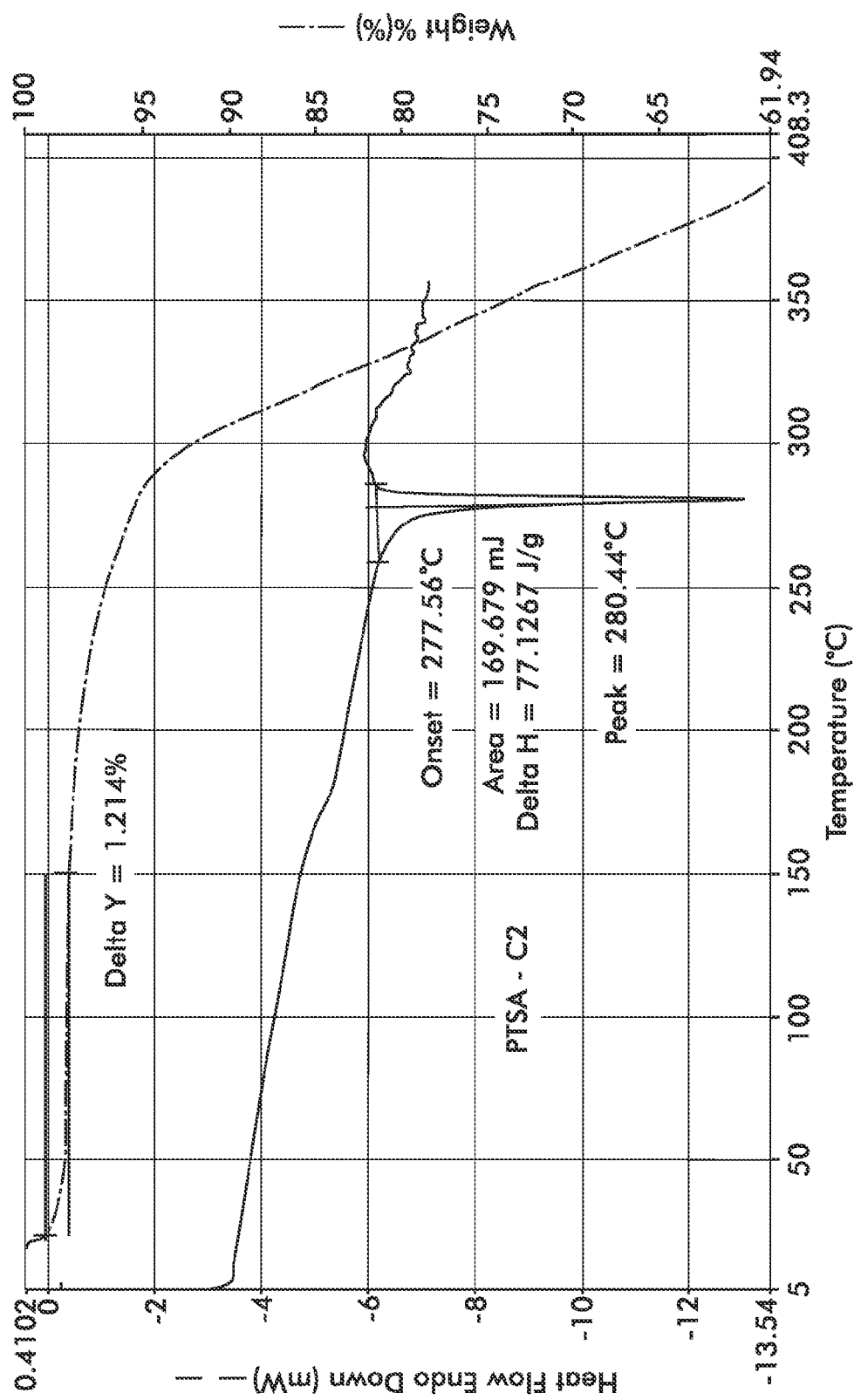
FIG. 8 is a Differential Scanning calorimetry (DSC) Thermogram and Thermo-Gravimetric Analysis (TGA) Thermogram overlay of Form pTSA-$C_2$

An additional aspect of the present invention pertains to a crystalline form of Compound I that is Form pTSA-C$_2$, characterized by an X-ray powder diffraction pattern comprising one or more of the following peaks: 5.72, 8.49, 11.37, 13.26 and/or 16.95±0.2 degrees 2-theta. In a further aspect, the crystalline form has an X-ray powder diffraction pattern substantially as depicted in FIG. 7.

Yet another aspect of the present invention pertains to a pharmaceutical composition comprising Compound I Form pTSA-$A_1$, Compound I Form pTSA-$A_2$, Compound I Form pTSA-$B_2$, Compound I Form pTSA-$C_2$ or a mixture thereof. In a further aspect, the pharmaceutical composition comprises Form pTSA-$A_1$. In another aspect, the pharmaceutical composition comprises Form pTSA-$A_2$. In still another aspect, the pharmaceutical composition comprises Form pTSA-$B_2$. In an additional aspect, the pharmaceutical composition comprises Form pTSA-$C_2$.

Still another aspect of the present invention pertains to a method for preparing a crystalline form of Compound I that is Form pTSA-$A_1$, comprising the step of crystallizing Compound I in the presence of methylene chloride to yield Form pTSA-$A_1$. A further aspect pertains to a method for preparing a crystalline form of Compound I that is Form pTSA-$A_2$, comprising the step of crystallizing Compound I in the presence of methylene chloride and pTSA acid monohydrate to yield Form pTSA-$A_2$. An additional aspect pertains to a method for preparing a crystalline form of Compound I that is Form pTSA-$B_2$, comprising the step of crystallizing Compound I in the presence of acetone and pTSA acid monohydrate to yield Form pTSA-$B_2$. Still a further aspect of the present invention pertains to a method for preparing a crystalline form of Compound I that is Form pTSA-$C_2$, comprising the step of crystallizing Compound I in the presence of n-propanol and p-toluenesulfonic acid monohydrate to yield Form pTSA-$C_2$.

A further aspect of the present invention pertains to a method of treating solid tumors comprising the step of administering to a patient in need thereof a therapeutically effective amount of a crystalline form of Compound I that is Form pTSA-$A_1$, Form pTSA-$A_2$, Form pTSA-$B_2$, Form pTSA-$C_2$ or a mixture thereof. In another aspect, the crystalline form is Form pTSA-$A_1$. In an additional aspect, the crystalline form is Form pTSA-$A_2$. In yet another aspect, the crystalline form is Form pTSA-$B_2$. In still another aspect, the crystalline form is Form pTSA-$C_2$. Still another aspect of the present invention pertains to a method of treating solid tumors comprising the step of administering to a patient in need thereof a pharmaceutical composition comprising Compound I Form pTSA-$A_1$, Compound I Form pTSA-$A_2$, Compound I Form pTSA-$B_2$, Compound I Form pTSA-$C_2$ or a mixture thereof. In a further aspect, the pharmaceutical composition comprises Form pTSA-$A_1$. In another aspect, the pharmaceutical composition comprises Form pTSA-$A_2$. In still another aspect, the pharmaceutical composition comprises Form pTSA-$B_2$. In an additional aspect, the pharmaceutical composition comprises Form pTSA-$C_2$.

An additional aspect of the present invention pertains to a crystalline form of Compound I that is Form $A_0$, Form $B_0$, Form $C_0$, Form $D_0$ or a mixture thereof. In a further aspect, the crystalline form is Form $A_0$. In another aspect, the crystalline form is Form $B_0$. In still another aspect, the crystalline form is Form $C_0$. In yet another aspect, the crystalline form is Form $D_0$.

Figure 9:
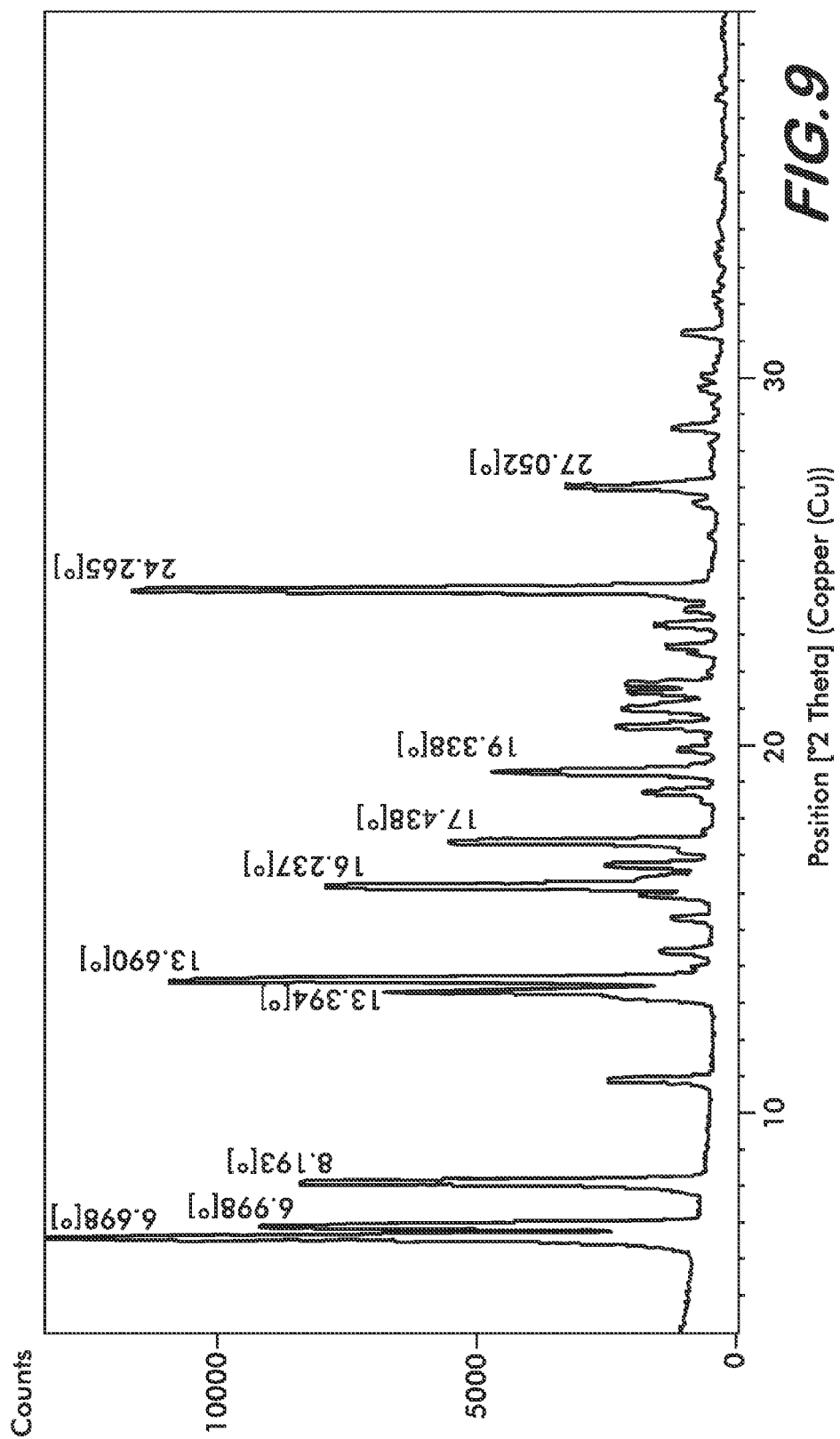
FIG. 9 is an X-ray Powder Diffractogram (XRPD) of Form $A_0$
Figure 10:
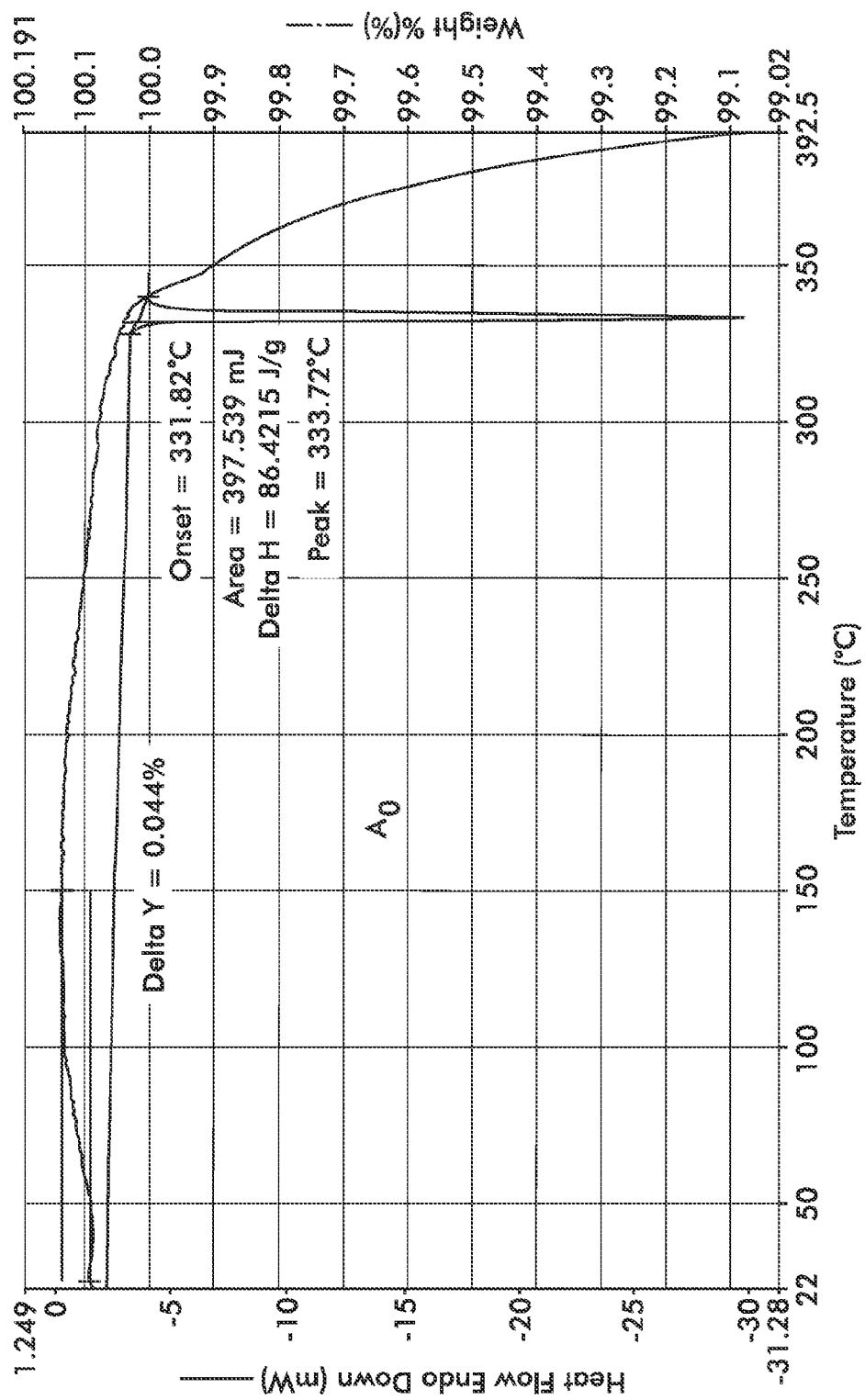
FIG. 10 is a Differential Scanning calorimetry (DSC) Thermogram and Thermo-Gravimetric Analysis (TGA) Thermogram overlay of Form $A_0$

An additional aspect of the present invention pertains to a crystalline form of Compound I that is Form $A_0$, characterized by an X-ray diffraction pattern comprising one or more of the following peaks: 6.70, 7.00, 8.19, 13.69 and/or 24.26±0.2 degrees 2-theta when measured using Cu—Kα radiation (λ=1.54056 Å). In another aspect, the X-ray diffraction pattern of crystalline Form $A_0$ comprises a peak at 6.70±0.2 degrees 2-theta and one or more of the following peaks: 7.00±0.2 degrees 2-theta, 8.19±0.2 degrees 2-theta, 13.69±0.2 degrees 2-theta and/or 24.26±0.2 degrees 2-theta when measured using Cu—Kα radiation (λ=1.54056 Å). In yet another aspect, the X-ray diffraction pattern of crystalline Form $A_0$ comprises peaks at 6.70±0.2 degrees 2-theta and 24.26±0.2 degrees 2-theta and one or more of the following peaks: 7.00±0.2 degrees 2-theta, 8.19±0.2 degrees 2-theta, and/or 13.69±0.2 degrees 2-theta when measured using Cu—Kα radiation (λ=1.54056 Å). In another aspect, the X-ray diffraction pattern of crystalline Form $A_0$ comprises peaks at 6.70±0.2 degrees 2-theta, 24.26±0.2 degrees 2-theta, and 13.69±0.2 degrees 2-theta and one or more of the following peaks: 7.00±0.2 degrees 2-theta and/or 8.19±0.2 degrees 2-theta when measured using Cu—Kα radiation (λ=1.54056 Å). In yet another aspect, the X-ray diffraction pattern of crystalline Form $A_0$ comprises peaks at 6.70±0.2 degrees 2-theta, 7.00±0.2 degrees 2-theta, 8.19±0.2 degrees 2-theta, 13.69±0.2 degrees 2-theta and 24.26±0.2 degrees 2-theta when measured using Cu—Kα radiation (X=1.54056 Å). A further aspect pertains to a crystalline form of Compound I that is Form $A_0$, having an X-ray powder diffraction pattern substantially as depicted in FIG. 9.

Figure 11:
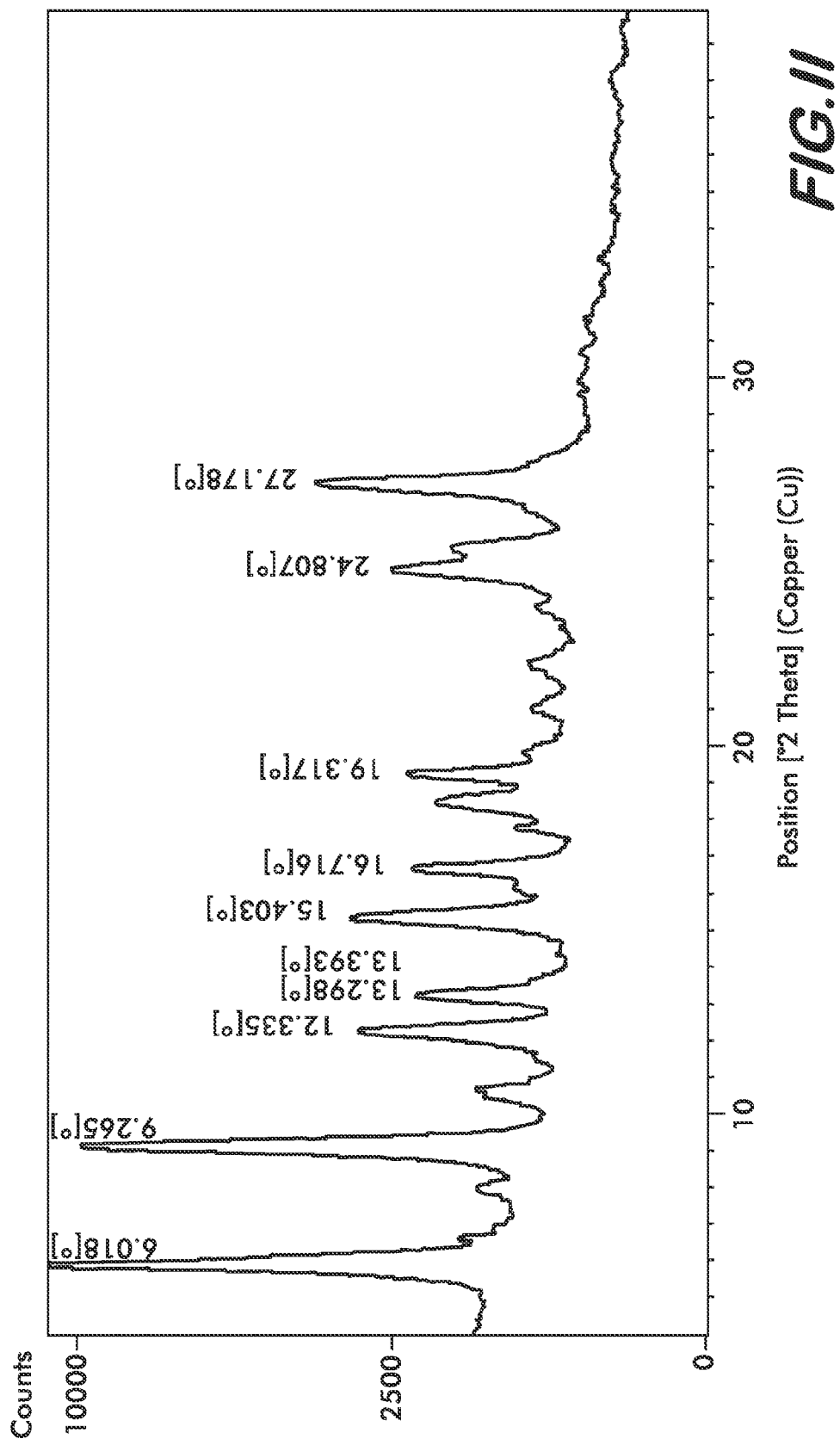
FIG. 11 is an X-ray Powder Diffractogram (XRPD) of Form $B_0$
Figure 12:
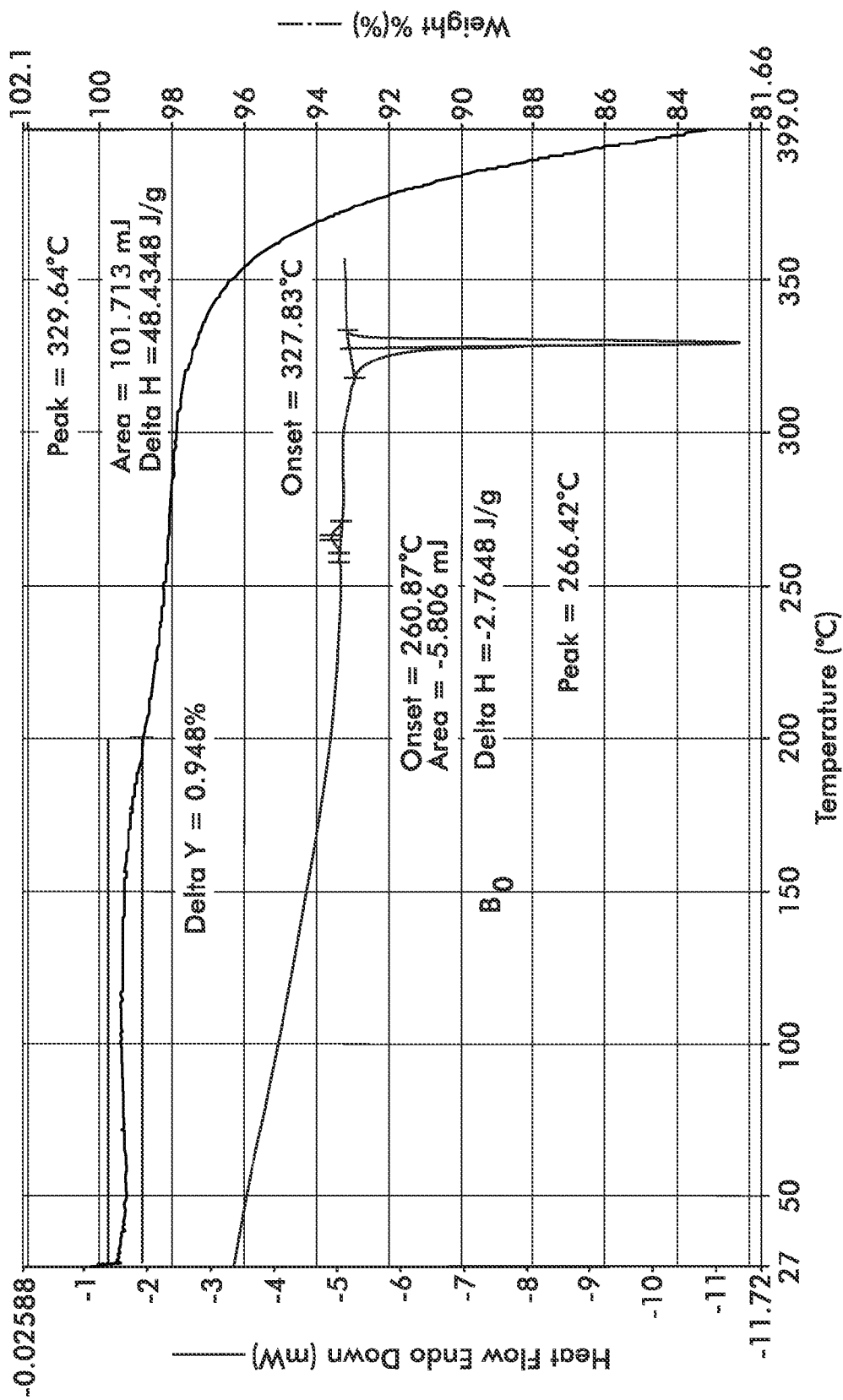
FIG. 12 is a Differential Scanning calorimetry (DSC) Thermogram and Thermo-Gravimetric Analysis (TGA) Thermogram overlay of Form $B_0$

A further aspect pertains to a crystalline form of Compound I that is Form $B_0$, characterized by an X-ray powder diffraction pattern comprising one or more of the following peaks: 6.02, 9.27, 12.34, 15.40 and/or 27.18±0.2 degrees 2-theta. Another aspect pertains to a crystalline form of Compound I that is Form $B_0$, having an X-ray powder diffraction pattern substantially as depicted in FIG. 11.

Figure 13:
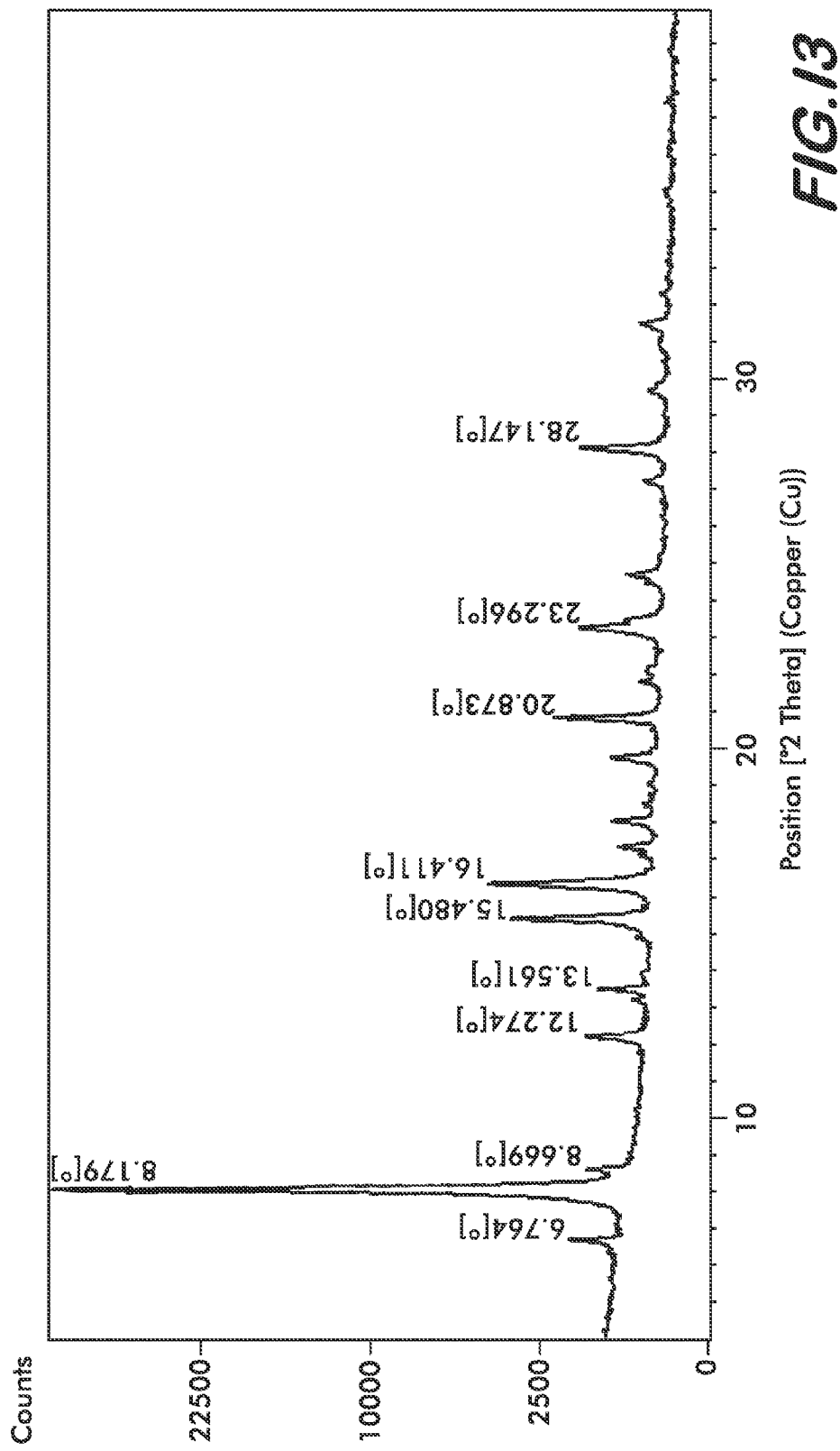
FIG. 13 is an X-ray Powder Diffractogram (XRPD) of Form $C_0$
Figure 14:
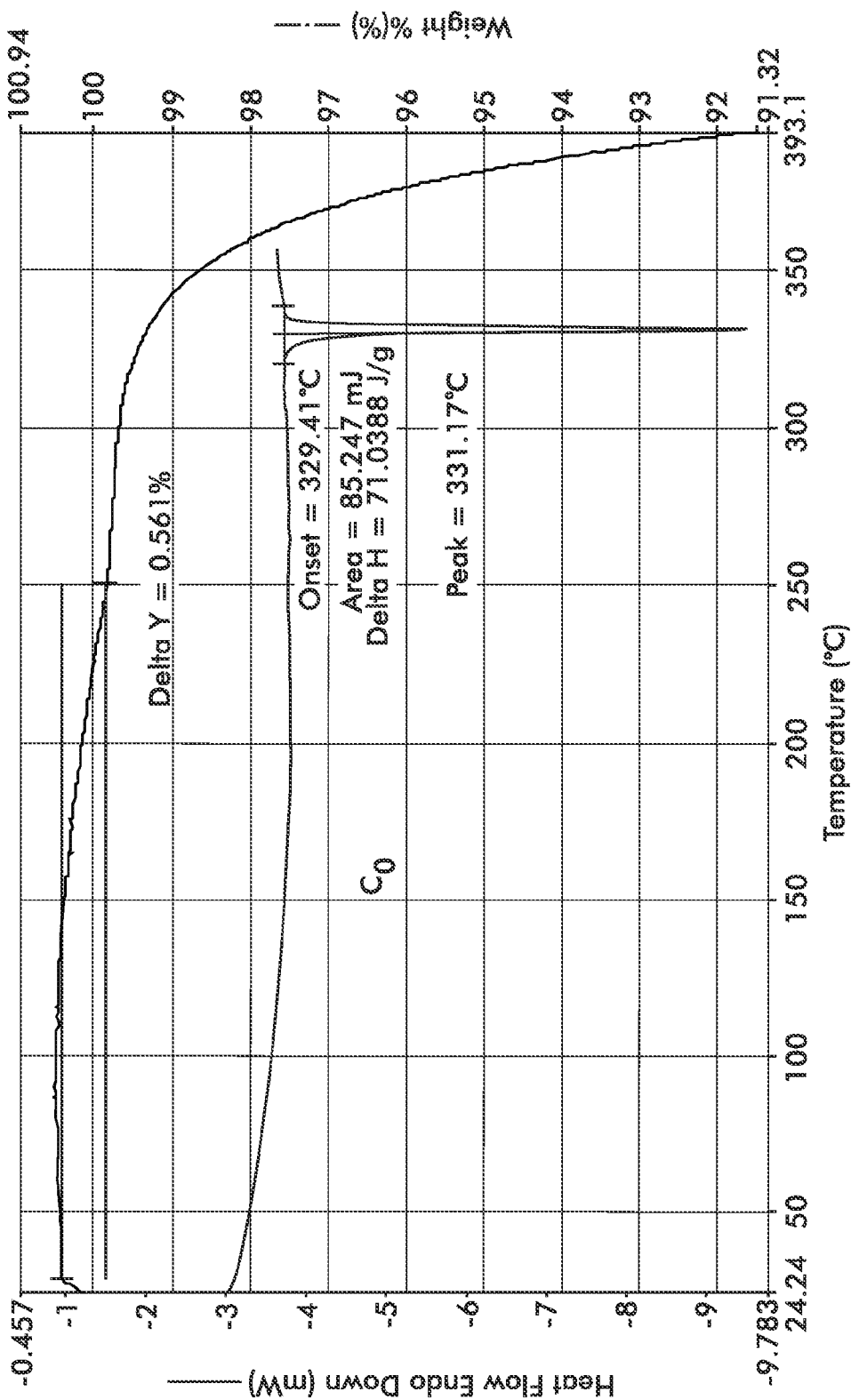
FIG. 14 is a Differential Scanning calorimetry (DSC) Thermogram and Thermo-Gravimetric Analysis (TGA) Thermogram overlay of Form $C_0$

Still another aspect of the present invention pertains to a crystalline form of Compound I that is Form $C_0$, characterized by an X-ray powder diffraction pattern comprising one or more of the following peaks: 8.18, 15.48, 16.41, and/or 20.87±0.2 degrees 2-theta. A further aspect pertains to a crystalline form of Compound I that is Form $C_0$, having an X-ray powder diffraction pattern substantially as depicted in FIG. 13.

Figure 15:
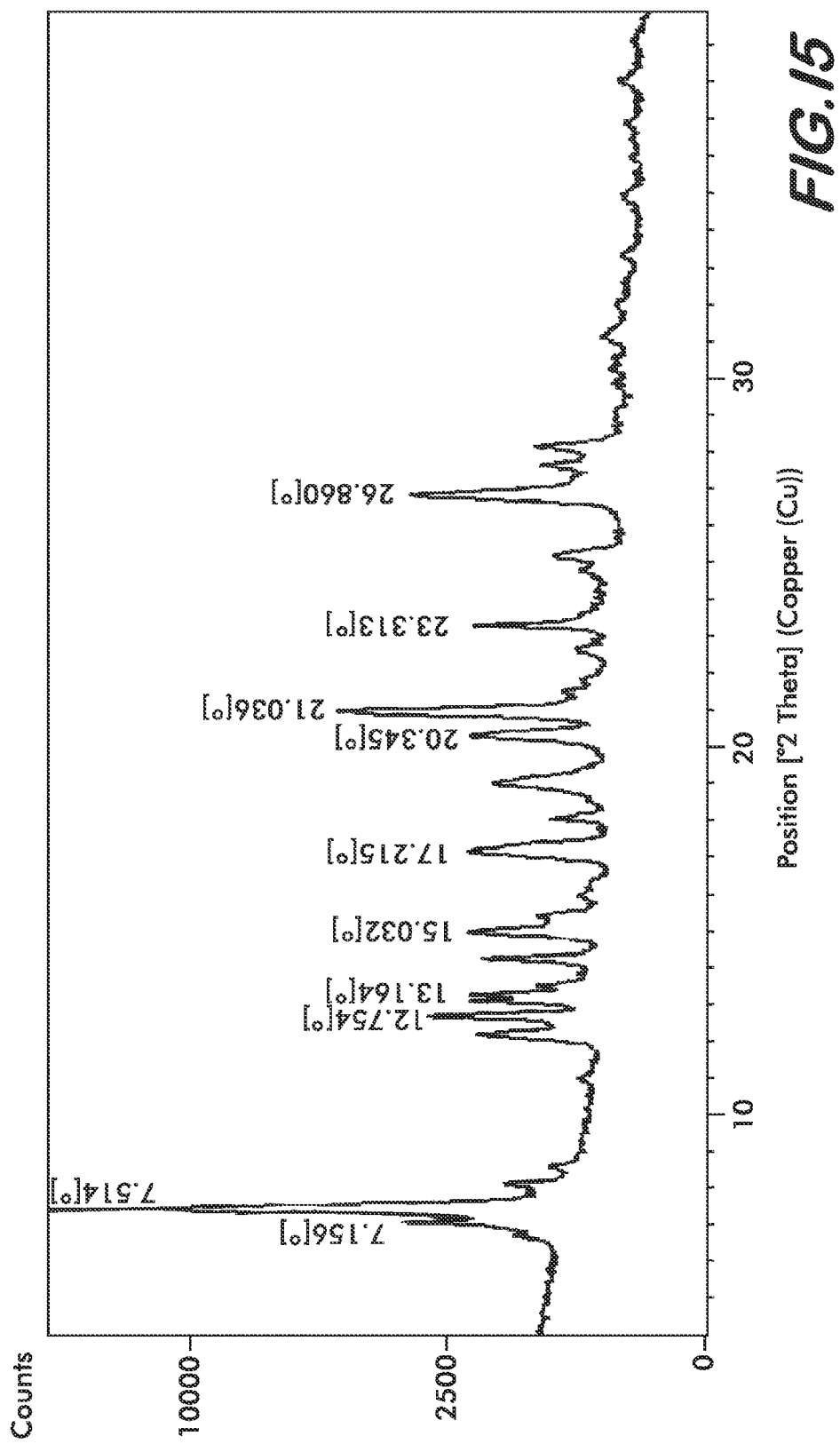
FIG. 15 is an X-ray Powder Diffractogram (XRPD) of Form $D_0$
Figure 16:
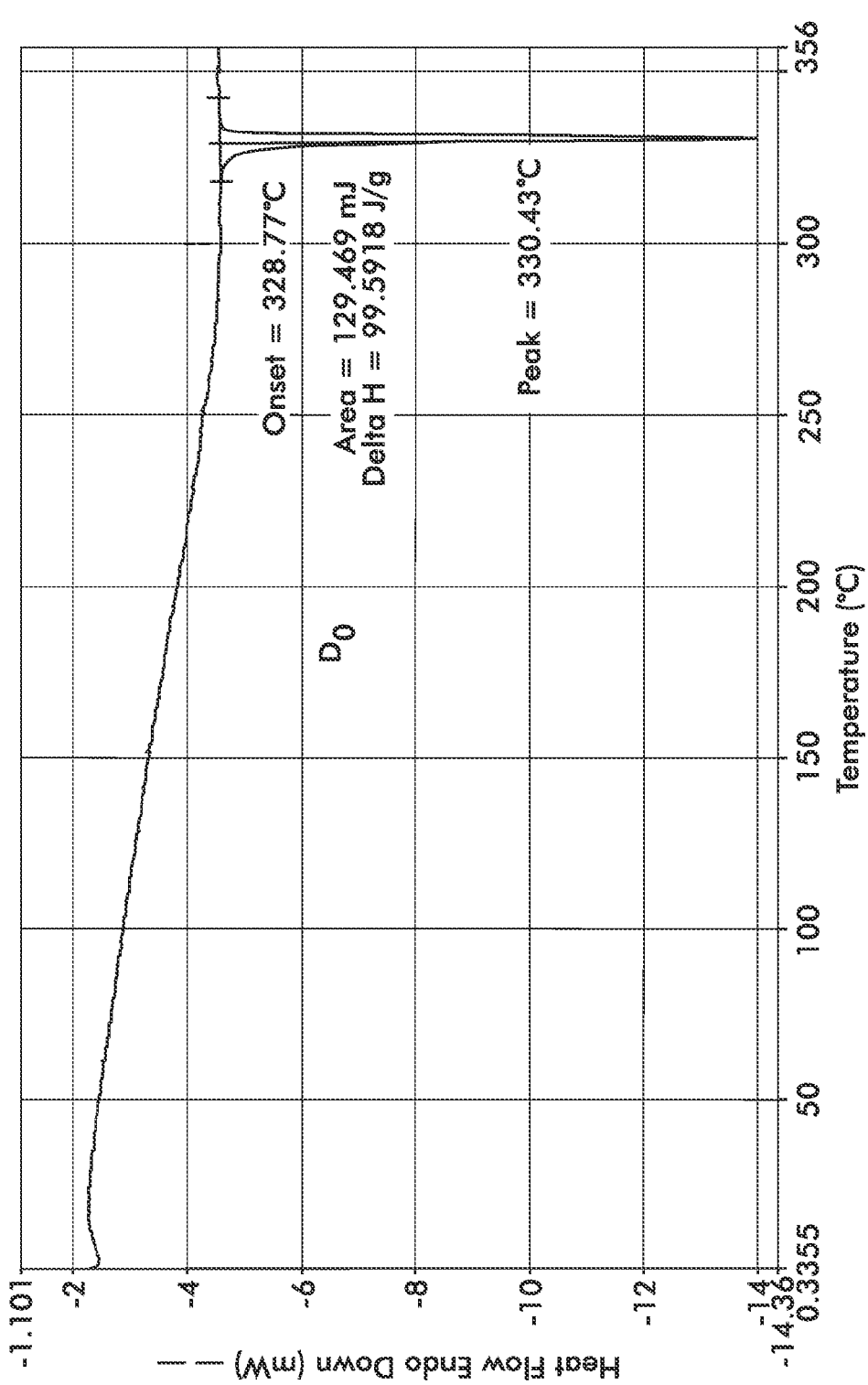
FIG. 16 is a Differential Scanning calorimetry (DSC) Thermogram and Thermo-Gravimetric Analysis (TGA) Thermogram overlay of Form $D_0$
Figure 17:
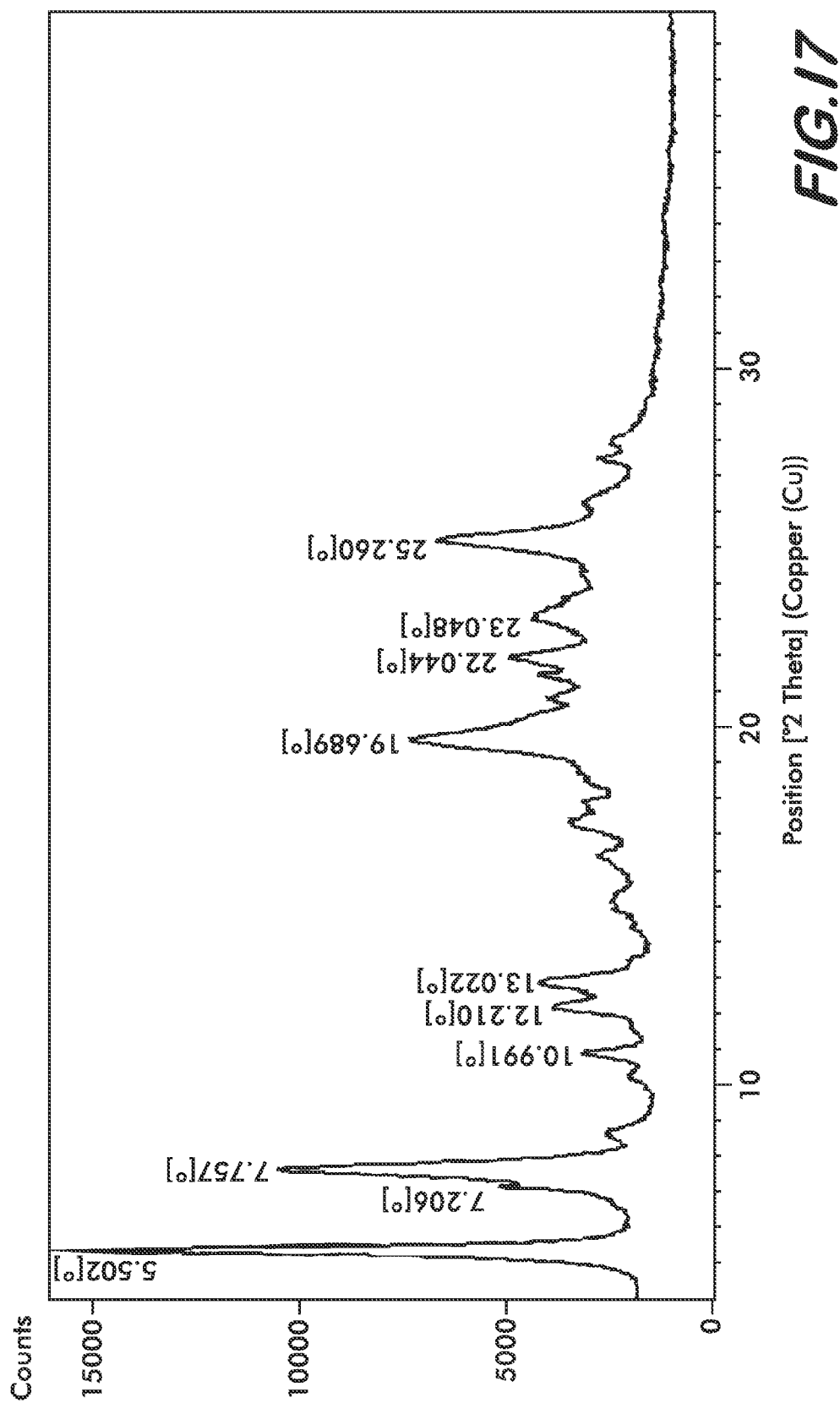
FIG. 17 is an X-ray Powder Diffractogram (XRPD) of Form $S_1$
Figure 18:
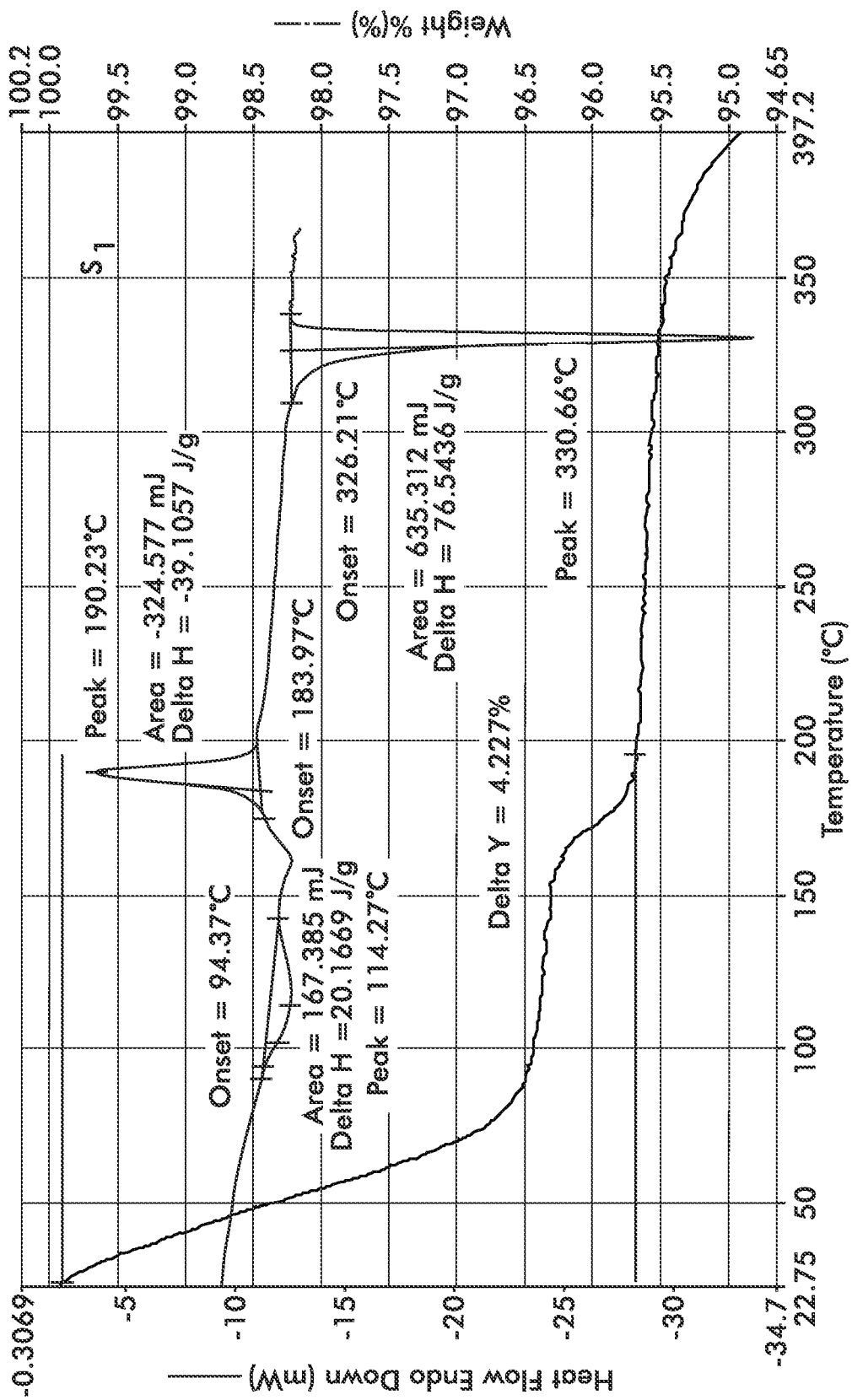
FIG. 18 is a Differential Scanning calorimetry (DSC) Thermogram and Thermo-Gravimetric Analysis (TGA) Thermogram overlay of Form $S_1$
Figure 19:
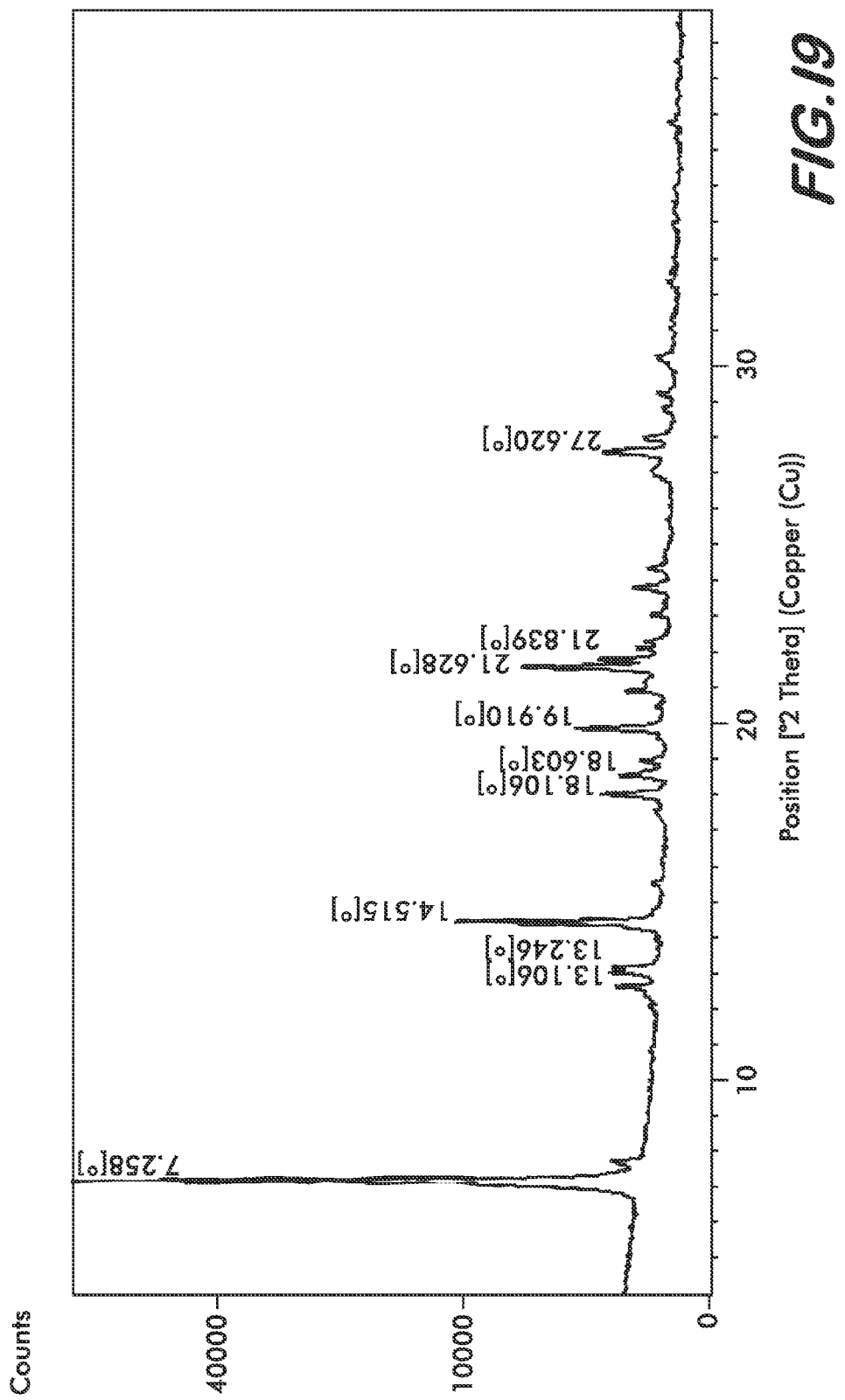
FIG. 19 is an X-ray Powder Diffractogram (XRPD) of Form $S_2$
Figure 20:
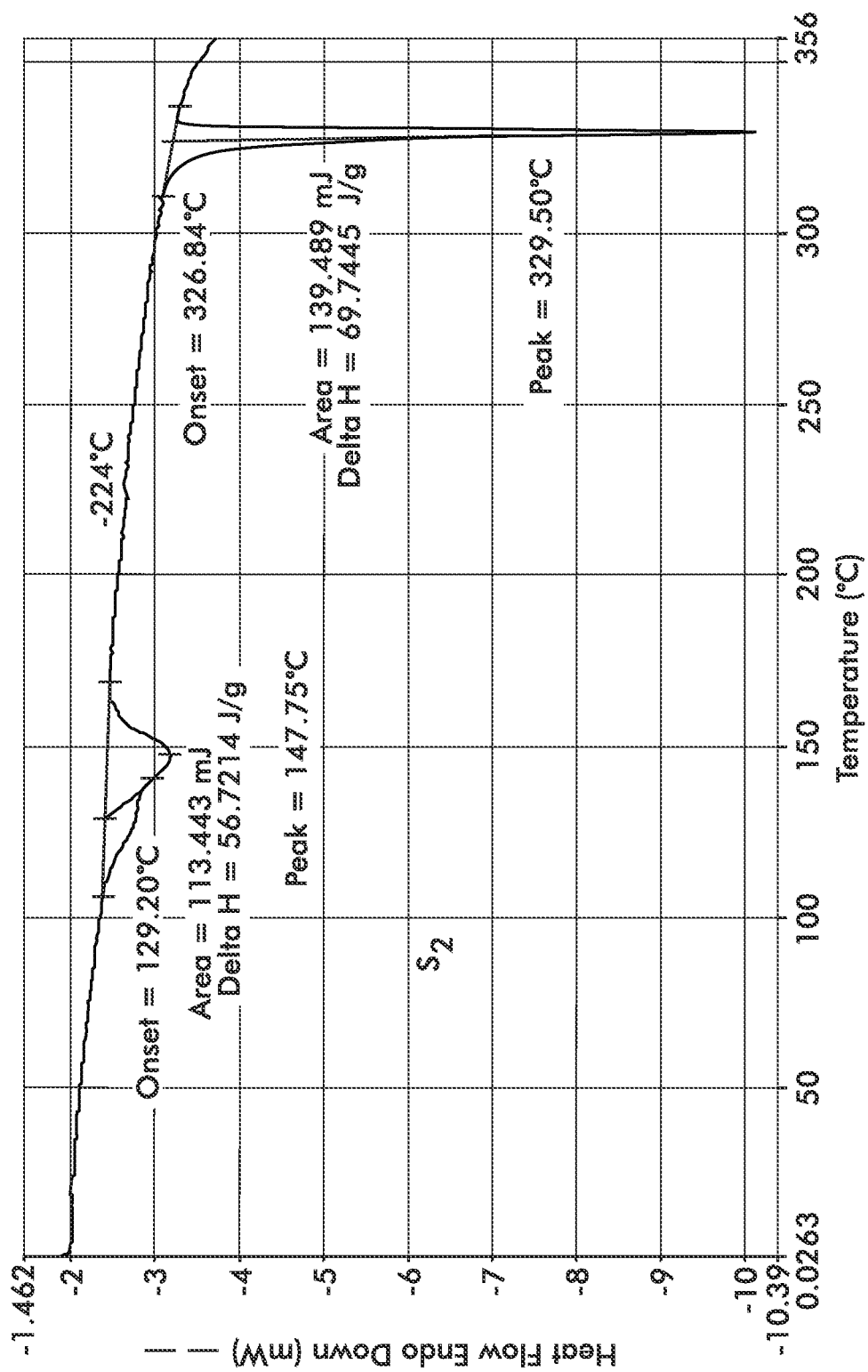
FIG. 20 is a Differential Scanning calorimetry (DSC) Thermogram of Form $S_2$
Figure 21:
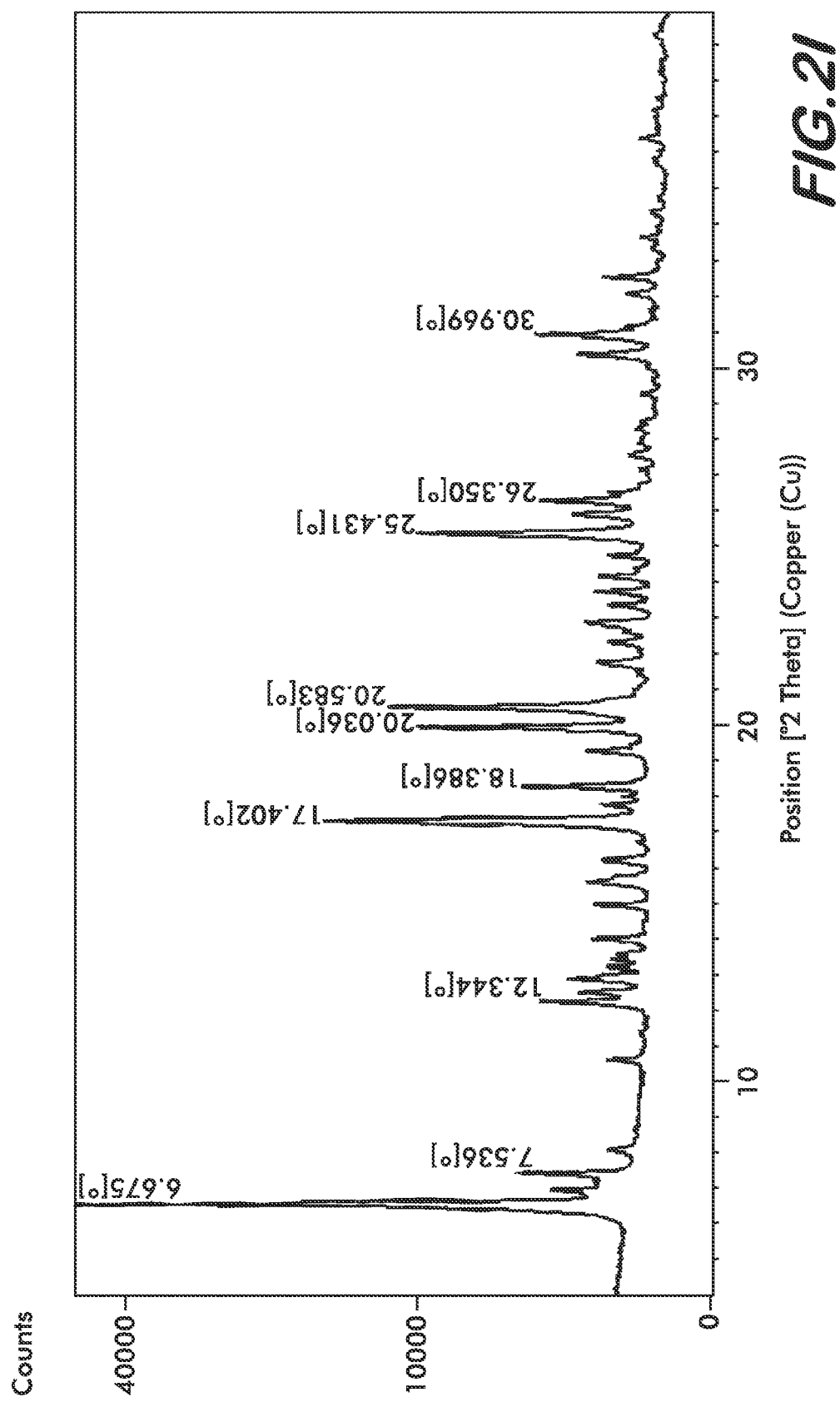
FIG. 21 is an X-ray Powder Diffractogram (XRPD) of Form $S_3$
Figure 22:
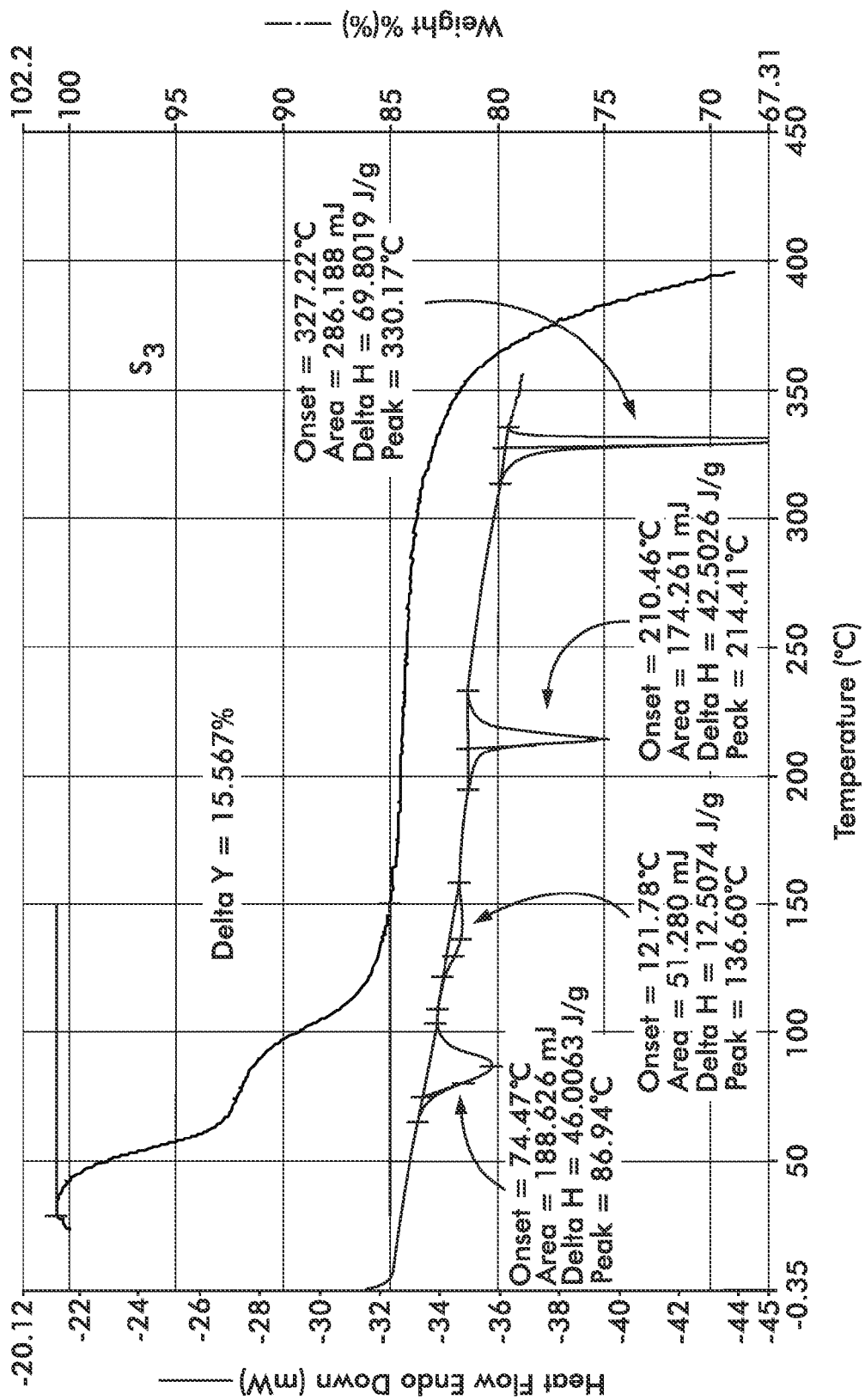
FIG. 22 is a Differential Scanning calorimetry (DSC) Thermogram and Thermo-Gravimetric Analysis (TGA) Thermogram overlay of Form $S_3$
Figure 23:
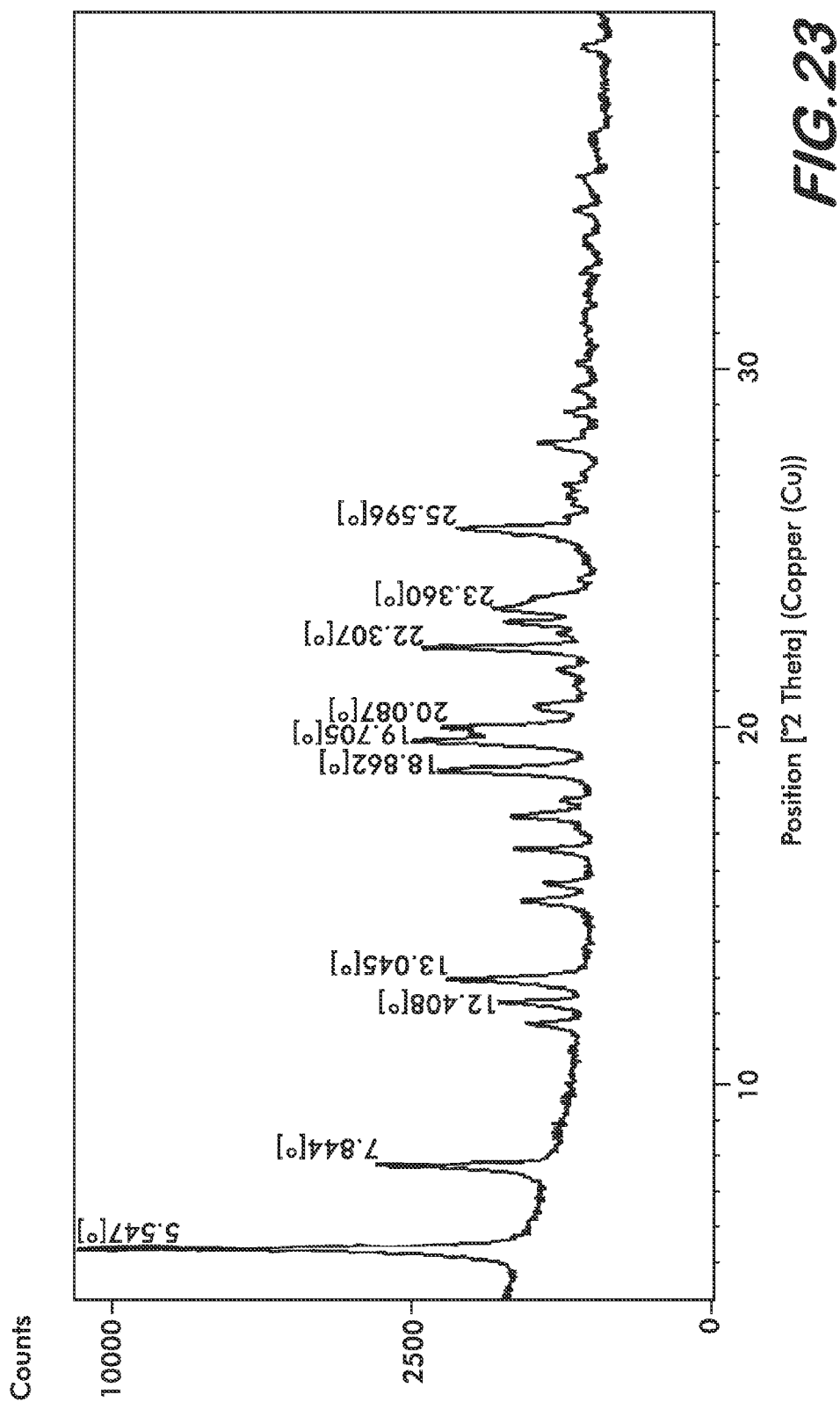
FIG. 23 is an X-ray Powder Diffractogram (XRPD) of Form $S_4$
Figure 24:
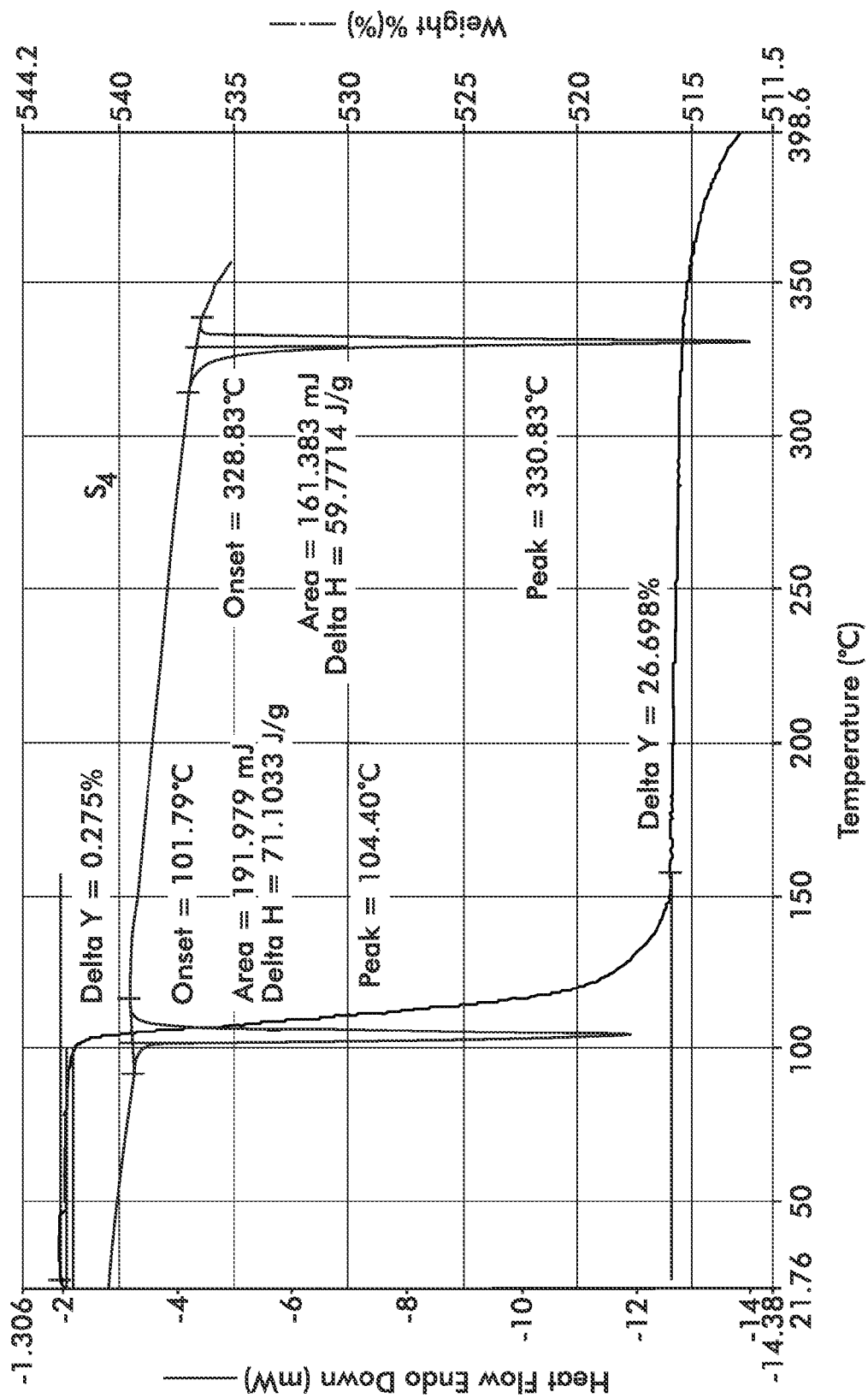
FIG. 24 is a Differential Scanning calorimetry (DSC) Thermogram and Thermo-Gravimetric Analysis (TGA) Thermogram overlay of Form $S_4$
Figure 25:
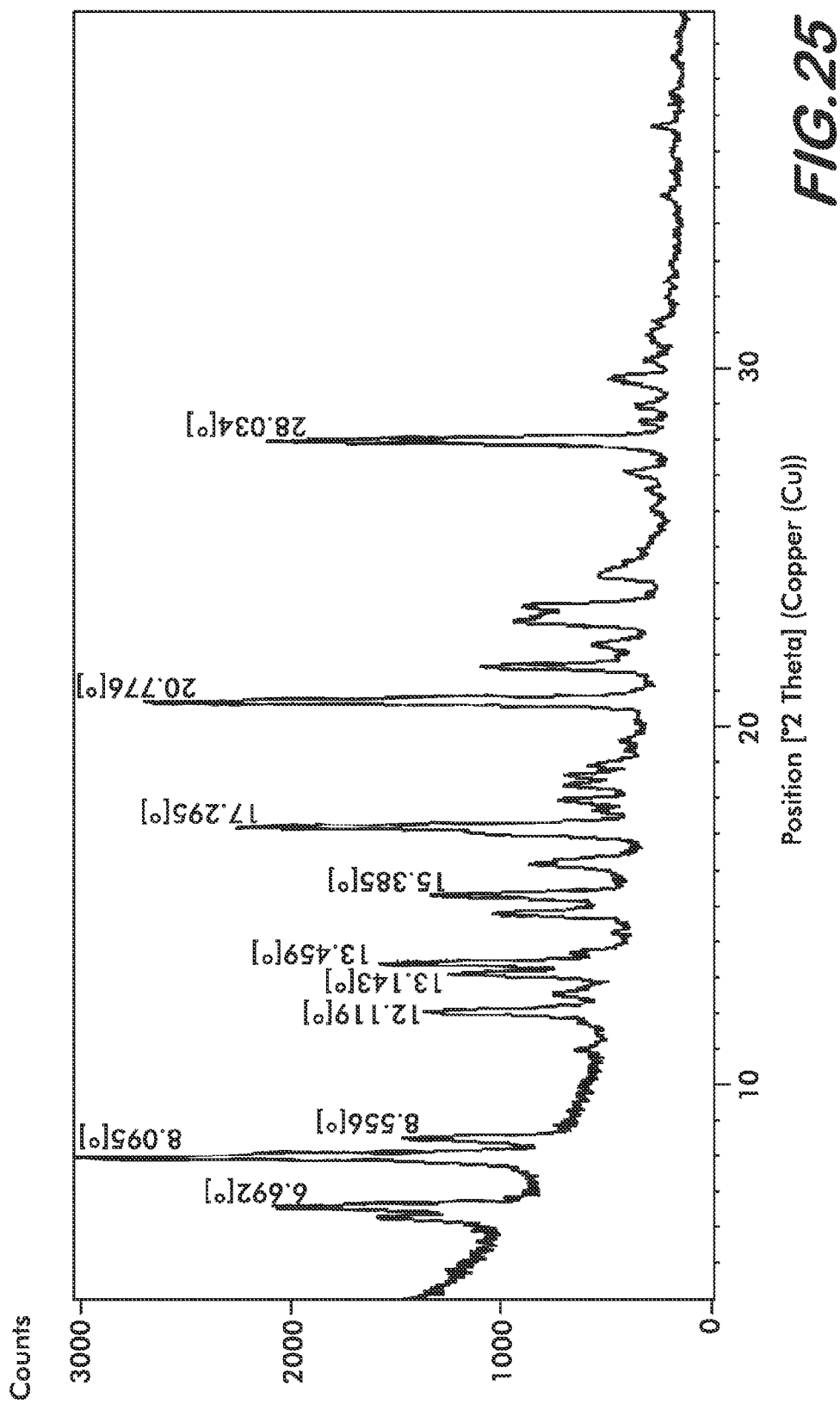
FIG. 25 is an X-ray Powder Diffractogram (XRPD) of Form $S_6$
Figure 26:
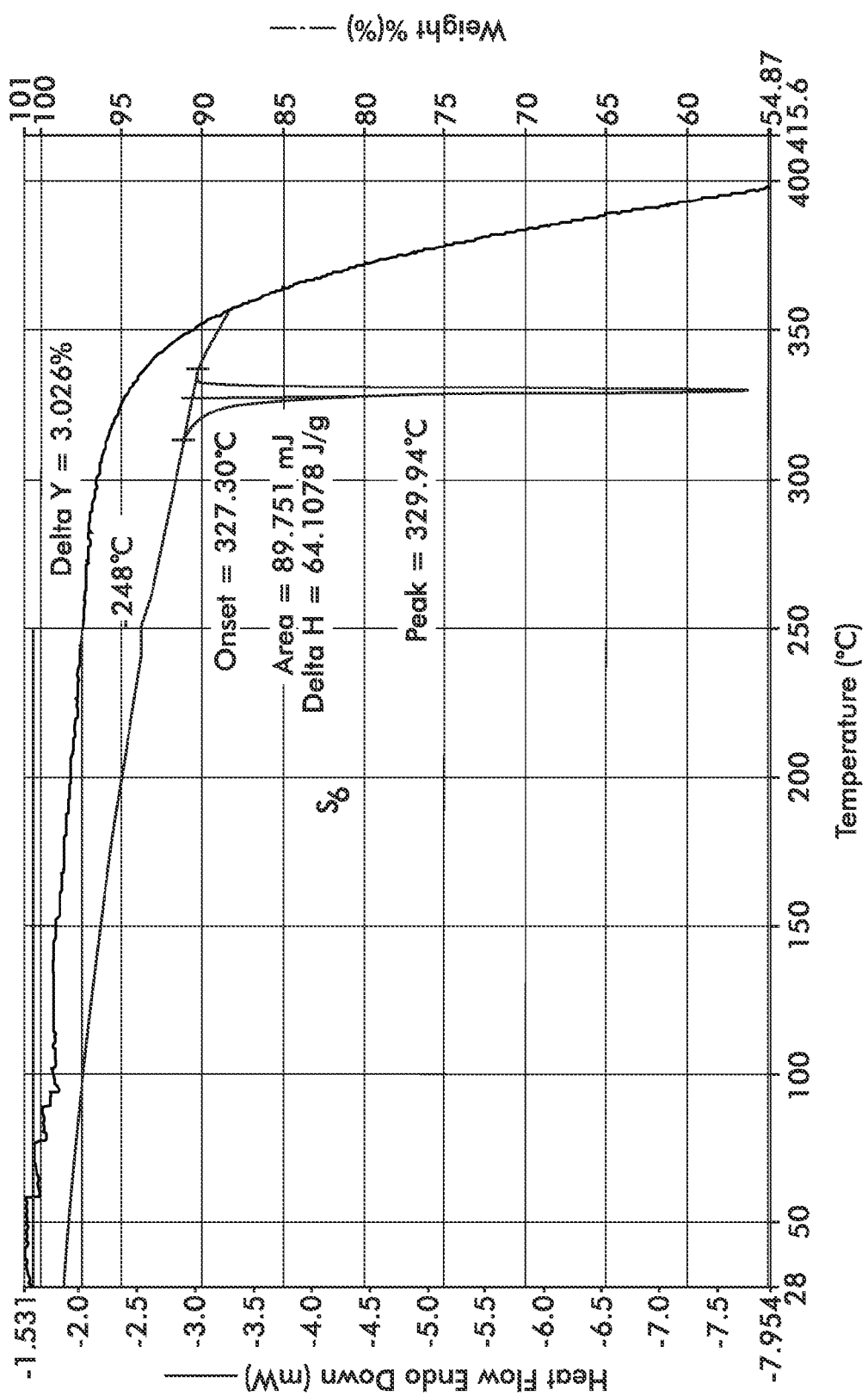
FIG. 26 is a Differential Scanning calorimetry (DSC) Thermogram and Thermo-Gravimetric Analysis (TGA) Thermogram overlay of Form $S_6$
Figure 27:
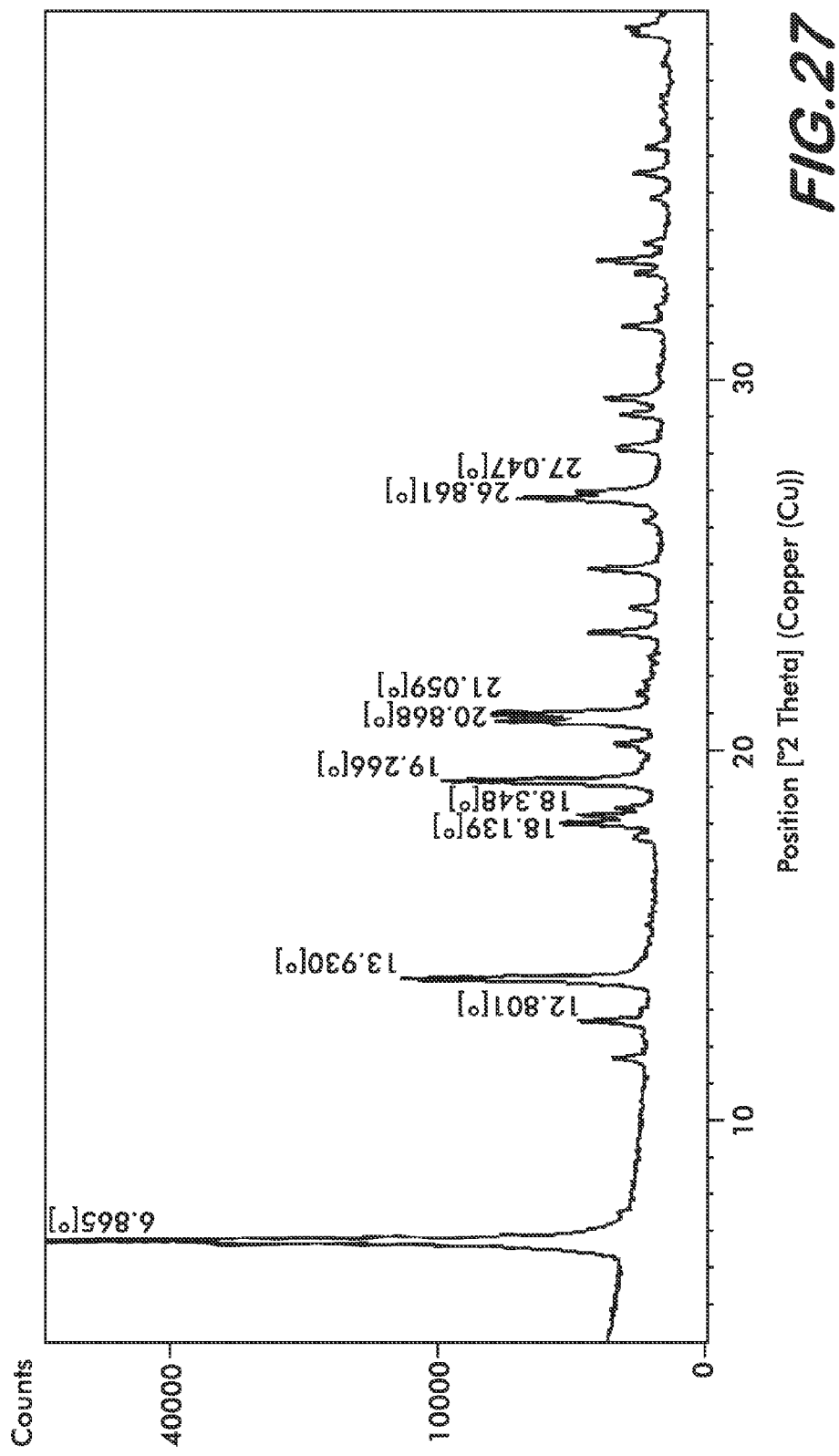
FIG. 27 is an X-ray Powder Diffractogram (XRPD) of Form $S_7$
Figure 28:
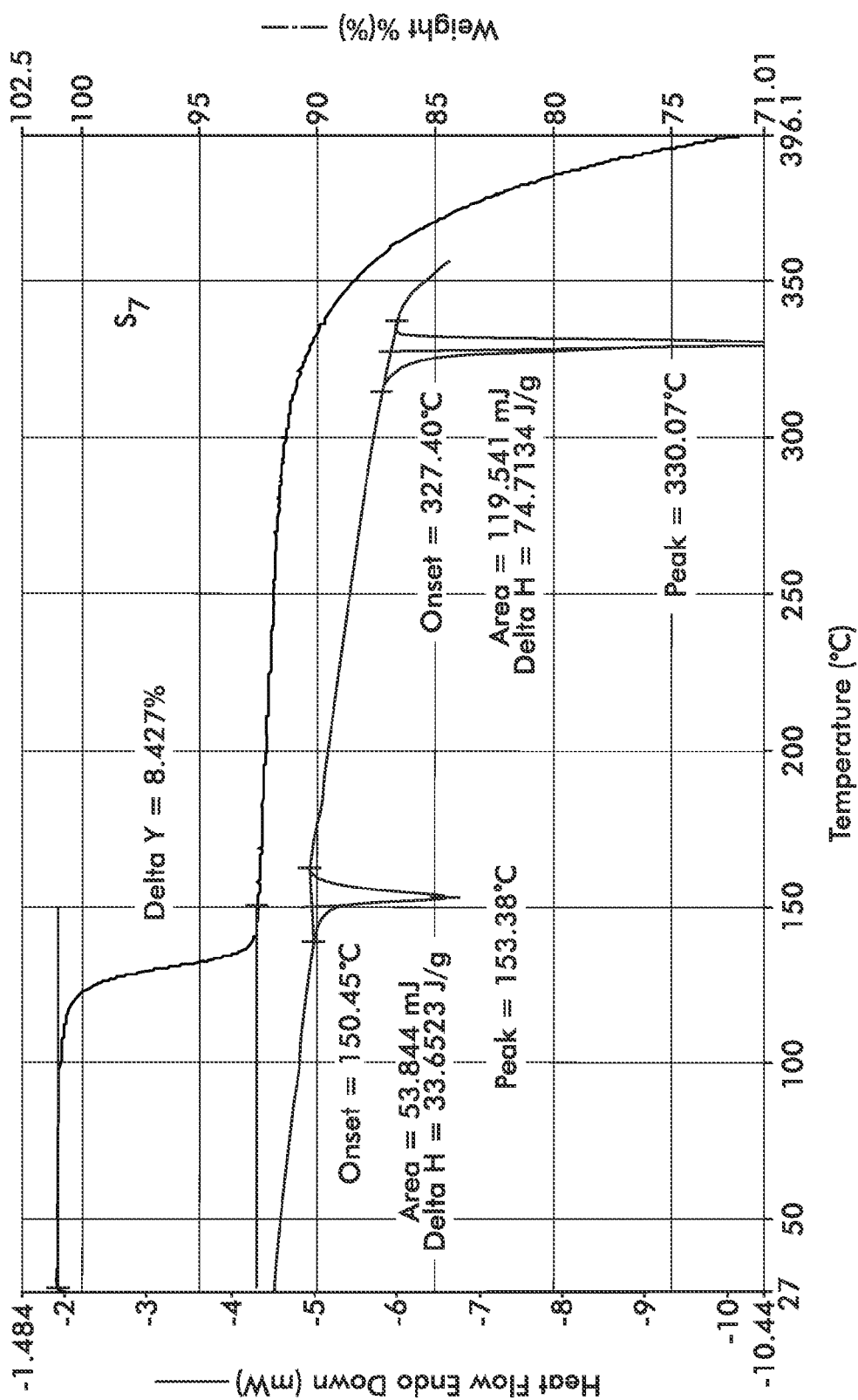
FIG. 28 is a Differential Scanning calorimetry (DSC) Thermogram and Thermo-Gravimetric Analysis (TGA) Thermogram overlay of Form $S_7$
Figure 29:
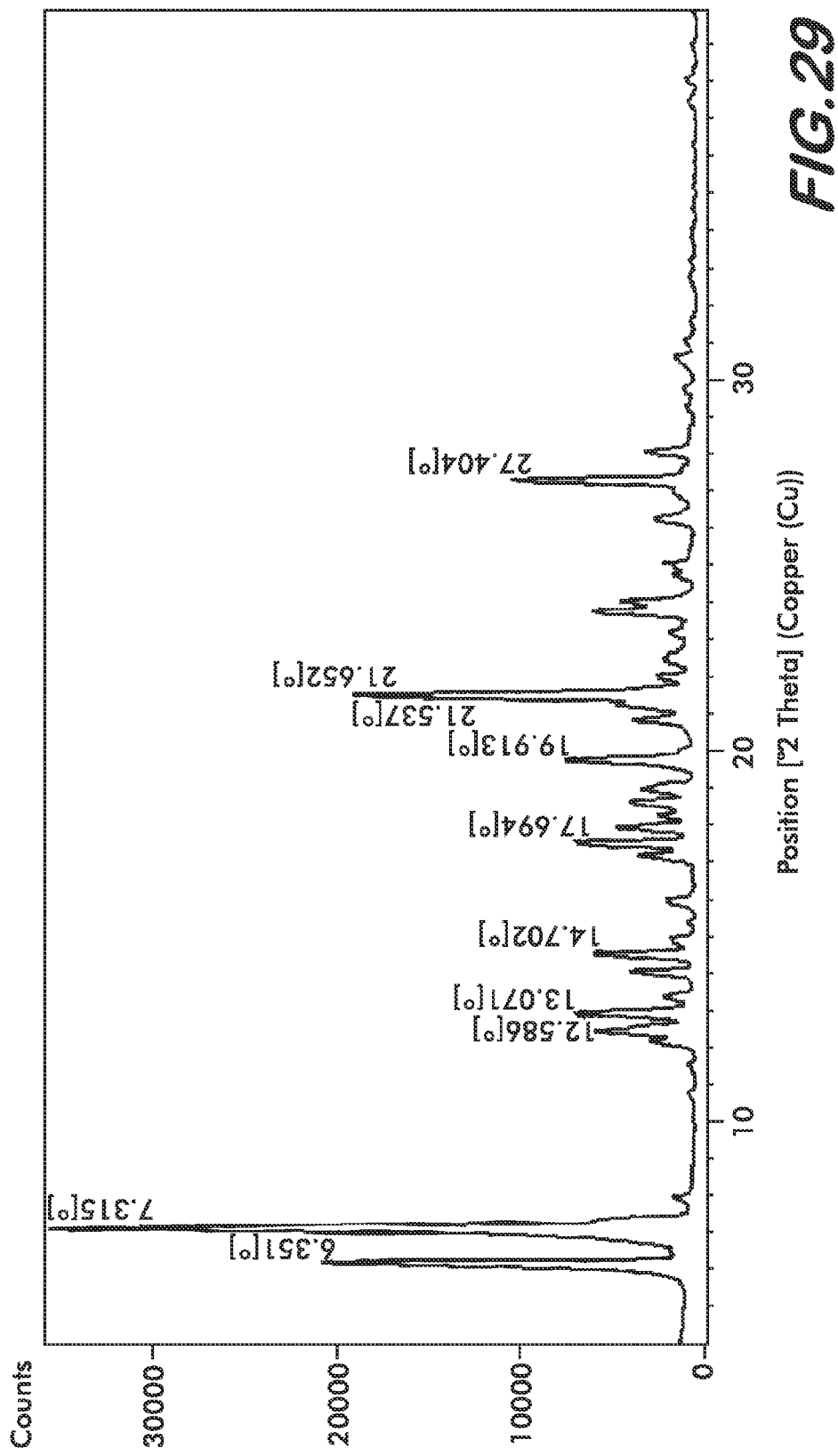
FIG. 29 is an X-ray Powder Diffractogram (XRPD) of Form $S_8$
Figure 30:
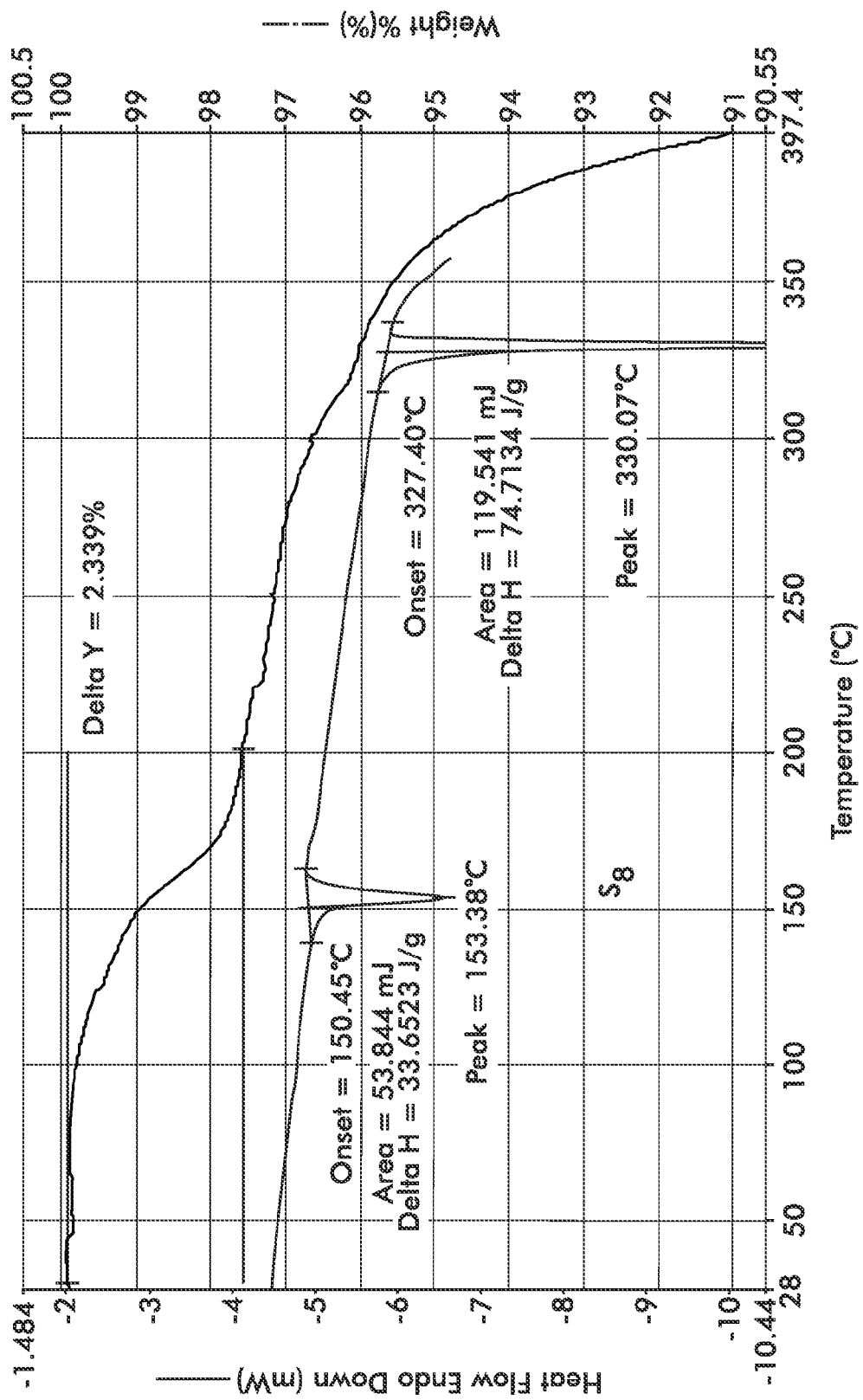
FIG. 30 is a Differential Scanning calorimetry (DSC) Thermogram and Thermo-Gravimetric Analysis (TGA) Thermogram overlay of Form $S_8$
Figure 31:
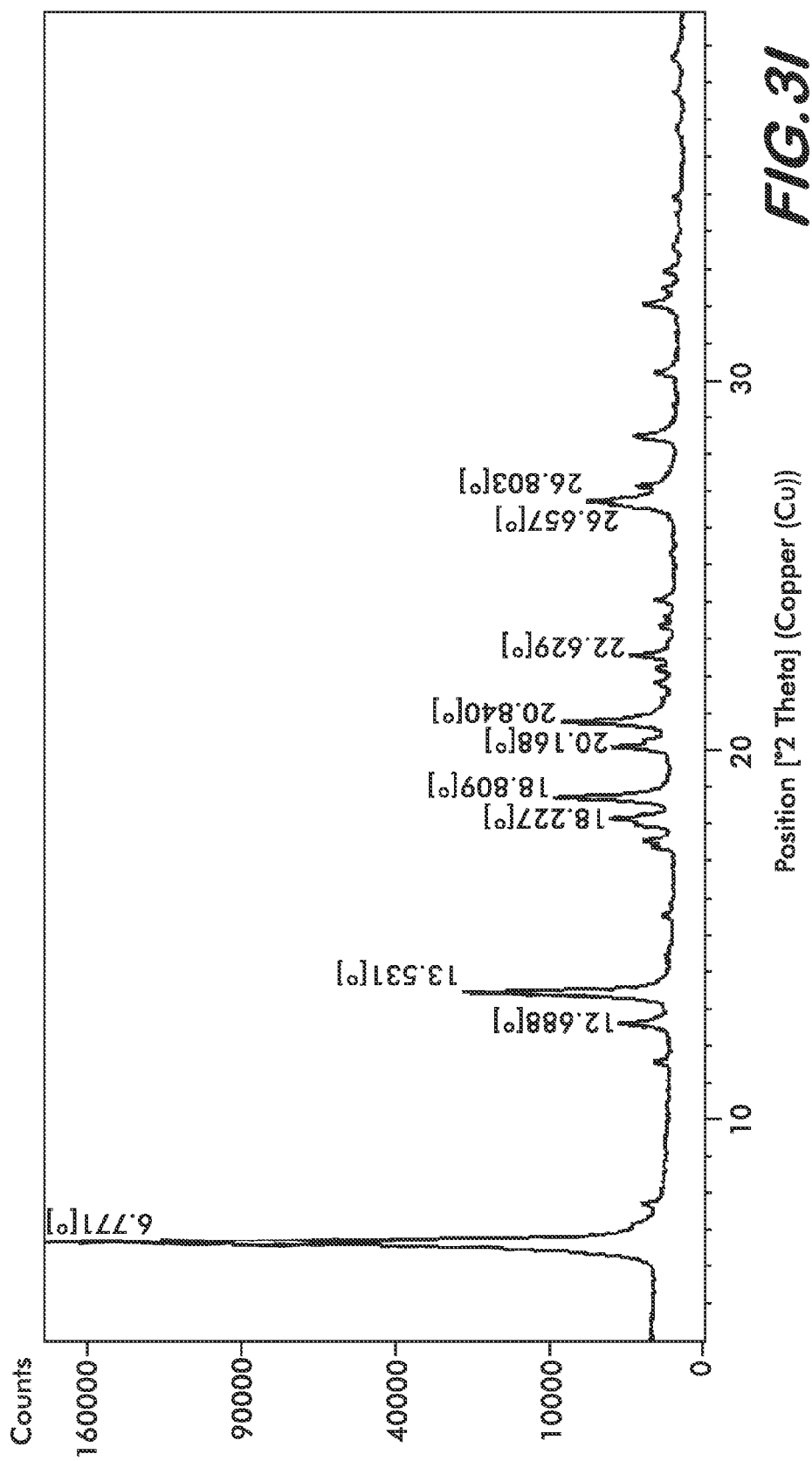
FIG. 31 is an X-ray Powder Diffractogram (XRPD) of Form $S_9$
Figure 32:
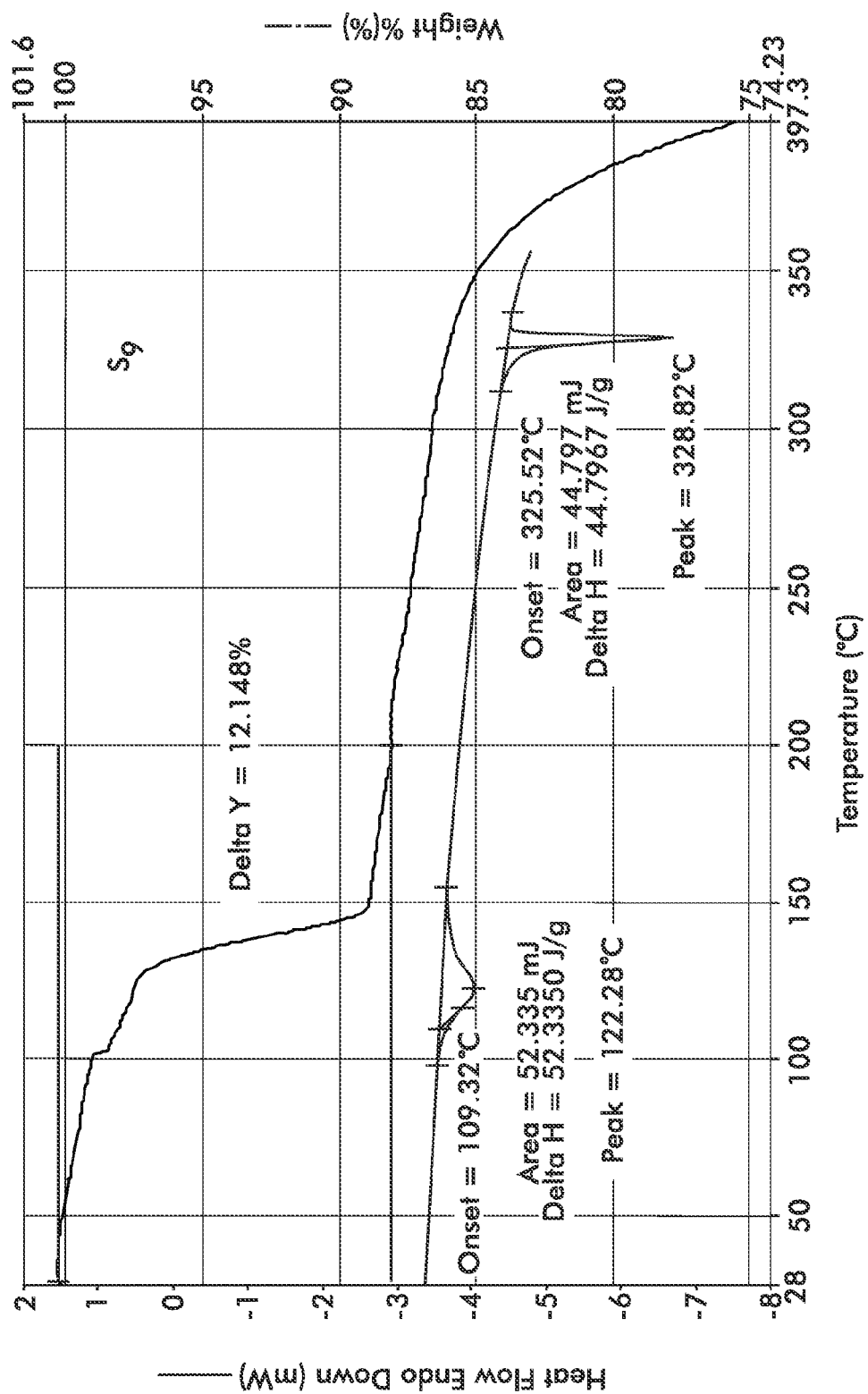
FIG. 32 is a Differential Scanning calorimetry (DSC) Thermogram and Thermo-Gravimetric Analysis (TGA) Thermogram overlay of Form $S_9$
Figure 33:
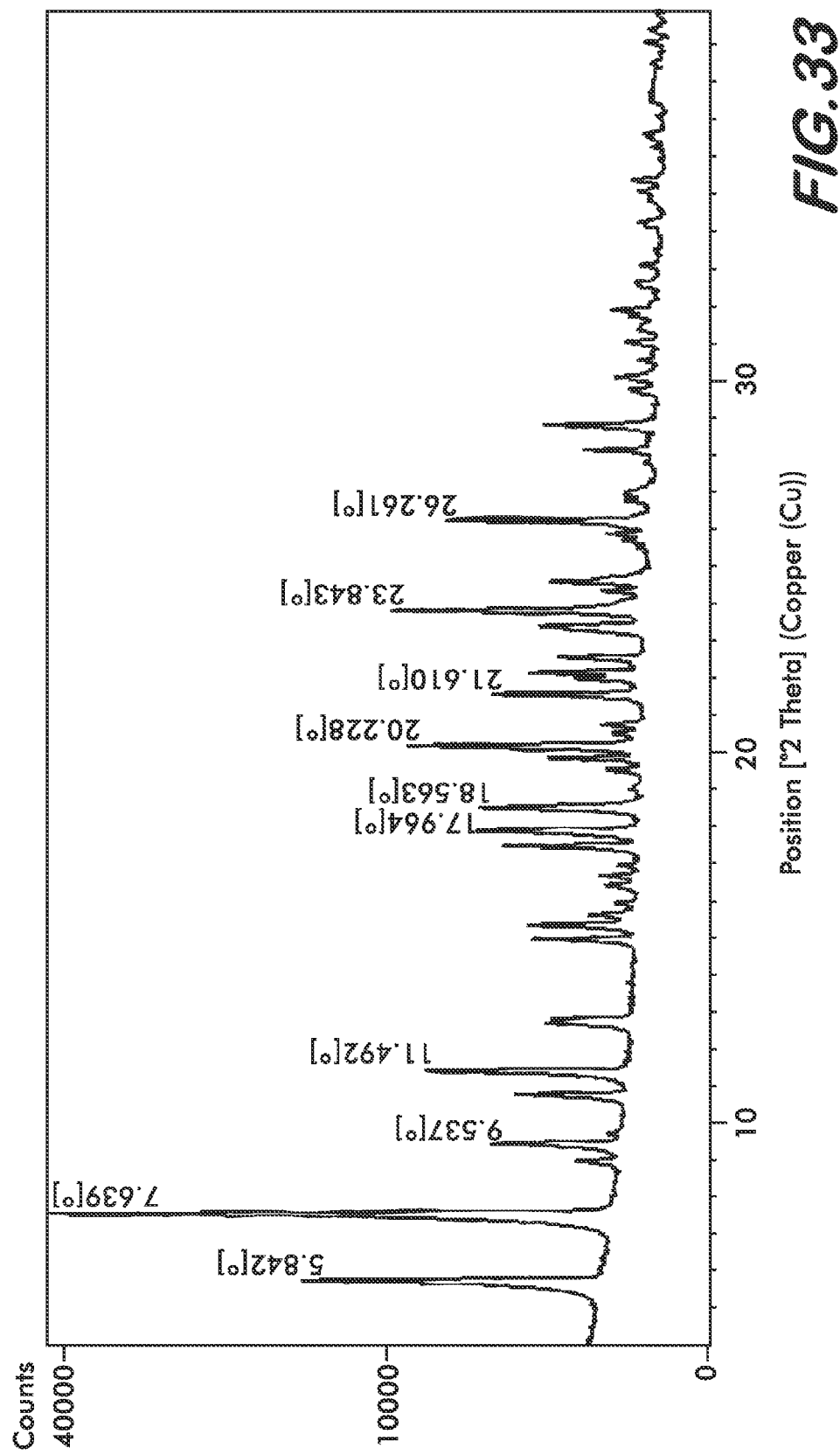
FIG. 33 is an X-ray Powder Diffractogram (XRPD) of Form $S_{10}$
Figure 34:
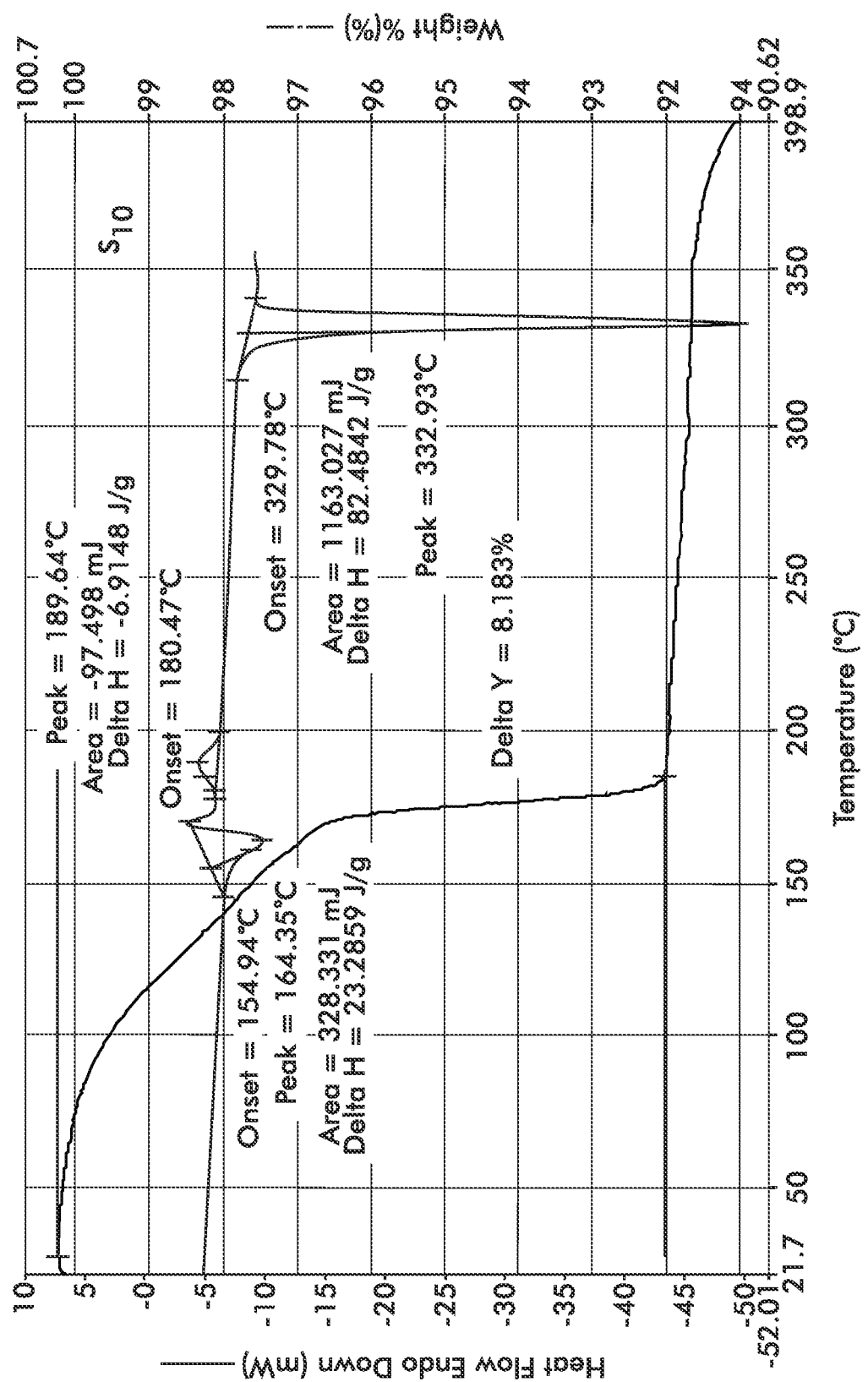
FIG. 34 is a Differential Scanning calorimetry (DSC) Thermogram and Thermo-Gravimetric Analysis (TGA) Thermogram overlay of Form $S_{10}$
Figure 35:
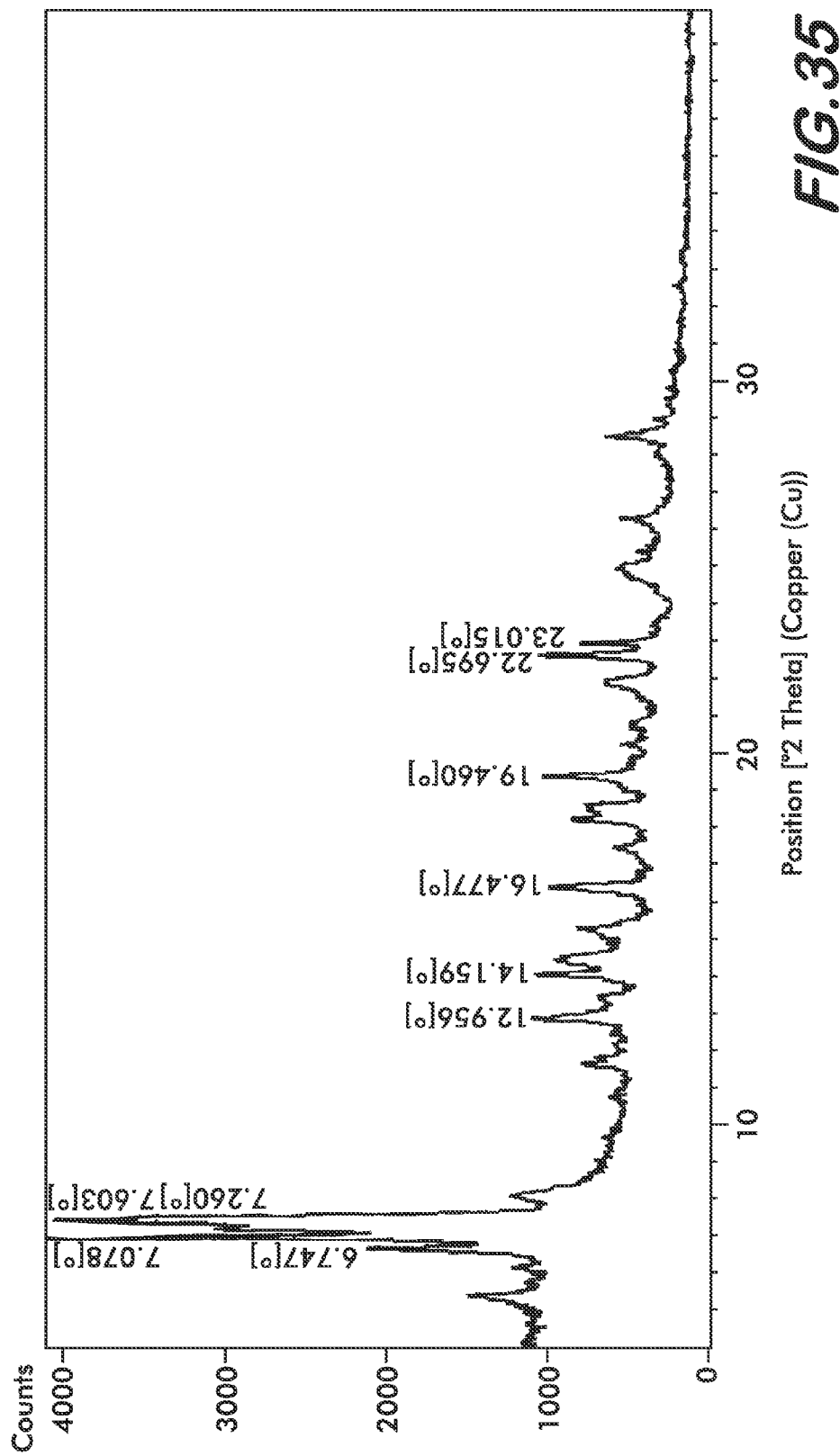
FIG. 35 is an X-ray Powder Diffractogram (XRPD) of Form $S_{13}$
Figure 36:
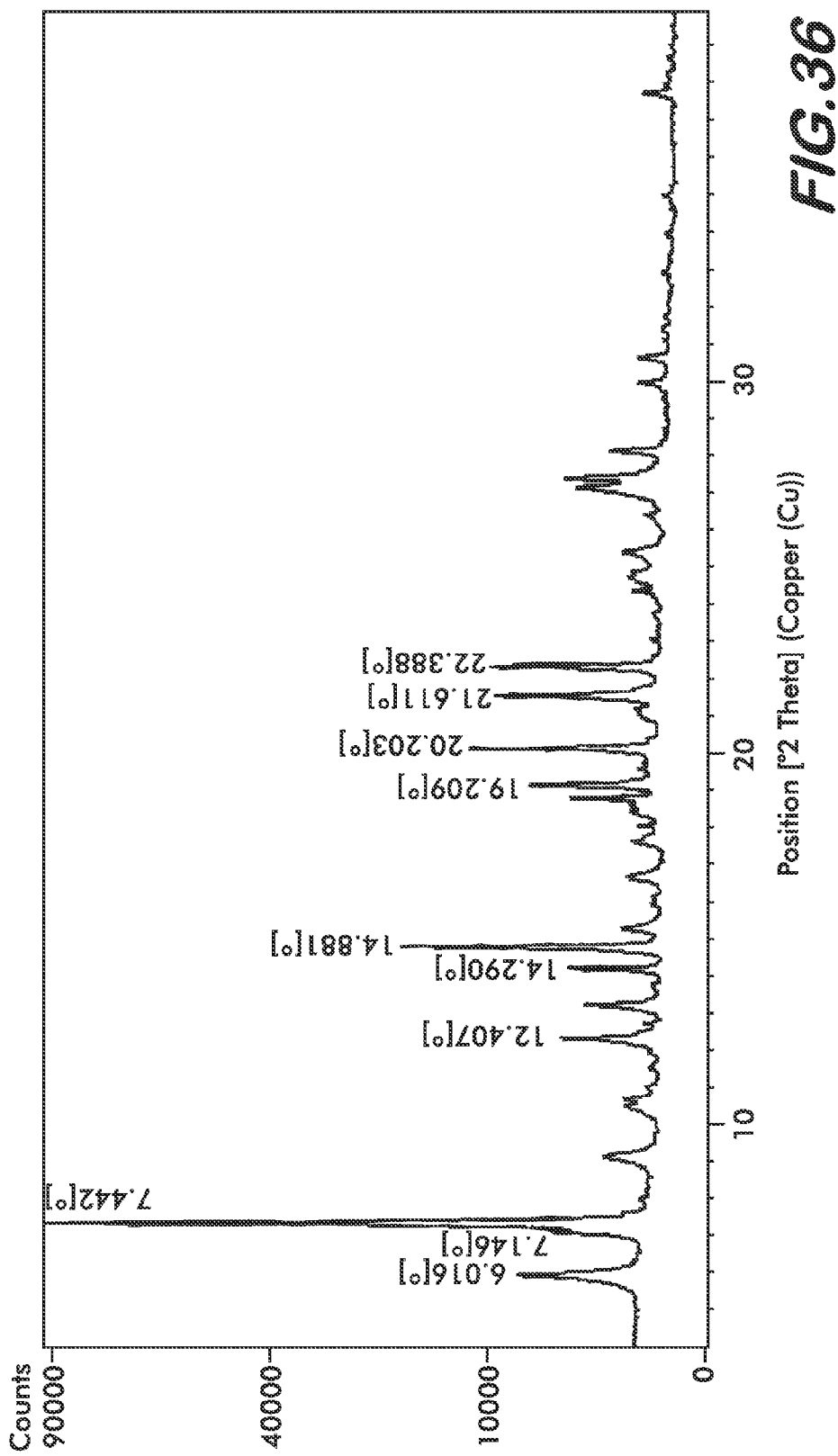
FIG. 36 is an X-ray Powder Diffractogram (XRPD) of Form $S_{14}$
Figure 37:
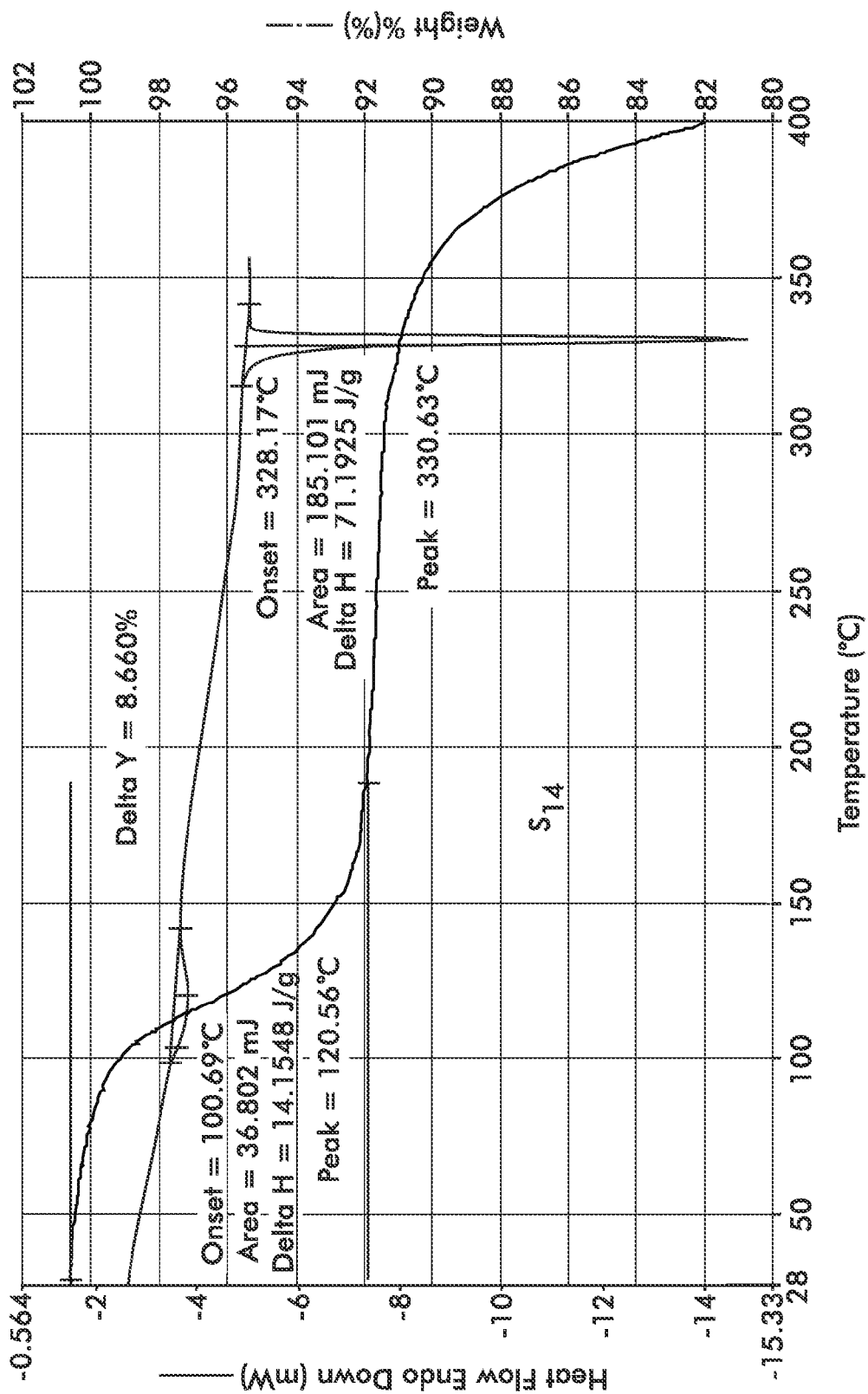
FIG. 37 is a Differential Scanning calorimetry (DSC) Thermogram and Thermo-Gravimetric Analysis (TGA) Thermogram overlay of Form $S_{14}$
Figure 38:
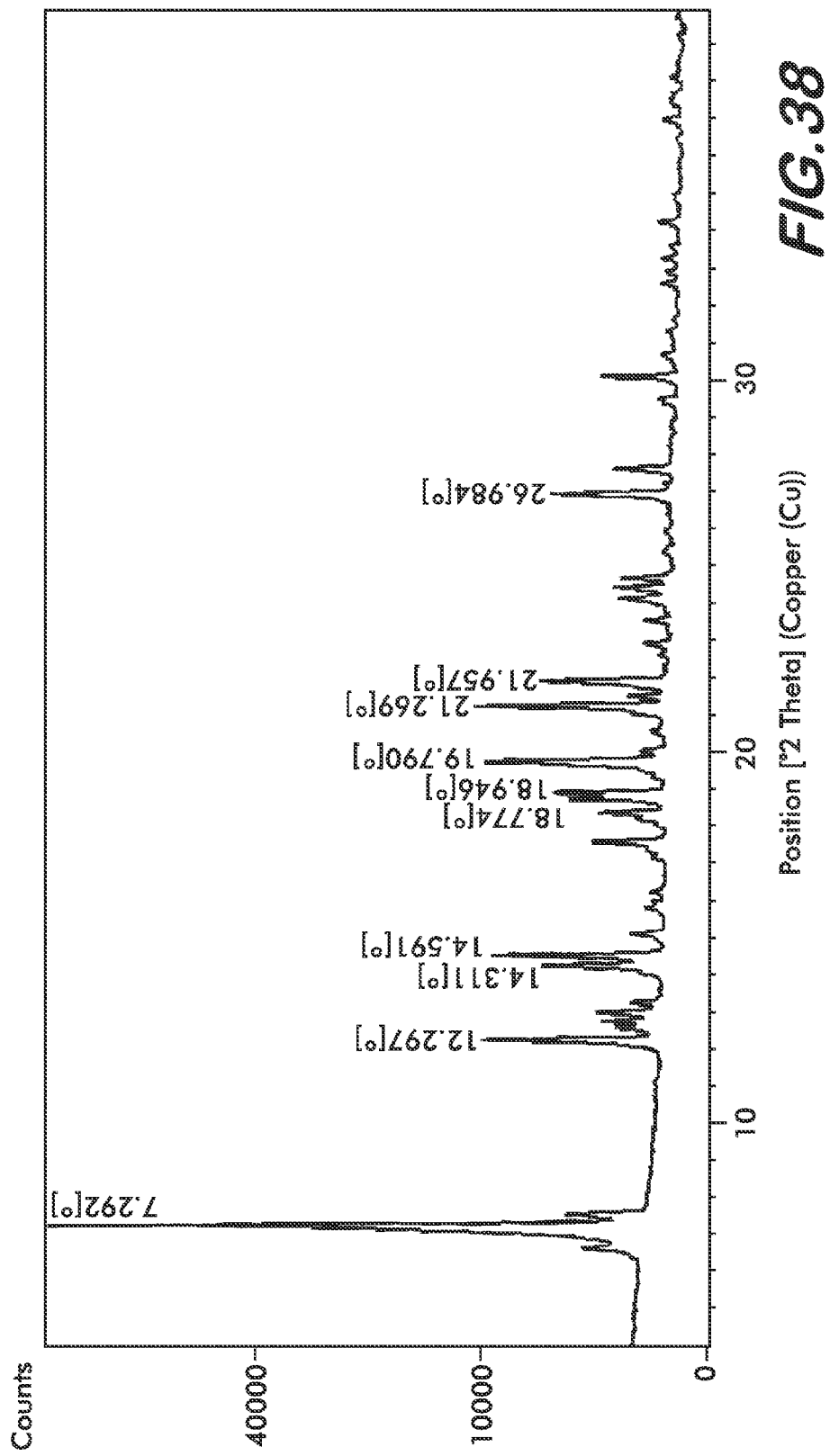
FIG. 38 is an X-ray Powder Diffractogram (XRPD) of Form $S_{15}$
Figure 39:
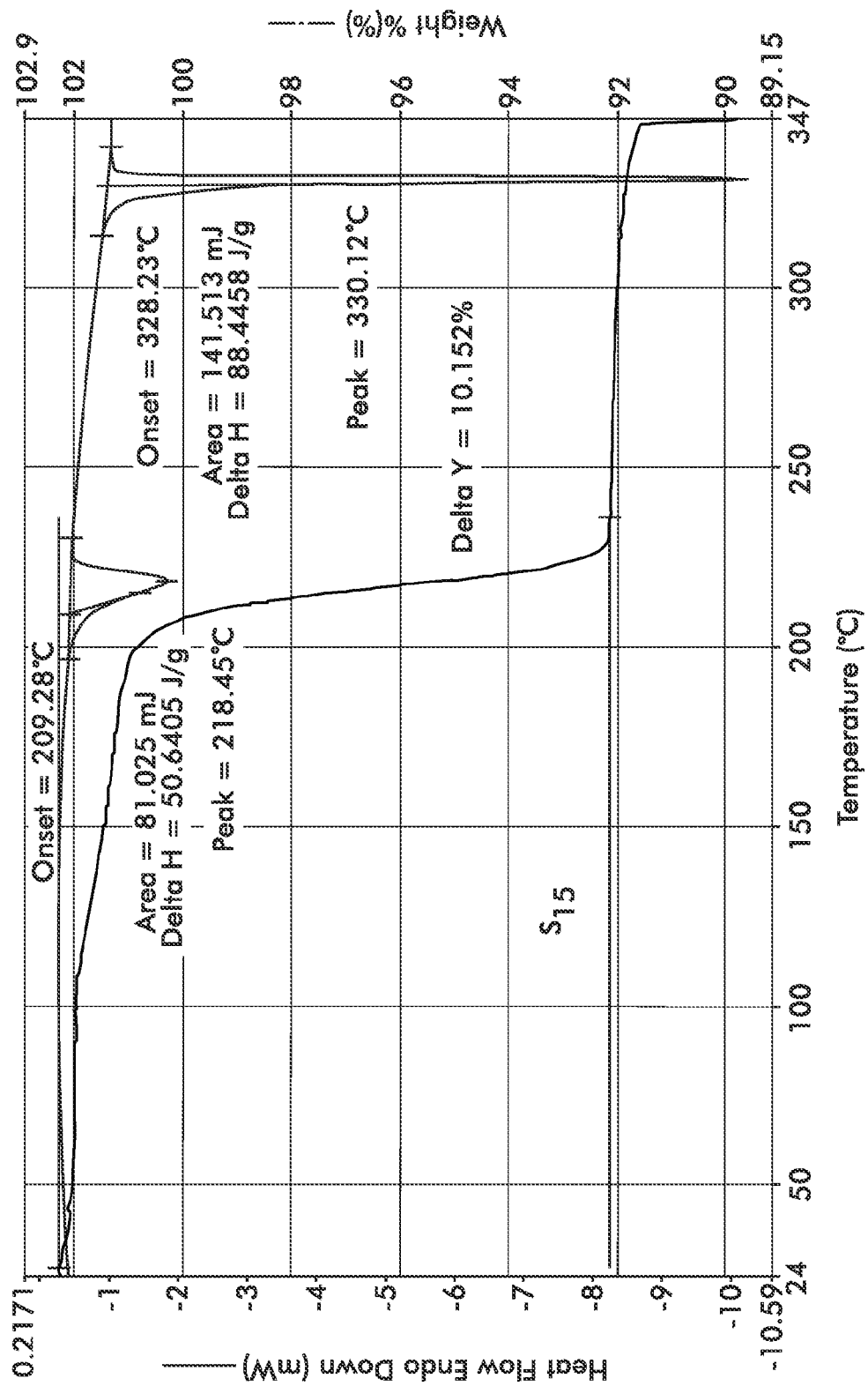
FIG. 39 is a Differential Scanning calorimetry (DSC) Thermogram and Thermo-Gravimetric Analysis (TGA) Thermogram overlay of Form $S_{15}$
Figure 40:
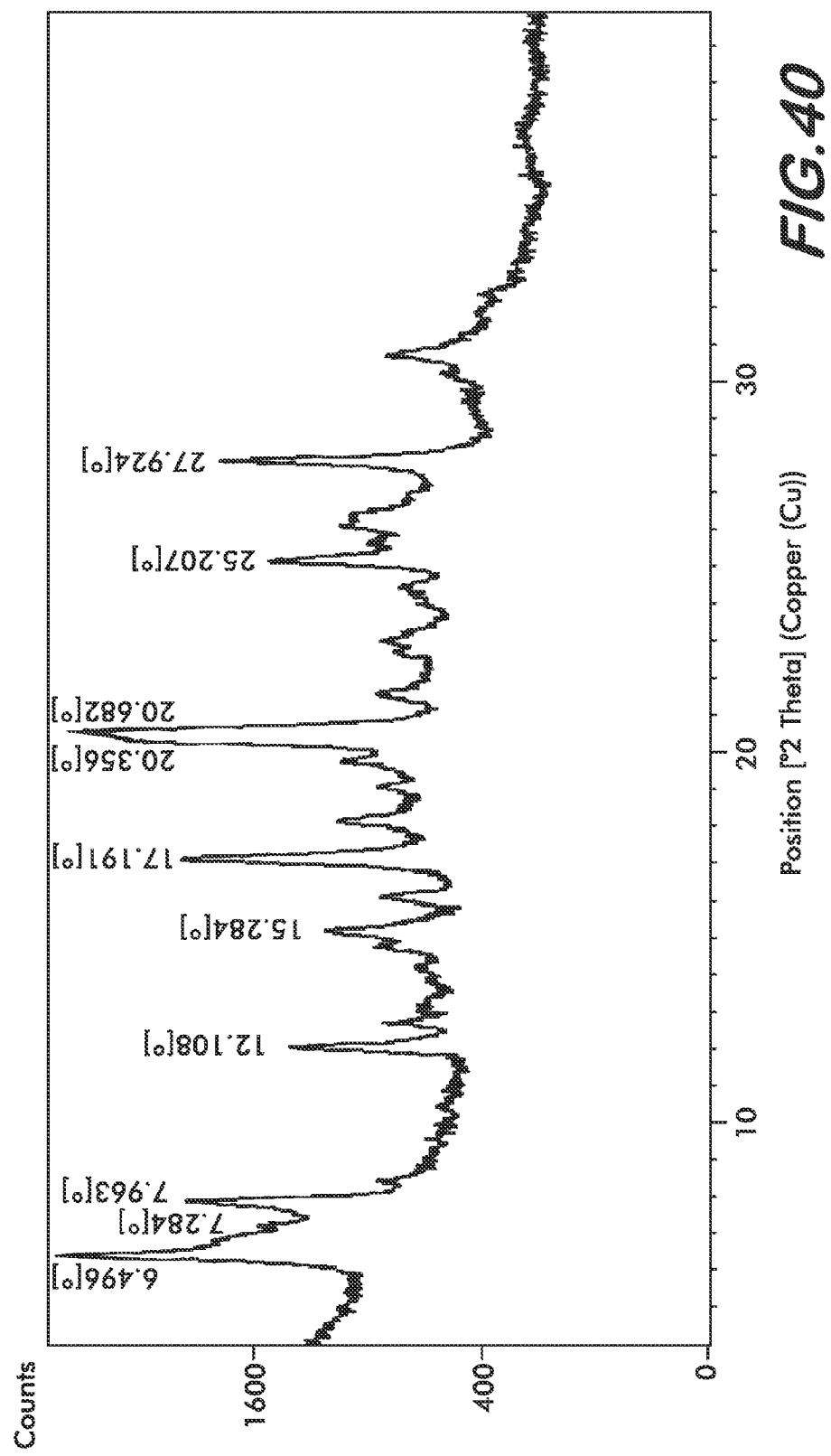
FIG. 40 is an X-ray Powder Diffractogram (XRPD) of Form $S_{16}$
Figure 41:
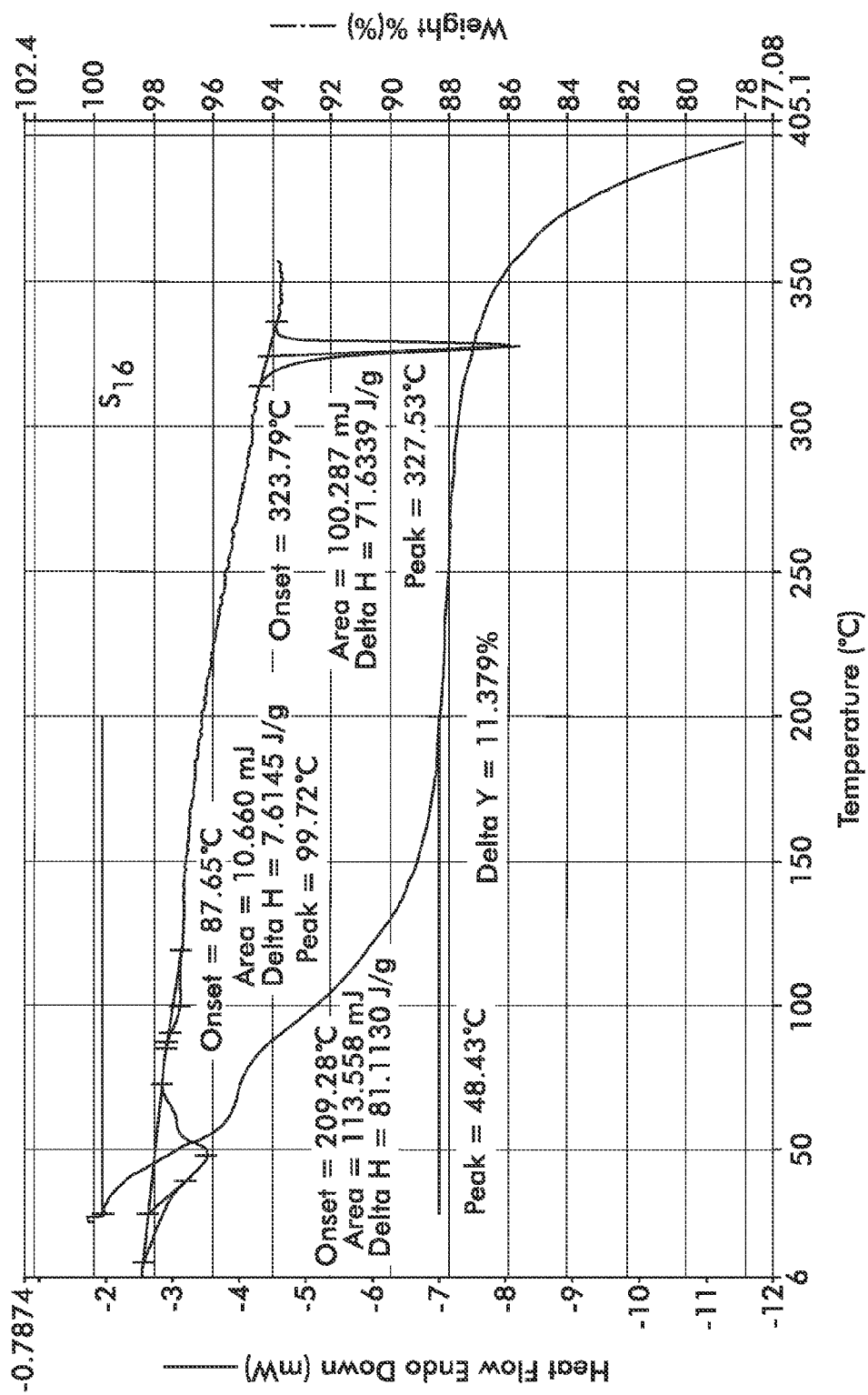
FIG. 41 is a Differential Scanning calorimetry (DSC) Thermogram and Thermo-Gravimetric Analysis (TGA) Thermogram overlay of Form $S_{16}$
Figure 42:
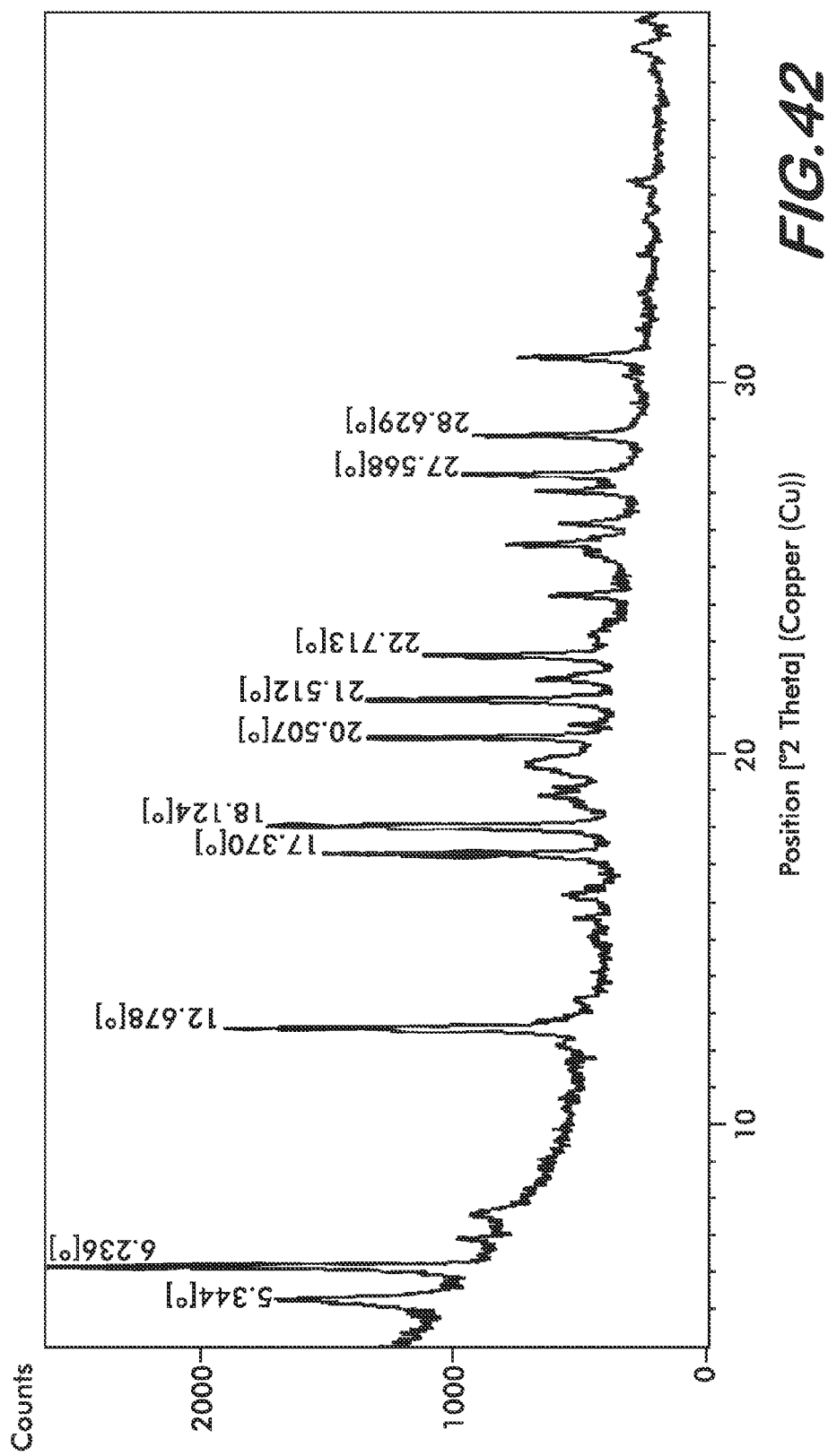
FIG. 42 is an X-ray Powder Diffractogram (XRPD) of Form $S_{17}$
Figure 43:
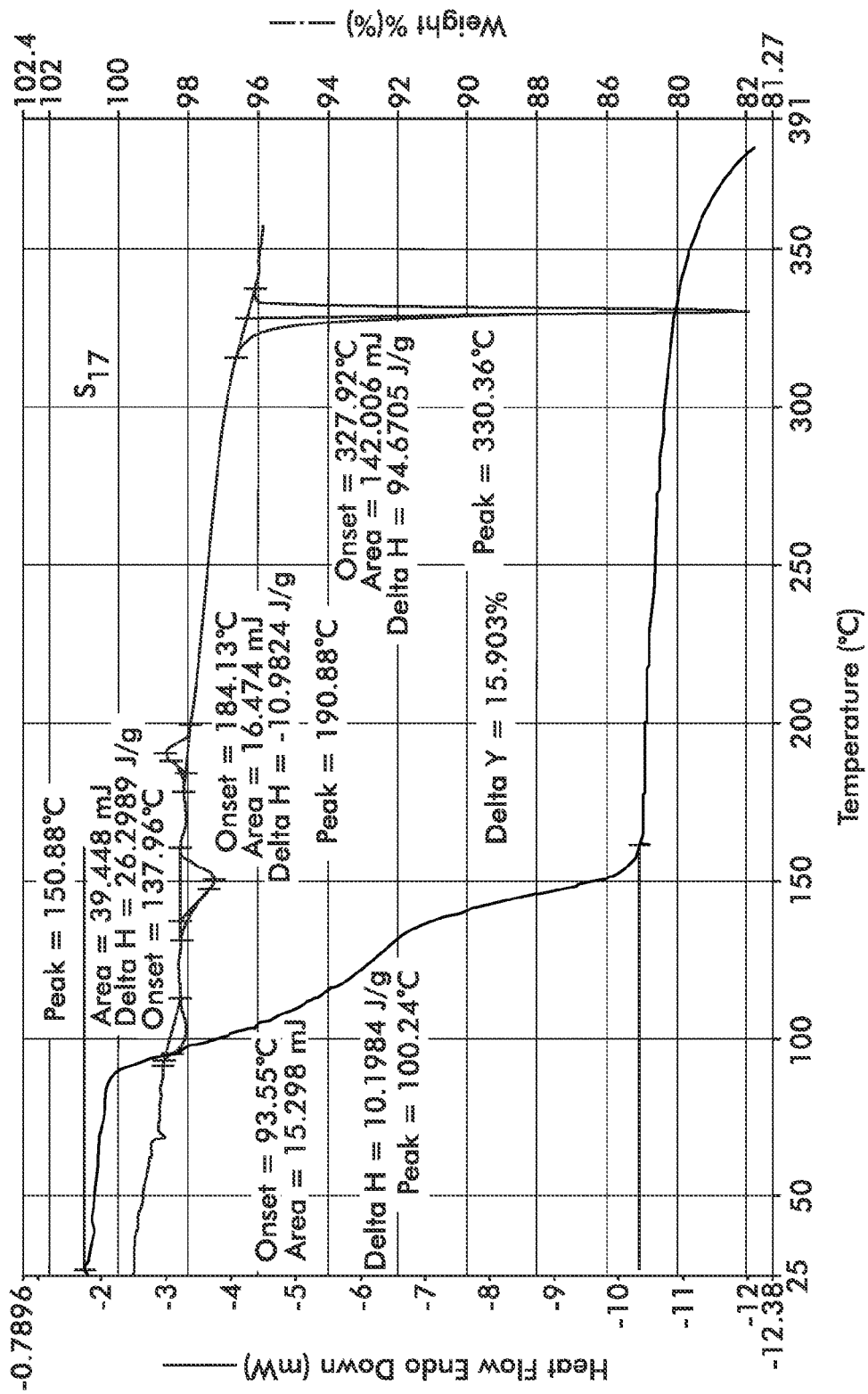
FIG. 43 is a Differential Scanning calorimetry (DSC) Thermogram and Thermo-Gravimetric Analysis (TGA) Thermogram overlay of Form $S_{18}$
Figure 44:
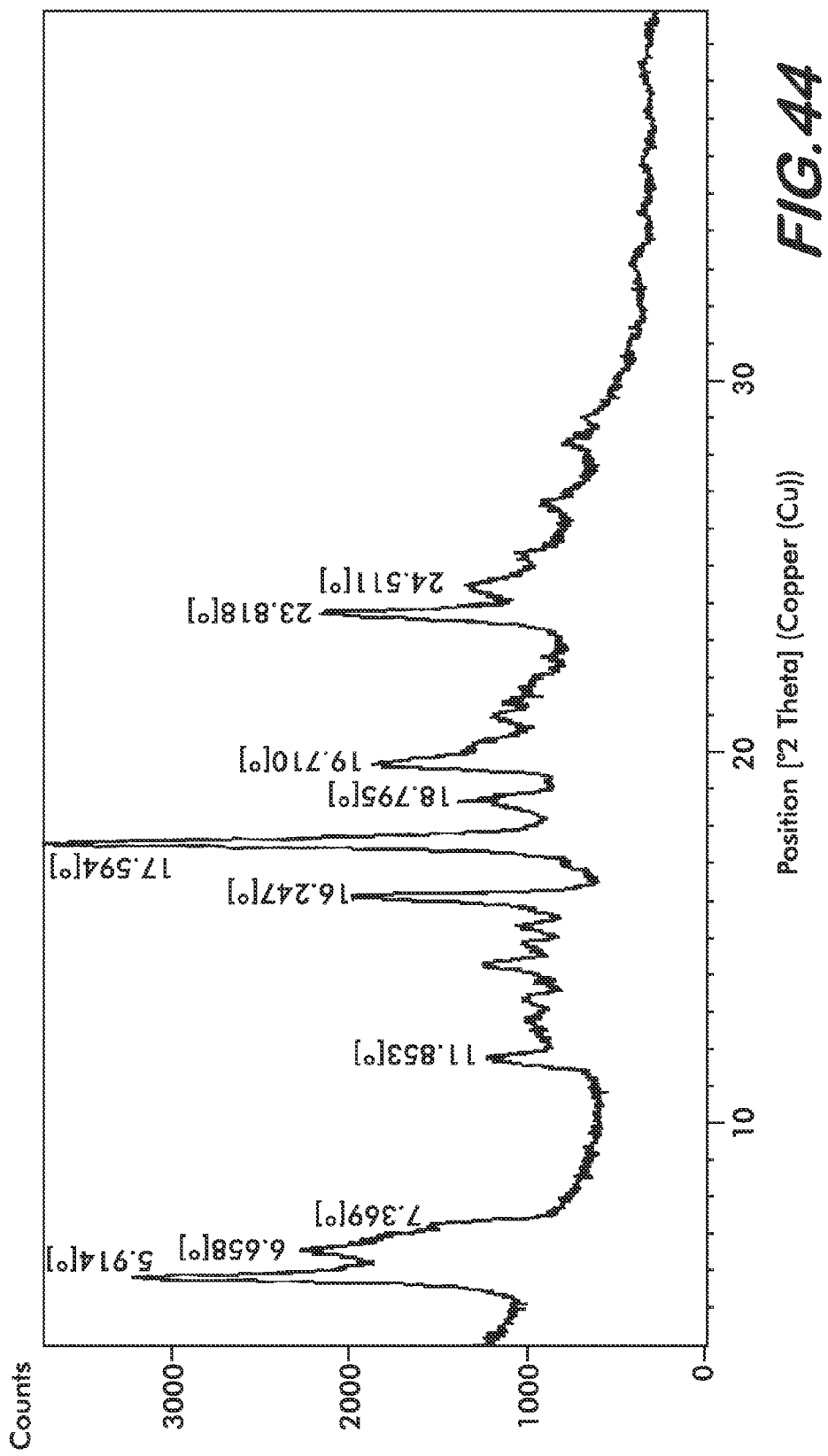
FIG. 44 is an X-ray Powder Diffractogram (XRPD) of Form $S_{18}$
Figure 45:
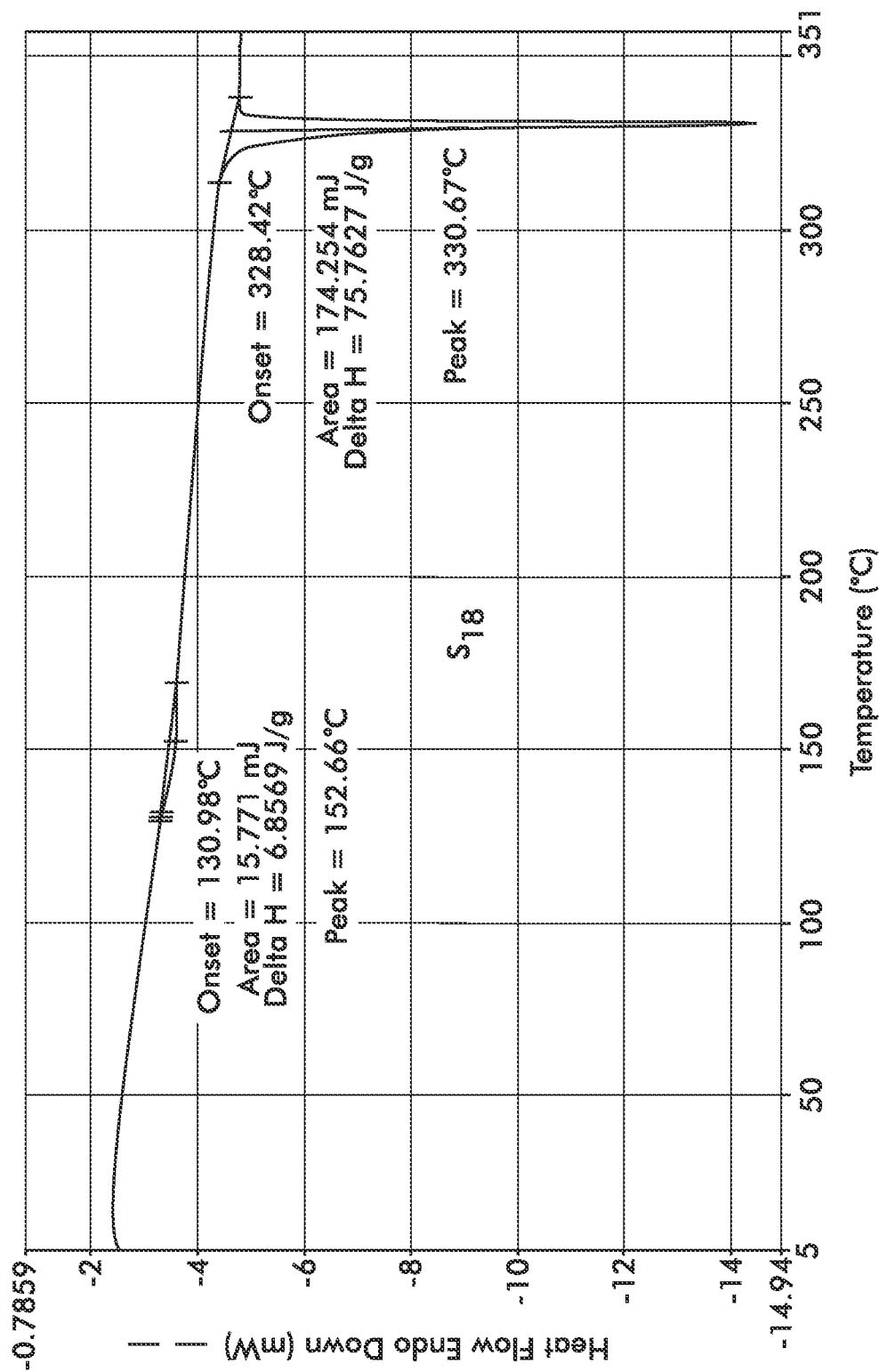
FIG. 45 is a Differential Scanning calorimetry (DSC) Thermogram of Form $S_{18}$
Figure 46:
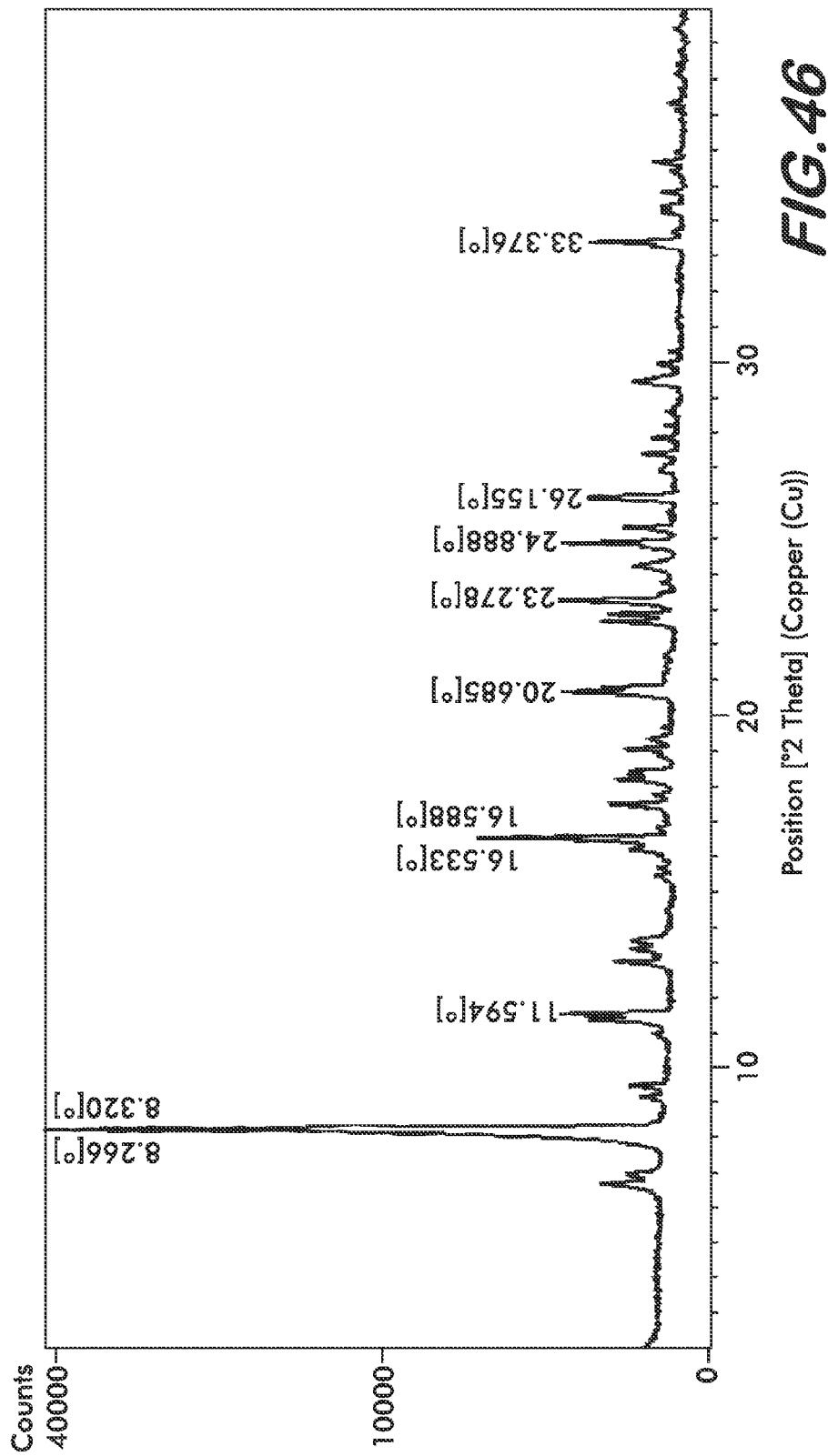
FIG. 46 is an X-ray Powder Diffractogram (XRPD) of Form $S_{19}$
Figure 47:
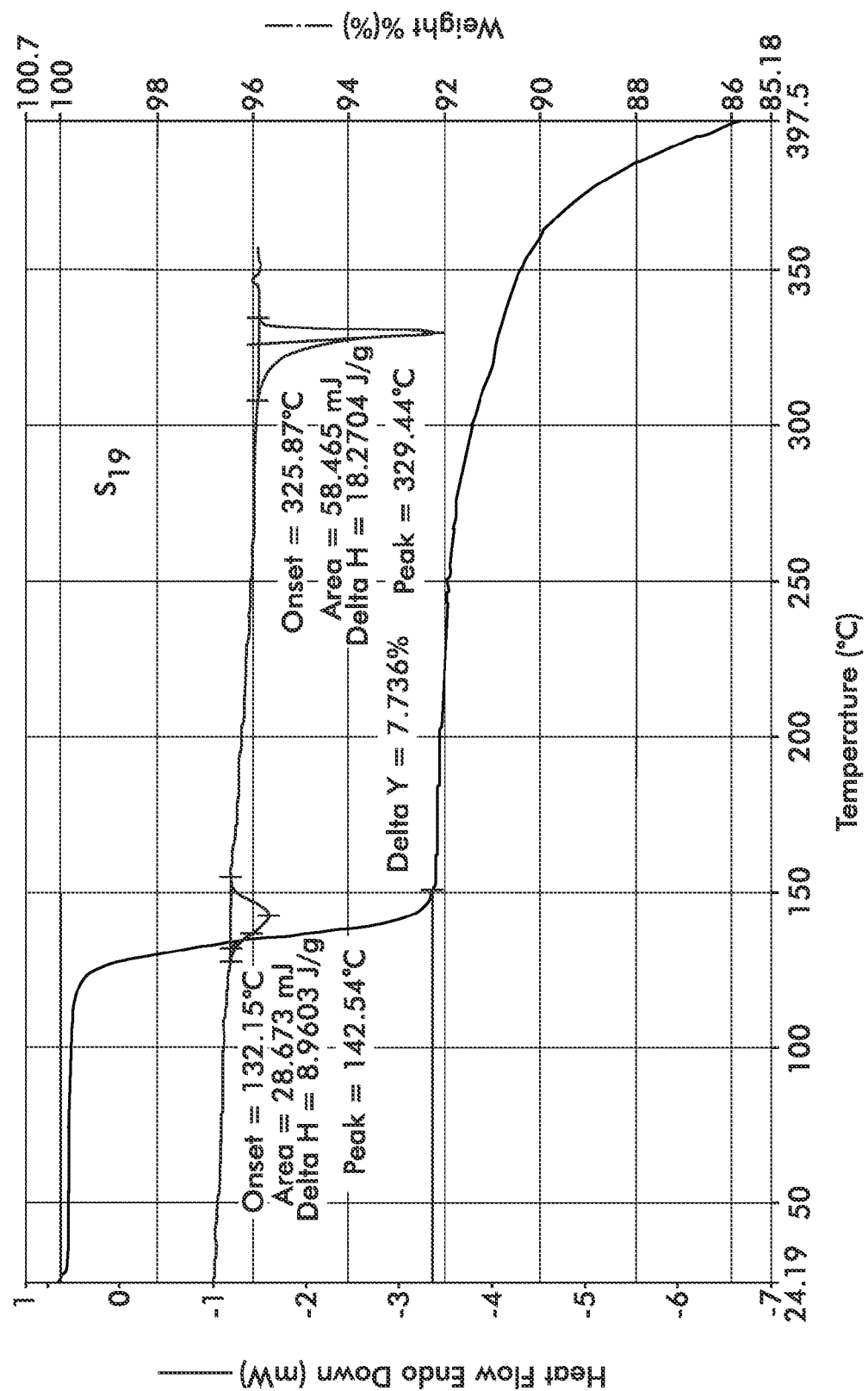
FIG. 47 is a Differential Scanning calorimetry (DSC) Thermogram and Thermo-Gravimetric Analysis (TGA) Thermogram overlay of Form $S_{16}$
Figure 48:
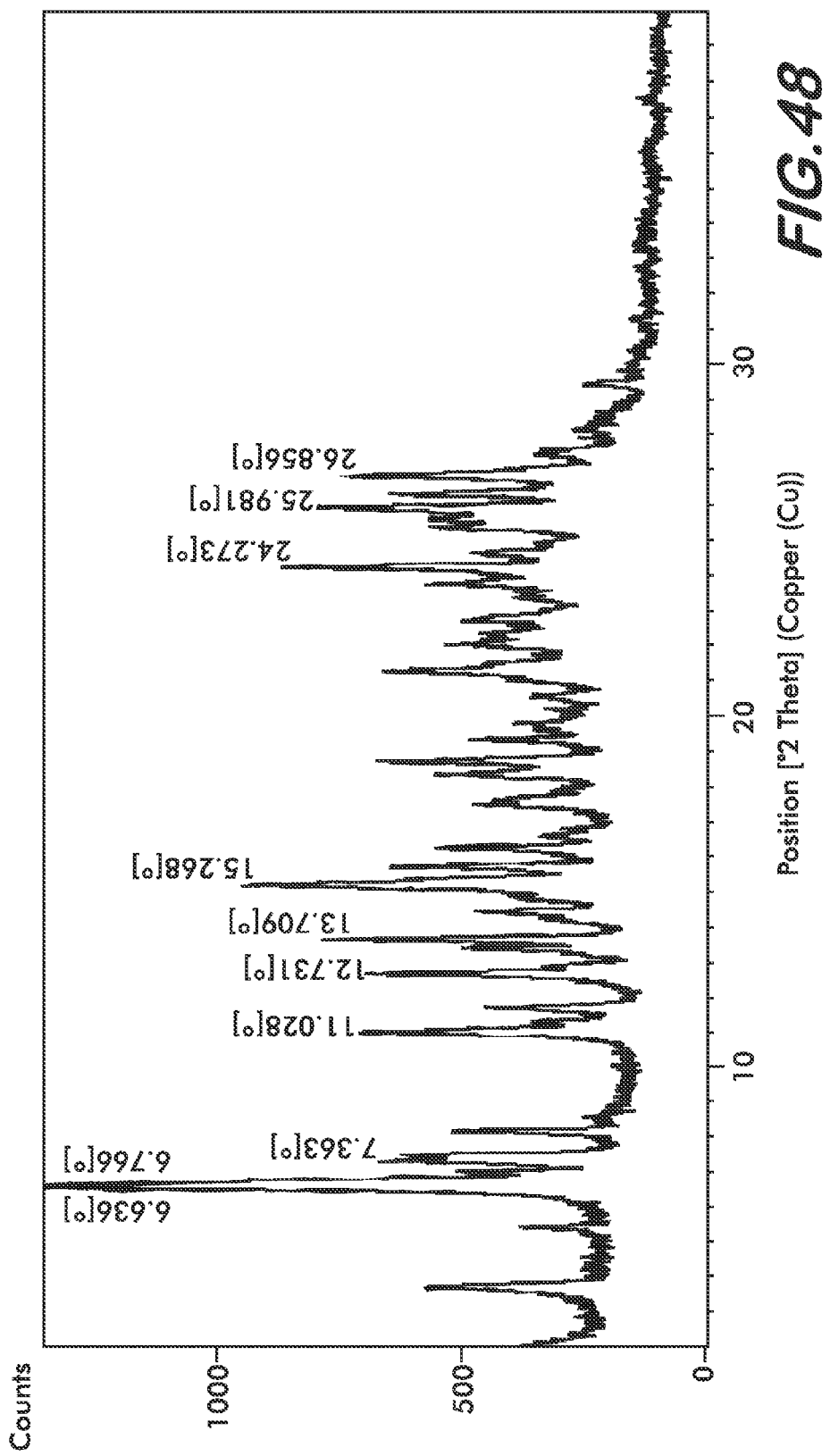
FIG. 48 is an X-ray Powder Diffractogram (XRPD) of Form $S_{20}$
Figure 49:
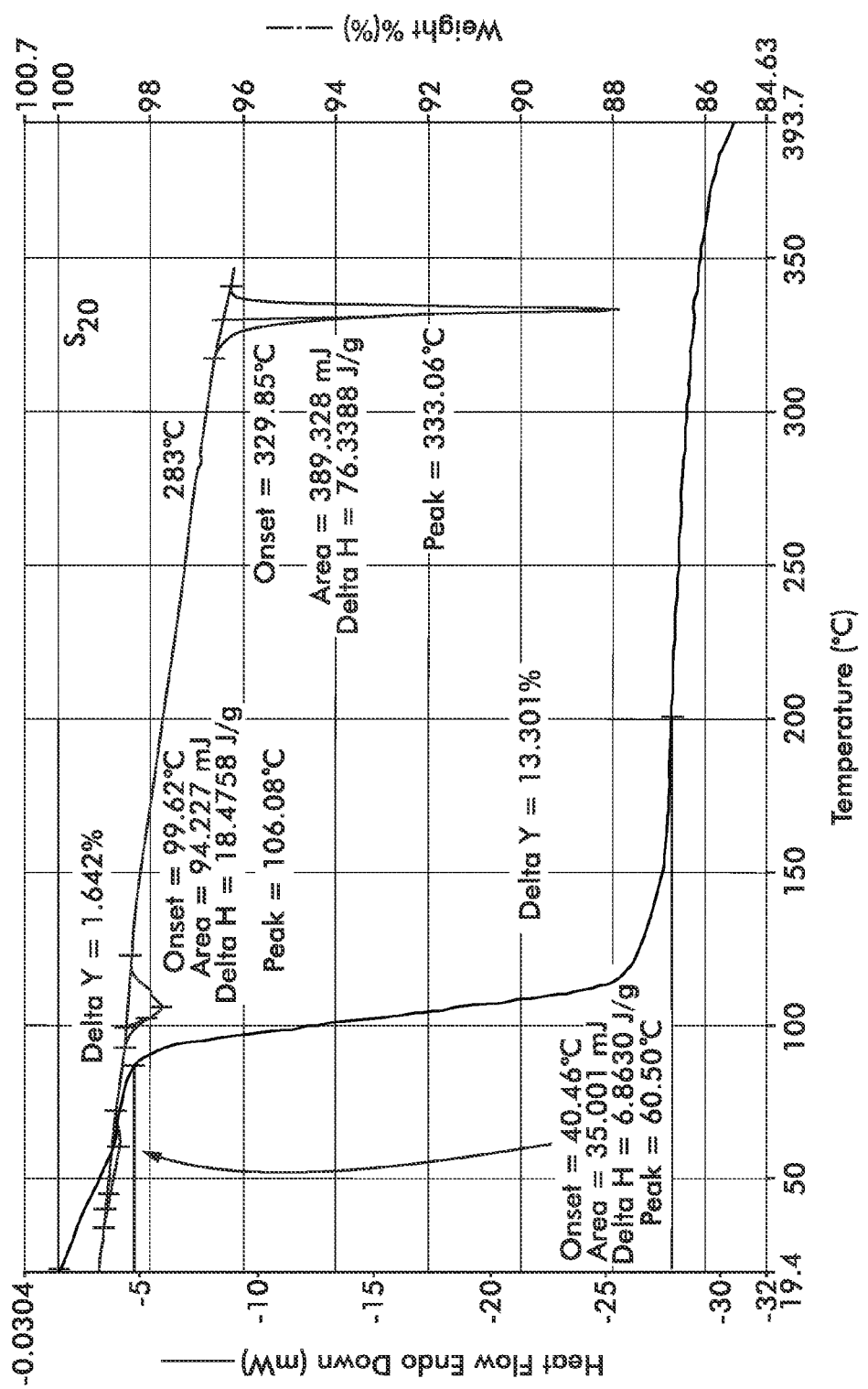
FIG. 49 is a Differential Scanning calorimetry (DSC) Thermogram and Thermo-Gravimetric Analysis (TGA) Thermogram overlay of Form $S_{20}$

A further aspect pertains to a crystalline form of Compound I that is Form $D_0$, characterized by an X-ray diffraction pattern comprising one or more of the following peaks: 7.16, 7.51, 12.75, 21.04 and/or 26.86±0.2 degrees 2-theta. Another aspect pertains to a crystalline form of Compound I that is Form $D_0$, having an X-ray powder diffraction pattern substantially as depicted in FIG. 15.

Yet another aspect of the present invention pertains to a pharmaceutical composition comprising Compound I Form $A_0$, $B_0$, $C_0$, $D_0$ or a mixture thereof. In a further aspect, the pharmaceutical composition comprises Form $A_0$. In another aspect, the pharmaceutical composition comprises Form $B_0$. In yet another aspect, the pharmaceutical composition comprises Form $C_0$. In still another aspect, the pharmaceutical composition comprises Form $D_0$.

An additional aspect of the present invention pertains to a method for preparing a crystalline form of Compound I that is Form $A_0$, comprising the step of crystallizing Compound I in the presence of isopropyl acetate to yield Form $A_0$. A further aspect pertains to a method for preparing a crystalline form of Compound I that is Form $A_0$, comprising the step of crystallizing Compound I in the presence of acetic acid and isopropyl acetate to yield Form $A_0$. Yet another aspect pertains to a method for preparing a crystalline form of Compound I that is Form $A_0$, comprising the step of heating Compound I.

A further aspect of the present invention pertains to a method for preparing a crystalline form of Compound I that is Form $B_0$, comprising the step of crystallizing Compound I in the presence of acetonitrile to yield Form $B_0$. Still another aspect pertains to a method for preparing a crystalline form of Compound I that is Form $C_0$, comprising the step of crystallizing Compound I in the presence of dichloroethane to yield Form $C_0$. An additional aspect pertains to a method for preparing a crystalline form of Compound I that is Form $D_0$, comprising the step of crystallizing Compound I in the presence of methanol to yield Form $D_0$.

An additional aspect of the present invention pertains to a method of treating solid tumors comprising the step of administering to a patient in need thereof a therapeutically effective amount of a crystalline form of Compound I that is Form $A_0$, Form $B_0$, Form $C_0$, Form $D_0$ or a mixture thereof. In another aspect, the crystalline form is Form $A_0$. In a further aspect, the crystalline form is Form $B_0$. In still another aspect, the crystalline form is Form $C_0$. In yet another aspect, the crystalline form is Form $D_0$. Still another aspect of the present invention pertains to a method of treating solid tumors comprising the step of administering to a patient in need thereof a pharmaceutical composition comprising Compound I Form $A_0$, $B_0$, $C_0$, $D_0$ or a mixture thereof. In a further aspect, the pharmaceutical composition comprises Form $A_0$. In another aspect, the pharmaceutical composition comprises Form $B_0$. In yet another aspect, the pharmaceutical composition comprises Form $C_O$. In still another aspect, the pharmaceutical composition comprises Form $D_0$.

An additional aspect of the present invention pertains to a crystalline form of Compound I that is Form $S_1$, Form $S_2$, Form $S_3$, Form $S_4$, Form $S_6$, Form $S_7$, Form $S_8$, Form $S_9$, Form $S_{10}$, Form $S_{13}$, Form $S_{14}$, Form $S_{15}$, Form $S_{16}$, Form $S_{17}$, Form $S_{18}$, Form $S_{19}$ or Form $S_{20}$, or a mixture thereof. In another aspect, the crystalline form of Compound I is Form $S_1$. In a further aspect, the crystalline form of Compound I is Form $S_2$. In a further aspect, the crystalline form of Compound I is Form $S_3$. In still another aspect, the crystalline form of Compound I is Form $S_4$. In an additional aspect, the crystalline form of Compound I is Form $S_6$. In still another aspect, the crystalline form of Compound I is Form $S_7$. In yet another aspect, the crystalline form of Compound I is Form $S_8$. In a further aspect, the crystalline form of Compound I is Form $S_9$. In an additional aspect, the crystalline form of Compound I is Form $S_{10}$. In still another aspect, the crystalline form of Compound I is Form $S_{13}$. In a further aspect, the crystalline form of Compound I is Form $S_{14}$. In still another aspect, the crystalline form of Compound I is Form $S_{15}$. In an additional aspect, the crystalline form of Compound I is Form $S_{16}$. In still another aspect, the crystalline form of Compound I is Form $S_{17}$. In a further aspect, the crystalline form of Compound I is Form $S_{18}$. In yet another aspect, the crystalline form of Compound I is Form $S_{19}$. In an additional aspect, the crystalline form of Compound I is Form $S_{20}$.

A further aspect of the present invention pertains to a crystalline form of Compound I that is Form $S_1$, characterized by an X-ray powder diffraction pattern comprising one or more of the following peaks: 5.50, 7.21, 7.76, 19.69 and/or 25.26±0.2 degrees 2-theta.

Another aspect pertains to a crystalline form of Compound I that is Form $S_2$, characterized by an X-ray powder diffraction pattern comprising one or more of the following peaks: 7.26, 14.52, 19.91 and/or 21.63±0.2 degrees 2-theta.

Still another aspect pertains to a crystalline form of Compound I that is Form $S_3$, characterized by an X-ray powder diffraction pattern comprising one or more of the following peaks: 6.67, 17.40, 20.04, 20.58 and/or 25.43±0.2 degrees 2-theta.

Yet another aspect pertains to a crystalline form of Compound I that is Form $S_4$, characterized by an X-ray powder diffraction pattern comprising one or more of the following peaks: 5.55, 7.84, 18.86, 19.71 and/or 22.31±0.2 degrees 2-theta.

An additional aspect pertains to a crystalline form of Compound I that is Form $S_6$, characterized by an X-ray powder diffraction pattern comprising one or more of the following peaks: 8.10, 13.46, 17.29, 20.78 and/or 28.03±0.2 degrees 2-theta.

A further aspect pertains to a crystalline form of Compound I that is Form $S_7$, characterized by an X-ray powder diffraction pattern comprising one or more of the following peaks: 6.86, 13.93, 19.27, 20.87 and/or 21.06±0.2 degrees 2-theta.

Another aspect of the present invention pertains to a crystalline form of Compound I that is Form $S_8$, characterized by an X-ray powder diffraction pattern comprising one or more of the following peaks: 6.35, 7.31, 21.54, 21.65 and/or 27.40±0.2 degrees 2-theta.

Still another aspect pertains to a crystalline form of Compound I that is Form $S_9$, characterized by an X-ray powder diffraction pattern comprising one or more of the following peaks: 6.77, 13.53, 18.81, 20.84 and 26.8 degrees 2-theta.

Yet another aspect pertains to a crystalline form of Compound I that is Form $S_{10}$, characterized by an X-ray powder diffraction pattern comprising one or more of the following peaks: 5.84, 7.64, 11.49, 20.23, and/or 23.84±0.2 degrees 2-theta.

A further aspect of the present invention pertains to a crystalline form of Compound I that is Form $S_{13}$, characterized by an X-ray powder diffraction pattern comprising one or more of the following peaks: 6.75, 7.08, 7.26, 7.60 and/or 22.70±0.2 degrees 2-theta.

An additional aspect pertains to a crystalline form of Compound I that is Form $S_{14}$, characterized by an X-ray powder diffraction pattern comprising one or more of the following peaks: 7.44, 14.88, 20.20, 21.61 and/or 22.39±0.2 degrees 2-theta.

Still another aspect pertains to a crystalline form of Compound I that is Form $S_{15}$, characterized by an X-ray powder diffraction pattern comprising one or more of the following peaks: 7.29, 12.30, 14.59, 19.79 and/or 21.27±0.2 degrees 2-theta.

A further aspect of the present invention pertains to a crystalline form of Compound I that is Form $S_{16}$, characterized by an X-ray powder diffraction pattern comprising one or more of the following peaks: 6.50, 17.19, 20.36, 20.68 and/or 27.92±0.2 degrees 2-theta.

An additional aspect pertains to a crystalline form of Compound I that is Form $S_{17}$, characterized by an X-ray powder diffraction pattern comprising one or more of the following peaks: 6.24, 12.68, 17.37, 18.12 and/or 21.51±0.2 degrees 2-theta.

Yet another aspect pertains to a crystalline form of Compound I that is Form $S_{18}$, characterized by an X-ray powder diffraction pattern comprising one or more of the following peaks: 5.91, 6.66, 16.25, 17.59 and/or 23.82±0.2 degrees 2-theta.

Still another aspect pertains to a crystalline form of Compound I that is Form $S_{19}$, characterized by an X-ray powder diffraction pattern comprising one or more of the following peaks: 8.27, 8.32, 16.53, 16.59 and 23.28±0.2 degrees 2-theta.

A further aspect of the present invention pertains to a crystalline form of Compound I that is Form $S_{20}$, characterized by an X-ray powder diffraction pattern comprising one or more of the following peaks: 6.64, 6.77, 11.03, 15.27 and/or 24.27±0.2 degrees 2-theta.

An additional aspect of the present invention pertains to a pharmaceutical composition comprising a crystalline form of Compound I that is Form $S_1$, Form $S_2$, Form $S_3$, Form $S_4$, Form $S_6$, Form $S_7$, Form $S_8$, Form $S_9$, Form $S_{10}$, Form $S_{13}$, Form $S_{14}$, Form $S_{15}$, Form $S_{16}$, Form $S_{17}$, Form $S_{18}$, Form $S_{19}$ or Form $S_{20}$, or a mixture thereof.

In a further aspect, the pharmaceutical composition comprises Form $S_1$. In a further aspect, the pharmaceutical composition comprises Form $S_2$. In a further aspect, the pharmaceutical composition comprises Form $S_3$. In a further aspect, the pharmaceutical composition comprises Form $S_4$. In still another aspect, the pharmaceutical composition comprises Form $S_6$. In yet another aspect, the pharmaceutical composition comprises Form $S_7$. In a further aspect, the pharmaceutical composition comprises Form $S_8$. In an additional aspect, the pharmaceutical composition comprises Form $S_9$. In still another aspect, the pharmaceutical composition comprises Form $S_{10}$. In an additional aspect, the pharmaceutical composition comprises Form $S_{13}$. In yet another aspect, the pharmaceutical composition comprises Form $S_{14}$. In an additional aspect, the pharmaceutical composition comprises Form $S_{15}$. In a further aspect, the pharmaceutical composition comprises Form $S_{16}$. In another aspect, the pharmaceutical composition comprises Form $S_{17}$. In another aspect, the pharmaceutical composition comprises Form $S_{18}$. In an additional aspect, the pharmaceutical composition comprises Form $S_{19}$. In still another aspect, the pharmaceutical composition comprises Form $S_{20}$.

An additional aspect of the present invention pertains to a method of treating solid tumors comprising the step of administering to a patient in need thereof a therapeutically effective amount of a crystalline form of Compound I that is Form $S_1$, Form $S_2$, Form $S_3$, Form $S_4$, Form $S_6$, Form $S_7$, Form $S_8$, Form $S_9$, Form $S_{10}$, Form $S_{13}$, Form $S_{14}$, Form $S_{15}$, Form $S_{16}$, Form $S_{17}$, Form $S_{18}$, Form $S_{19}$ or Form $S_{20}$, or a mixture thereof. Still another aspect of the present invention pertains to a method of treating solid tumors comprising the step of administering to a patient in need thereof a pharmaceutical composition comprising Compound I Form $S_1$, Form $S_2$, Form $S_3$, Form $S_4$, Form $S_6$, Form $S_7$, Form $S_8$, Form $S_9$, Form $S_{10}$, Form $S_{13}$, Form $S_{14}$, Form $S_{15}$, Form $S_{16}$, Form $S_{17}$, Form $S_{18}$, Form $S_{19}$ or Form $S_{20}$, or a mixture thereof.

An additional aspect of the present invention pertains to a crystalline form of Compound I that is Form $A_0$, wherein said crystalline form is characterized by unit cell parameters approximately equal to the following:

| Unit cell dimensions: | a = 27.5221(12) Å | α = 90° |
|---|---|---|
|  | b = 6.9321(5) Å | β = 106.035(6)° |
|  | c = 25.994(3) Å | γ = 90° |
| Crystal system: | Monoclinic | |
| Space group: | Cc | |
| Molecules/unit cell: | 2. | |

A further aspect pertains to a method for preparing a crystalline form of Compound I that is Form $A_0$ using a spontaneous crystallization method. In a further aspect, PEG/polaxamer is used as the crystallization solvent.

Still another aspect of the present invention pertains to a pharmaceutical composition comprising a crystalline form of Compound I that is Form $A_0$, wherein said crystalline form is characterized by unit cell parameters approximately equal to the following:

| Unit cell dimensions: | a = 27.5221(12) Å | α = 90° |
|---|---|---|
|  | b = 6.9321(5) Å | β = 106.035(6)° |
|  | c = 25.994(3) Å | γ = 90° |
| Crystal system: | Monoclinic | |
| Space group: | Cc | |
| Molecules/unit cell: | 2. | |

An additional aspect of the present invention pertains to a crystalline form of Compound I that is an Ethanol Solvate single crystal. In a further aspect, the crystalline form is characterized by unit cell parameters approximately equal to the following:

| Unit cell dimensions: | a = 8.131(2) Å | α = 65.179(16)° |
|---|---|---|
|  | b = 13.271(3) Å | β = 86.51(2) |
|  | c = 13.6390(17) Å | γ = 83.69(2)° |
| Crystal system: | Triclinic | |
| Space group: | Pbar1 | |
| Molecules/unit cell: | 2. | |

Yet another aspect of the present invention pertains to a crystalline form of Compound I that is an NMP 1:1 Water Solvate single crystal. In a further aspect, the crystalline form is characterized by unit cell parameters approximately equal to the following:

| Unit cell dimensions: | a = 8.2359(7) Å | α = 65.451(7)° |
|---|---|---|
|  | b = 13.5644(10) Å | β = 88.496(7) |
|  | c = 14.4408(11) Å | γ = 87.326(7)° |
| Crystal system: | Triclinic | |
| Space group: | Pbar1 | |
| Molecules/unit cell: | 2. | |

Still another aspect of the present invention pertains to a crystalline form of Compound I that is a Tetrahydrofuran Solvate single crystal. In a further aspect, the crystalline form is characterized by unit cell parameters approximately equal to the following:

| Unit cell dimensions: | a = 17.6686(7) Å | α = 90° |
|---|---|---|
|  | b = 11.0367(5) Å | β = 90° |
|  | c = 29.2660(11) Å | γ = 90° |
| Crystal system: | orthorhombic | |
| Space group: | Pbcn | |
| Molecules/unit cell: | 8. | |

An additional aspect of the present invention pertains to a crystalline form of Compound I that is a 2-Propanol Solvate single crystal. In a further aspect, the crystalline form is characterized by unit cell parameters approximately equal to the following:

| Unit cell dimensions: | a = 8.1404(18) Å | α = 66.60(2)° |
|---|---|---|
|  | b = 13.566(3) Å | β = 86.583(17)° |
|  | c = 13.566(3) Å | γ = 86.583(17)° |
| Crystal system: | triclinic | |
| Space group: | Pbar1 | |
| Molecules/unit cell: | 8. | |

Figure 50:
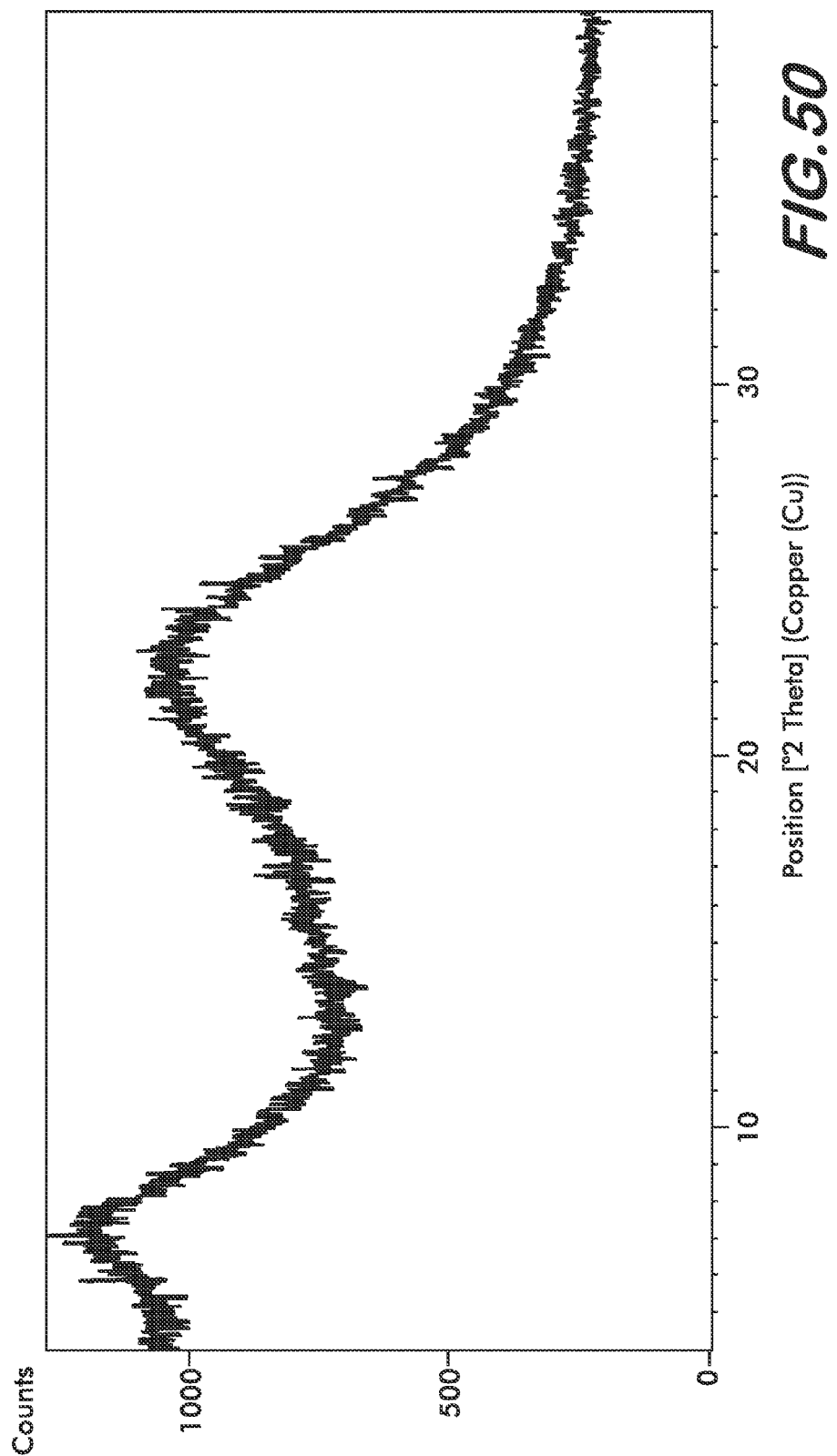
FIG. 50 is an X-ray Powder Diffractogram (XRPD) of Amorphous Solid (AS)

Still another aspect of the present invention pertains to an amorphous form of Compound I that is an Amorphous Solid (AS). In an additional aspect, the amorphous form has an X-ray powder diffraction pattern substantially as depicted in FIG. 50. Yet another aspect pertains to a pharmaceutical composition comprising the amorphous form of Compound I that is an Amorphous Solid (AS).

An additional aspect of the present invention pertains to a method for preparing Amorphous Solid (AS) comprising the step of dissolving Compound I in the presence of methanol to yield Amorphous Solid (AS). Another aspect pertains to a method for preparing Amorphous Solid (AS) comprising the step of dissolving Compound I in the presence of ethanol to yield Amorphous Solid (AS). An additional aspect pertains to a method for preparing Amorphous Solid (AS) comprising the step of grinding Compound I Form $A_0$ to yield Amorphous Solid (AS). A further aspect pertains to a method for preparing Amorphous Solid (AS) comprising the step of quench cooling Compound I Form $A_0$ to yield Amorphous Solid (AS).

Still another aspect of the present invention pertains to a method of treating solid tumors comprising the step of administering to a patient in need thereof a therapeutically effective amount of an amorphous form of Compound I that is an Amorphous Solid (AS).

TERMINOLOGY

The term "amorphous," as used herein, means lacking a characteristic crystal shape or crystalline structure.

The term "anti-solvent," as used herein, means a solvent in which a compound is substantially insoluble.

The term "crystalline," as used herein, means having a regularly repeating arrangement of molecules or external face planes.

The term "crystalline form," as used in herein, refers to a solid chemical compound or mixture of compounds that provides a characteristic pattern of peaks when analyzed by x-ray powder diffraction; this includes, but is not limited to, polymorphs, solvates, hydrates, co-crystals, and de-solvated solvates. For the purpose of describing the present invention, the number '1' was assigned to identify mono (para-toluenesulfonic acid (pTSA) crystalline salt forms such as pTSA-$A_1$ and the number '2' was used to identify the di pTSA crystalline salt forms such as pTSA-$A_2$, pTSA-$B_2$ and pTSA-$C_2$. In addition, the letters A, B, C and D were used to identify the four polymorphic forms of Compound I free base (with the subscript '0' specifying the free base in each case). The letter 'S' was used to identify each of the solvates, with numbers consecutively assigned to describe each solvate. The term "Amorphous Solid (AS)" was used to identify the amorphous form of Compound I.

The term "isolating" as used herein, means separating a compound from a solvent, anti-solvent, or a mixture of solvent and anti-solvent to provide a solid, semisolid or syrup. This is typically accomplished by means such as centrifugation, filtration with or without vacuum, filtration under positive pressure, distillation, evaporation or a combination thereof. Isolating may or may not be accompanied by purifying during which the chemical, chiral or chemical and chiral purity of the isolate is increased. Purifying is typically conducted by means such as crystallization, distillation, extraction, filtration through acidic, basic or neutral alumina, filtration through acidic, basic or neutral charcoal, column chromatography on a column packed with a chiral stationary phase, filtration through a porous paper, plastic or glass barrier, column chromatography on silica gel, ion exchange chromatography, re-crystallization, normal-phase high performance liquid chromatography, reverse-phase high performance liquid chromatography, trituration and the like.

The term "polymorphic" or "polymorphism" is defined as the possibility of at least two different crystalline arrangements for the same chemical molecule.

The term "solute" as used herein, refers to a substance dissolved in another substance, usually the component of a solution present in the lesser amount.

The term "solution," as used herein, refers to a mixture containing at least one solvent and at least one compound at least partially dissolved in the solvent.

The term "solvate," as used herein, refers to a crystalline material that contains solvent molecules within the crystal structure.

The term "solvent," as used herein, means a substance, typically a liquid, that is capable of completely or partially dissolving another substance, typically a solid. Solvents for the practice of this invention include, but are not limited to, water, acetic acid, acetone, acetonitrile, 1-butanol, 2-butanol, 2-butanone, butyronitrile, tert-butanol, chlorobenzene, chloroform, cyclohexane, 1-2 dichloloroethane, dichloromethane, diethylene glycol dibutyl ether, diisopropyl amine, diisopropyl ether, 1,2-dimethoxyethane, N,N-dimethylacetamide, N,N-dimethylformamide, dimethyl sulfoxide, 1,4-dioxane, ethyleneglycoldiemethylether, ethanol, ethyl acetate, ethylene glycol, ethyl formate, formic acid, heptane, isobutyl alcohol, isopropyl acetate, isopropyl amine, methanol, methoxy benzene, methyl acetate, methyl isobutyl ketone, 2-methyltetrahydrofuran, methyl tert-butyl ether, 1:1 formamide:water, 1:1 N-methylpyrrolidinone, 2-pentanone, 3-pentanone, 1 pentanol, 1,2-propanediol, 2-propanol, 1-propanol, propanonitrile, pyridine, tetrahydrofuran, tetrahydropyran, toluene, triethyl amine, xylene, mixtures thereof and the like.

The term "therapeutically effective amount," as used herein, refers to the amount determined to be required to produce the physiological effect intended and associated with a given drug, as measured according to established pharmacokinetic methods and techniques, for the given administration route. Appropriate and specific therapeutically effective amounts can be readily determined by the attending diagnostician, as one skilled in the art, by the use of conventional techniques. The effective dose will vary depending upon a number of factors, including the type and extent of progression of the disease or disorder, the overall health status of the particular patient, the relative biological efficacy of the compound selected, the formulation of the active agent with appropriate excipients, and the route of administration.

Unless stated otherwise, percentages stated throughout this specification are weight/weight (w/w) percentages.

The term "pharmaceutically acceptable excipients," as used herein, includes any and all solvents, dispersion media, coatings, antibacterial and antifungal agents, isotonic and absorption delaying agents and the like. The use of such media and agents for pharmaceutical active substances is well known in the art, such as in *Remington: The Science and Practice of Pharmacy*, 20$^{th}$ ed.; Gennaro, A. R., Ed.; Lippincott Williams & Wilkins: Philadelphia, Pa., 2000. Except insofar as any conventional media or agent is incompatible with the active ingredient, its use in the therapeutic compositions is contemplated. Supplementary active ingredients can also be incorporated into the compositions.

For therapeutic purposes, the crystalline forms of the present invention can be administered by any means that results in the contact of the active agent with the agent's site of action in the body of the subject. The crystalline forms may be administered by any conventional means available for use in conjunction with pharmaceuticals, either as individual therapeutic agents or in combination with other therapeutic agents, such as, for example, analgesics. The crystalline forms of the present invention are preferably administered in therapeutically effective amounts for the treatment of the diseases and disorders described herein to a subject in need thereof.

A therapeutically effective amount can be readily determined by the attending diagnostician, as one skilled in the art, by the use of conventional techniques. The effective dose will vary depending upon a number of factors, including the type and extent of progression of the disease or disorder, the overall health status of the particular patient, the relative biological efficacy of the crystalline form selected, the formulation of the active agent with appropriate excipients, and the route of administration. Typically, the crystalline forms would be administered at lower dosage levels, with a gradual increase until the desired effect is achieved.

Typical dose ranges are from about 0.01 mg/kg to about 100 mg/kg of body weight per day, with a preferred dose from about 0.01 mg/kg to 10 mg/kg of body weight per day. A preferred daily dose for adult humans includes about 25, 50, 100 and 200 mg, and an equivalent dose in a human child. The crystalline forms may be administered in one or more unit dose forms. The unit dose ranges from about 1 to about 500 mg administered one to four times a day, preferably from about 10 mg to about 300 mg, two times a day. In an alternate method of describing an effective dose, an oral unit dose is one that is necessary to achieve a blood serum level of about 0.05 to 20 μg/ml in a subject, and preferably about 1 to 20 μg/ml.

The crystalline forms of the present invention may be formulated into pharmaceutical compositions by admixture with one or more pharmaceutically acceptable excipients. The excipients are selected on the basis of the chosen route of administration and standard pharmaceutical practice, as described, for example, in *Remington: The Science and Practice of Pharmacy*, 20$^{th}$ ed.; Gennaro, A. R., Ed.; Lippincott Williams & Wilkins: Philadelphia, Pa., 2000. The compositions may be formulated to control and/or delay the release of the active agent(s), as in fast-dissolve, modified-release, or sustained-release formulations. Such controlled-release, or extended-release compositions may utilize, for example biocompatible, biodegradable lactide polymers, lactide/glycolide copolymers, polyoxyethylene-polyoxypropylene copolymers, or other solid or semisolid polymeric matrices known in the art.

The compositions can be prepared for administration by oral means; parenteral means, including intravenous, intramuscular, and subcutaneous routes; topical or transdermal means; transmucosal means, including rectal, vaginal, sublingual and buccal routes; ophthalmic means; or inhalation means. Preferably the compositions are prepared for oral administration, particularly in the form of tablets, capsules or syrups; for parenteral administration, particularly in the form of liquid solutions, suspensions or emulsions; for intranasal administration, particularly in the form of powders, nasal drops, or aerosols; or for topical administration, such as creams, ointments, solutions, suspensions aerosols, powders and the like.

For oral administration, the tablets, pills, powders, capsules, troches and the like can contain one or more of the following: diluents or fillers such as starch, or cellulose; binders such as microcrystalline cellulose, gelatins, or polyvinylpyrrolidones; disintegrants such as starch or cellulose derivatives; lubricants such as talc or magnesium stearate; glidants such as colloidal silicon dioxide; sweetening agents such as sucrose or saccharin; or flavoring agents such as peppermint or cherry flavoring. Capsules may contain any of the aforementioned excipients, and may additionally contain a semi-solid or liquid carrier, such as a polyethylene glycol. The solid oral dosage forms may have coatings of sugar, shellac, or enteric agents. Liquid preparations may be in the form of aqueous or oily suspensions, solutions, emulsions, syrups, elixirs, etc., or may be presented as a dry product for reconstitution with water or other suitable vehicle before use. Such liquid preparations may contain conventional additives such as surfactants, suspending agents, emulsifying agents, diluents, sweetening and flavoring agents, dyes and preservatives.

The compositions may also be administered parenterally. The pharmaceutical forms acceptable for injectable use include, for example, sterile aqueous solutions, or suspensions. Aqueous carriers include mixtures of alcohols and water, buffered media, and the like. Non-aqueous solvents include alcohols and glycols, such as ethanol, and polyethylene glycols; oils, such as vegetable oils; fatty acids and fatty acid esters, and the like. Other components can be added including surfactants; such as hydroxypropylcellulose; isotonic agents, such as sodium chloride; fluid and nutrient replenishers; electrolyte replenishers; agents which control the release of the active compounds, such as aluminum monostearate, and various co-polymers; antibacterial agents, such as chlorobutanol, or phenol; buffers, and the like. The parenteral preparations can be enclosed in ampules, disposable syringes or multiple dose vials. Other potentially useful parenteral delivery systems for the active compounds include ethylene-vinyl acetate copolymer particles, osmotic pumps, implantable infusion systems, and liposomes.

Other possible modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for topical use are in the form of an ointment, cream, or gel. Typically these forms include a carrier, such as petrolatum, lanolin, stearyl alcohol, polyethylene glycols, or their combinations, and either an emulsifying agent, such as sodium lauryl sulfate, or a gelling agent, such as tragacanth. Formulations suitable for transdermal administration can be presented as discrete patches, as in a reservoir or microreservoir system, adhesive diffusion-controlled system or a matrix dispersion-type system. Formulations for buccal administration include, for example lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicyclate.

Instrumentation

X-Ray Powder Diffraction (XRPD)

Powder XRD patterns were recorded on a PANalytical X Pert Pro diffractometer using Cu Kα radiation at 40 kV and 40 mA. The standard X-ray powder pattern scans were collected from ca. 2 to 40° 2θ with a 0.0080° step size and 96.06 sec counting time which resulted in a scan rate of approximately 0.5°/min. For variable temperature studies a series of rapid scans at approximately 21°/min were collected. Typical rapid scans were from 3° to 30° 2θ with a step size of 0.167° and a counting time of 64 seconds.

For the single crystal the X-ray intensity data were measured at 110(2) K on a Oxford Instruments Xcalibur3 diffractometer system equipped with a graphite monochromator and a MoKα fine-focus sealed tube (λ=0.71073 Å) operated at 2 kW power (50 kV, 40 mA). The detector was placed at a distance of 50 mm. from the crystal. 515 frames were collected with a scan width of 1.00° in ω. All frames were collected with an exposure time of 60 sec/frame. The frames were integrated with the Oxford diffraction package CrysAlis RED.

Differential Scanning Calorimetry (DSC) and Thermogravimetric Analysis (TGA)

Thermal curves were acquired using a Perkin-Elmer Series 7 DSC and TGA using Pyris software version 6.0. Solid samples of 1-11 mg were weighed into 20 μL aluminum samples pans and crimp-sealed with a pin-hole added to the top lid. The cell was purged with nitrogen and the temperature heated from 0° to 300° C. at 10° C./min. TGA samples between 1-15 mg were monitored for percent weight loss as heated from 25° to 300° C. at 10° C./min in a furnace purged with nitrogen at ca. 50 mL/min.

Thermal curves were also acquired using a Perkin-Elmer Sapphire DSC Autosampler Unit DSC and Pyris 1TGA using Pyris software version 6.0. Solid samples of 1-11 mg were weighed into 20 μL aluminum open sample pans. The cell was purged with nitrogen and the temperature heated from 0° to 355° C. at 10° C./min. TGA samples between 1-15 mg were monitored for percent weight loss as heated from 25° to 400° C. at 10° C./min in a furnace purged with nitrogen at ca. 50 mL/min.

EXAMPLES pTSA-$A_1$, pTSA-$A_2$, pTSA-$B_2$ and pTSA-$C_2$ Crystal Forms
Preparation of Compound I pTSA-$A_1$ A 344.6 mg sample of pilot plant batch Compound I-pTSA 1:1.03 (Cephalon France, Mitri Mory, France) was slurried in 100 mL (290 vol.) of methylene chloride and warmed to the boiling point and held with stirring at this temperature for 10 minutes. The slurry was suction filtered using a 5 μm membrane filter and solid washed with methylene chloride (2×10 mL). The orange solution that resulted was concentrated to about 5 mL volume. During this time the solution became cloudy when 15-20 mL of volume remained. The slurry was chilled at 2-8° C. overnight and vacuum filtered to give a yellow-orange solid that was allowed to dry at room temperature to a constant weight of 230 mg (67% yield).

Preparation of Compound I pTSA-$A_2$

A 200.7 mg sample of Compound I free base (Cephalon France, Mitri Mory, France) (0.420 mmoles) was heated with stirring in 105 mL (523 vol.) of methylene chloride to the boiling point and held at this temperature with stirring for 2-3 minutes. The cloudy, warm solution was filtered using a 5μ syringe filter into a slurry of 165.7 mg pTSA acid monohydrate (0.871 mmoles) in 20 mL of methylene chloride with stirring. The initially clear orange solution dissolved all but a few visible particles of the pTSA acid. This solution was quickly syringe filtered with a 5μ filter disk while maintaining the temperature. After filtration the solution turned cloudy and crystals were evident. The solution was concentrated to about 25 mL by warming to the boiling point with stirring and chilled overnight at 2-8° C. The slurry was vacuum filtered and solid allowed to dry about 4 hours in the hood at room temperature. The yellow-orange solid weighed 274.1 mg (79% yield).

Preparation of Compound I pTSA-$B_2$

A 206.0 mg sample of Compound I free base (0.431 mmoles) was heated with stirring in 150 mL, (728 vol.) of acetone to the boiling point and held at this temperature for 30 minutes to dissolve remaining fine particles. Additional acetone was added to make up for volume lost to evaporation. The orange-yellow solution was syringe filtered using a 5μ syringe filter into a solution of 165.3 mg of pTSA monohydrate (0.869 mmoles) in 25 mL of acetone with stirring. In a short time after filtration a solid formed and remained while the slurry was concentrated to about 25 mL and chilled at 2-8° C. overnight. The slurry was vacuum filtered and solid allowed to dry 21 hours in the oven at 50° C. The bright yellow-orange solid weighed 204.4 mg (58% yield).

Preparation of Compound I pTSA-$C_2$ 20.6 mg of Compound I-$S_1$ (0.043 mmoles) was dissolved at the boiling point in approximately 2.5 mL of n-propanol. This solution was syringe filtered while warm into a solution of 16.5 mg of p-toluenesulfonic acid monohydrate (0.086 mmoles) in 1 mL of n-propanol. An immediate color change in the solution was followed by formation of a precipitate. The mixture was concentrated to about 2 mL by heating to the boiling point and chilled overnight at 2-8° C. Suction filtration followed by air drying for 4 hours gave 22 mg (62% yield) of yellow solid.

Form Scale-Up Characterizations
XRPD

XRPD patterns were repeated at least twice to assure the reproducibility. The numbers were assigned primarily based upon XRPD pattern, and as different powder patterns were found, the letters and numbers were incrementally assigned. The number 1 was assigned to identify mono pTSA salt forms such as pTSA-$A_1$, and 2 was used for the di pTSA salt such as pTSA-$A_2$ or pTSA-$B_2$. The XRPD pattern for the single identified crystalline form of Compound I-pTSA 1:1 salt is shown in FIG. 1 (pTSA-$A_1$), and the identified crystalline forms for the Compound I-PTSA 1:2 salt are shown in FIG. 3 (pTSA-$A_2$), FIG. 5 (pTSA-$B_2$) and FIG. 7 (pTSA-$C_2$)

DSC and TGA

Figure 2:
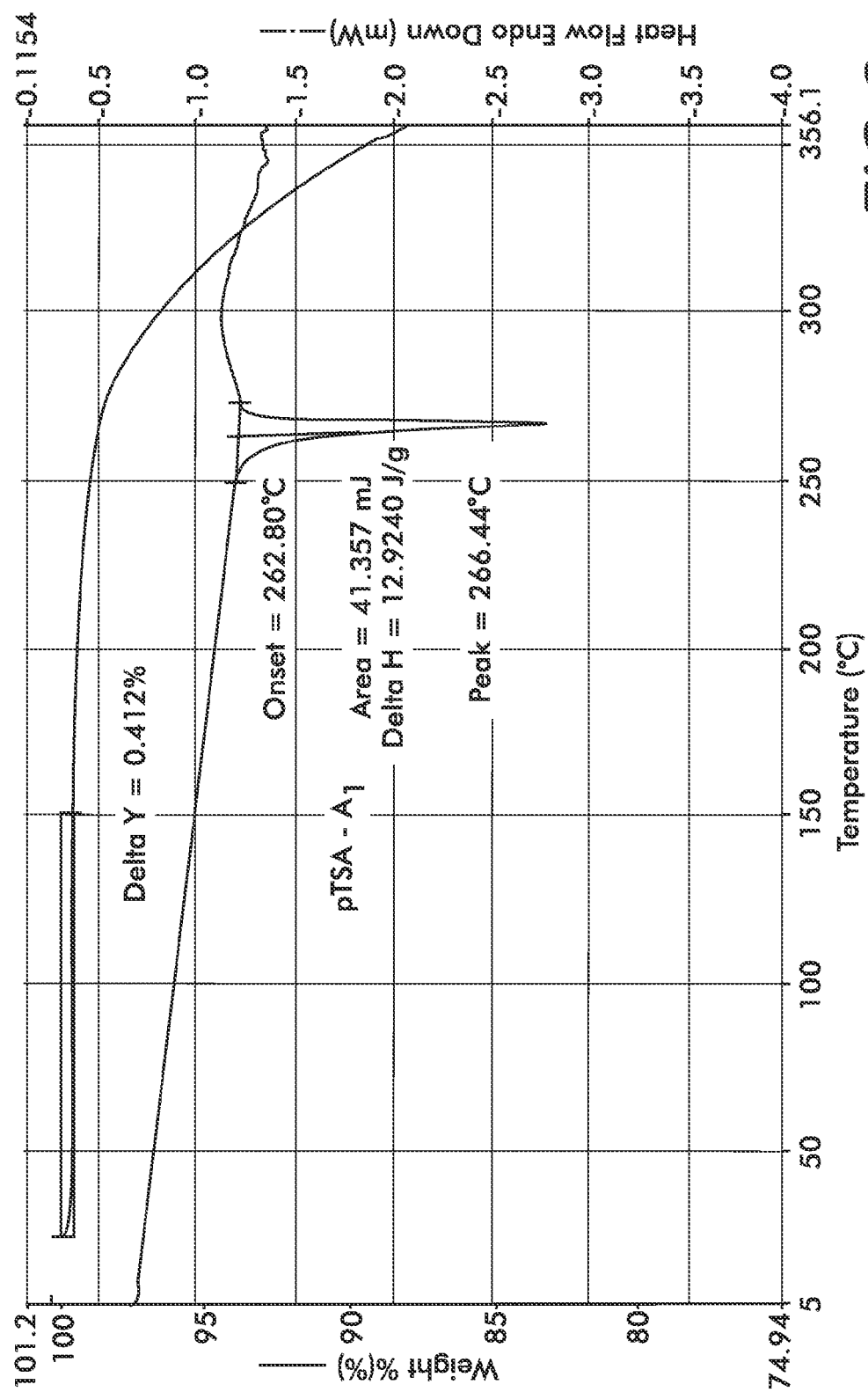
FIG. 2 is a Differential Scanning calorimetry (DSC) Thermogram and Thermo-Gravimetric Analysis (TGA) Thermogram overlay of Form pTSA-$A_1$
Figure 4:
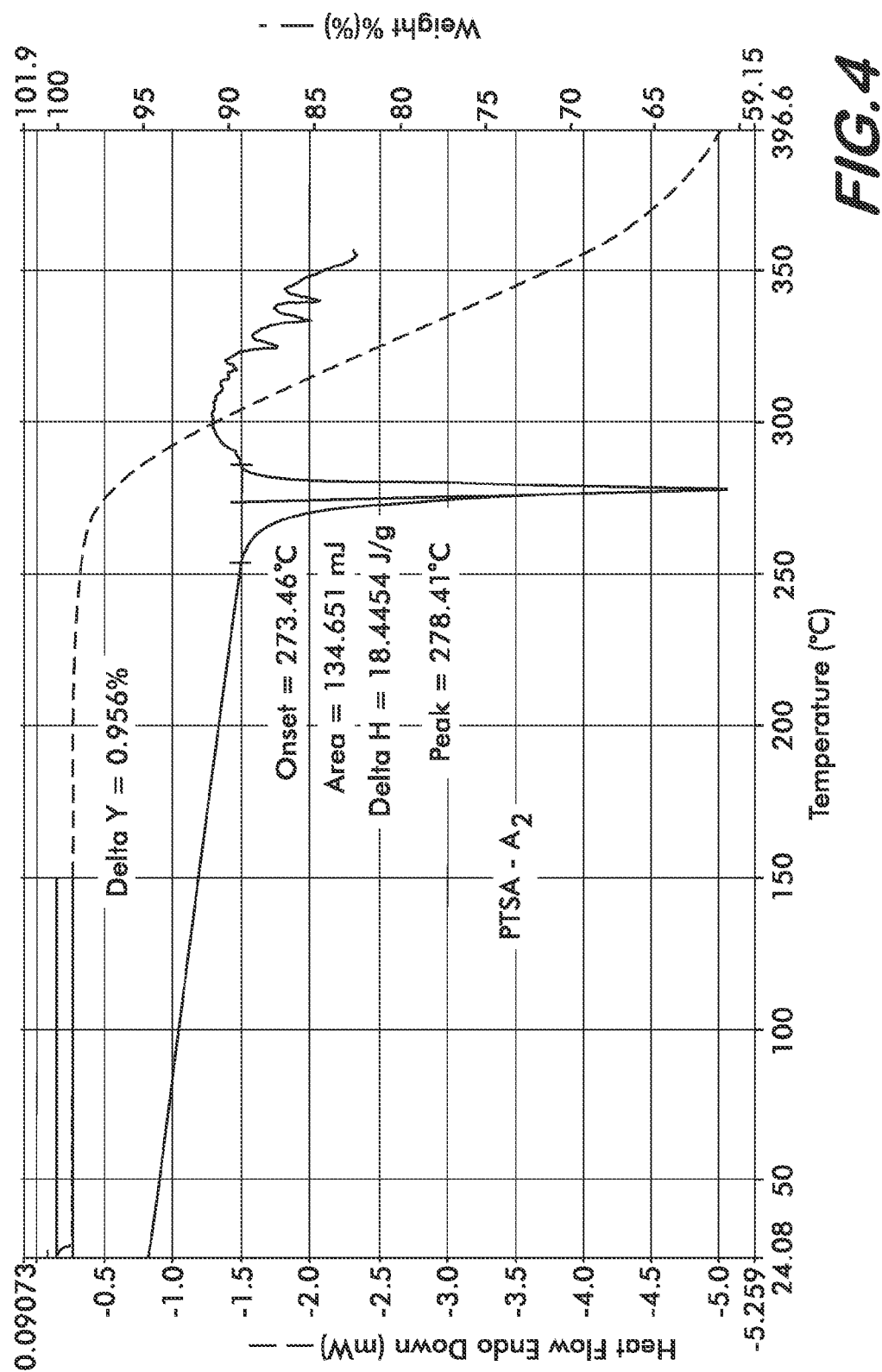
FIG. 4 is a Differential Scanning calorimetry (DSC) Thermogram and Thermo-Gravimetric Analysis (TGA) Thermogram overlay of Form pTSA-$A_2$
Figure 6:
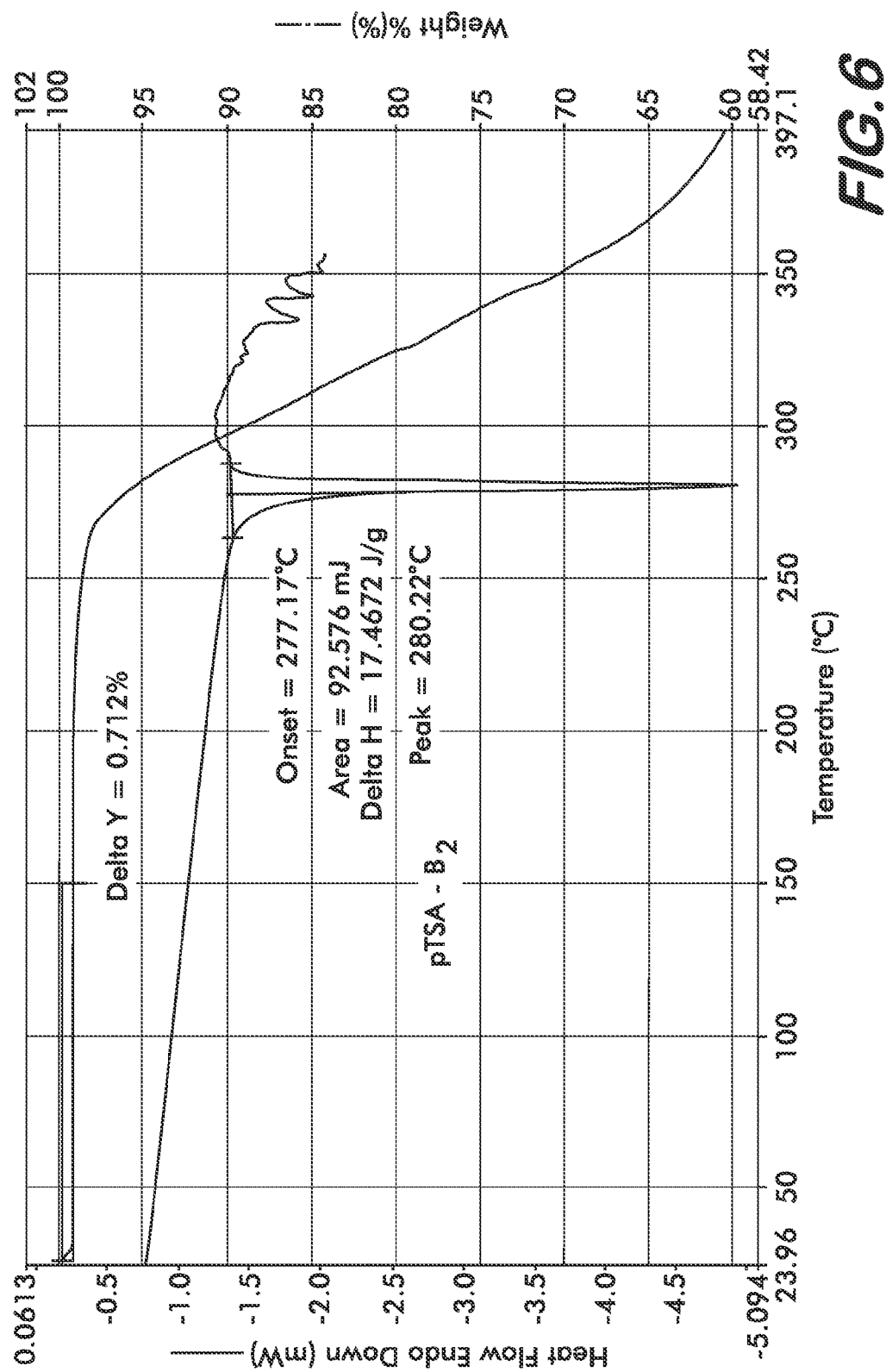
FIG. 6 is a Differential Scanning calorimetry (DSC) Thermogram and Thermo-Gravimetric Analysis (TGA) Thermogram overlay of Form pTSA-$B_2$

The DSC curves for pTSA-$A_1$, pTSA-$A_2$, pTSA-$B_2$ and pTSA-$C_2$ (FIG. 2, FIG. 4, FIG. 6, and FIG. 8, respectively) are distinguishing and can be used to identify the particular solid-state phase (Table 32 below). Form pTSA-$A_1$ shows a single peak at ca. 266.4° C. with an enthalpy of fusion ($\Delta H_{fus}$) of 12.92 J/g. The DSC curve of form pTSA-$A_2$ shows a peak at ca. 278.4° C. with an enthalpy of fusion ($\Delta H_{fus}$) of 18.45 J/g. Form pTSA-$B_2$ exhibits an endotherm at a peak temperature of ca. 280.2° C. with an enthalpy of fusion ($\Delta H_{fus}$) of 17.47 J/g. The existence of a desolvation process was discounted because no weight loss was detected by TGA (FIG. 2, FIG. 4 and FIG. 6). Form pTSA-$C_2$ melts at a peak temperature of ca. 280.4° C. with an enthalpy of fusion ($\Delta_{fus} H$) of 77.13 J/g.

TABLE 32

Onset and DSC Peak Temperatures for the Various Forms Found for Compound I-PTSA Salt 1:X(X = 1, X = 2)

| Form | Principal onset Temp./° C. | Peak Temp./° C. |
| --- | --- | --- |
| pTSA-$A_1$ | 262.8 | 266.4 |
| pTSA-$A_2$ | 273.5 | 278.4 |
| pTSA-$B_2$ | 277.2 | 280.2 |
| pTSA-$C_2$ | 277.6 | 280.4 |

$A_0$, $B_0$, $C_0$, $D_0$, $S_1$, $S_2$, $S_3$, $S_4$, $S_6$, $S_7$, $S_8$, $S_9$, $S_{10}$, $S_{13}$, $S_{14}$, $S_{15}$, $S_{16}$, $S_{17}$, $S_{18}$, $S_{19}$, and $S_{20}$ Crystal Forms Preparation of Form Compound I-$A_0$ (Conversion of Solvate Mixtures)

A slurry of Compound I (3.6 g) (Cephalon France, Mitry Mory, France) in 130.0 ml (36 Vol.) of isopropyl acetate were stirred at a ca. 400 rpm using a mechanical mixer inside a thermostated bath at 20° C. for 12 days. The solid was collected by filtration, washed with isopropyl acetate (5 ml) and dried at 50° C. overnight to afford polymorph Compound I-$A_0$ (3.31 g, 92% weight yield) as a white-pale yellow solid. This conversion may be performed in the temperature range 20-60° C.

Preparation of Form Compound I-$A_0$ (Conversion Using Acetic Acid)

The free base (89.9 g) (was completely solubilized in hot acetic acid (2853 mL (30 Vol.)) and cooled to provide the wet 2HOAc-11981 intermediate post filtration. The wet solids were slurried in isopropyl acetate (30 vol.) to convert the bulk to Form Compound I-$A_0$. The batch was filtered and dried at room temperature (77.4 g, 87% weight yield) as an orange solid.

Preparation of Form Compound I-$A_0$ (Conversion by the Solid-Solid Transition)

Compound I-$A_0$ was obtained as 20 mg Compound I was heated to 225° C. and held for 10 minutes.

Preparation of Form Compound I-$B_0$ 30.3 mg Compound I was dissolved at the boiling point in 18 mL (594 vol) of acetonitrile with magnetic stir bar. The mixture was filtered through a 0.22 μm nylon membrane filter into a warmed glass vial. The sample was concentrated by evaporating approximately to 10 mL. The residual clear yellow solution was allowed to evaporate over 72 hours. The orange solid weighed 13 mg (49% weight yield).

Preparation of Form Compound I-$C_0$ 49.6 mg Compound I was dissolved at the boiling point in 30 mL (604 vol.) of dichloroethane with magnetic stir bar. The mixture was filtered through a 0.22 μm nylon membrane filter into a warmed glass vial. The solution was cooled to RT and placed in a refrigerator (ca. 4° C.) during 18 hours and suction filtered to isolate solid. The residual clear yellow solution was allowed to evaporate over 72 hours. The sample was filtered and the crystals were transferred to weighing paper and dried to constant weight under ambient laboratory conditions. The orange solid weighed 16 mg (32% weight yield).

Preparation of Form Compound I-$D_0$ 50 mg of Compound I was weighed and dissolved at the boiling point in 10 mL methanol (200 Vol.) glass vial with magnetic stir bar. The mixture was filtered through a 0.22 μm nylon membrane filter into a warmed glass vial. The solution was cooled to RT and placed in a refrigerator (ca. 4° C.) during 18 hours and suction filtered to isolate solid. The recovery was 6 mg (3% weight yield).

Preparation of Compound I Amorphous Solid

From a solution (rapid precipitation): 279.89 mg Compound I was dissolved at the boiling point in 80 mL (294 vol.) of methanol with magnetic stir bar. The mixture was filtered through a 0.25 μm nylon membrane filter into 500 mL wet ice and 200 mL cold water with magnetic stir bar. The solution was placed in a refrigerator (ca. 4° C.) during 18 hours and suction filtered to isolate solid. The recovery was 106.8 mg (48% weight yield).

From a solution (rapid precipitation): 100 mg Compound I was dissolved at the boiling point in 25 mL (250 vol.) of ethanol denatured with magnetic stir bar. The mixture was filtered through a 0.25 μm nylon membrane filter into 500 mL wet ice and cold water with magnetic stir bar. The solution was placed in a refrigerator (ca. 4° C.) during 18 hours and suction filtered to isolate the solid. The recovery was 54 mg (54% weight yield).

From a crystalline phase (grinding): Approximately 30 mg of Compound I-$A_0$ was ground at different times ranging from 3 to 12 min in an agate mortar. Samples were removed for XRPD and thermal analysis. The grinding process was stopped every 3 minutes to scrape and remix powder cakes at the curvature end of the jars to ensure homogenous grinding.

From a liquid phase (quench cooling): The Compound I-$A_0$ was melted at a temperature approximately 360° C. above its melting point and then cooled to approximately 100° C. below the Tg at a cooling rate of 10° C./min.

Preparation of Form Compound I-$S_1$

Approximately 64.46 g of Compound I was solubilized in dichloromethane/ethanol 90/10 (3 liters) and the solvents were evaporated to dryness. The solid obtained was dried under vacuum for several days: 6 days at room temperature+ 48 h at 40° C.+24 h at 45° C. The recovery was 94%.

Preparation of Form Compound I-$S_2$ 50 mg of Compound I was stirred with heating to the boiling point in 4 mL of 1,2-dichloroethane to dissolve as much of the solid as possible. The warm solution was syringe filtered (1.2μ, nylon membrane) and 3 mL of the solution was allowed to chill overnight at 2-8° C. Suction filtration and drying of the solid recovered gave 13 mg of solid (26% recovery).

Preparation of Form Compound I-$S_3$ 50 mg of Compound I was stirred with heating to the boiling point in 2.5 mL of 6:4(v:v) N-methylpyrrolidone (NMP):water to dissolve as much of the solid as possible. The warm solution was syringe filtered (1.2μ, nylon membrane) and all of the solution was allowed to chill overnight at 2-8° C. Suction filtration and drying of the solid recovered in room air for several days gave 28 mg of solid (56% recovery).

Preparation of Form Compound I-$S_4$

A) 50 mg of Compound I was stirred with heating to the boiling point in 3 mL of chloroform to dissolve as much of the solid as possible. The warm solution was syringe filtered (1.2μ, nylon membrane) and the solution was allowed to evaporate at room temperature to give 48.4 mg of solid (97% recovery).

B) From 20° C., 50 mg of Compound I-$A_0$ in 2.5 mL was heated to an initial temperature of 80° C. at a rate of 4.8° C./min and, after 30 minutes, cooled at a slow (0.28° C./min), rate to a final temperature of 5° C. and kept at that temperature for 18 h. The crystallization experiments were carried out in glass vial (4 mL) well plates, and solid material was isolated by filtration. The solid was dried at 57° C. during 10 hours.

C) From 20° C., 50 mg of Compound I-$A_0$ in 0.3 mL were heated to an initial temperature of 80° C. at a rate of 4.8° C./min and, after 30 minutes, cooled at a slow (0.28° C./min), rate to a final temperature of 5° C. and kept at that temperature for 18 h. The crystallization experiments were carried out in glass vial (4 mL) well plates, and solid material was isolated by filtration. The solid was dried at 57° C. during 10 hours.

D) From 20° C., 50 mg of Compound I-$A_0$ in 2.5 mL were heated to an initial temperature of 80° C. at a rate of 4.8° C./min and, after 30 minutes, cooled at a fast (10° C./min), rate to a final temperature of 5° C. and kept at that temperature for 18 h. The crystallization experiments were carried out in glass vial (4 mL) well plates, and solid material was isolated by filtration. The solid was dried at 57° C. during 10 hours.

Preparation of Form Compound I-$S_6$ 50 mg of Compound I was stirred with heating to the boiling point in 4 mL of 1,2-dichloroethane to dissolve as much of the solid as possible. The warm solution was syringe filtered (1.2μ, nylon membrane) and 3 mL of the solution was allowed to chill overnight at 2-8° C. Suction filtration and drying of the solid recovered gave 13 mg of solid (26% recovery).

Preparation of Form Compound I-S$_7$ 50 mg of Compound I was stirred with heating to the boiling point in 4 mL of 1-propanol to dissolve as much of the solid as possible. The warm solution was syringe filtered (1.2μ, nylon membrane) and all of the solution was allowed to chill overnight at 2-8° C. Suction filtration and drying of the solid recovered gave 17 mg of solid (34% recovery).

Preparation of Form Compound I-S$_8$ 50 mg of Compound I was stirred with heating to the boiling point in 5 mL of 1-butanol to dissolve as much of the solid as possible. The warm solution was syringe filtered (1.2μ, nylon membrane) and all of the solution was allowed to chill overnight at 2-8° C. Suction filtration and drying of the solid recovered gave 17 mg of solid (34% recovery).

Preparation of Form Compound I-S$_9$ 50 mg of Compound I was stirred with heating to the boiling point in 5 mL of 2-propanol to dissolve as much of the solid as possible. The warm solution was syringe filtered (1.2μ, nylon membrane) and 1 mL of the solution was allowed to chill overnight at 2-8° C. Suction filtration and drying of the solid recovered gave 3.5 mg of solid (7% recovery).

Preparation of Form Compound I-S$_{10}$ 509.2 mg of Compound I was dissolved in 90 mL of tetrahydrofuran at the boiling point and the solution was syringe filtered (1.2μ, nylon membrane) and allowed to cool overnight on the laboratory bench to give very little crystalline material. The sample was chilled at 2-8° C. over night and then for a few hours at −13° C. when no further crystal formation was occurring as determined by visual inspection. The mother liquor was decanted away and the solid dried in the laboratory fume hood to give 186 mg (37% recovery) of orange-red product.

Preparation of Form Compound I-S$_{13}$ 26.4 mg of Compound I was dissolved at the boiling point in a mixture of dichloromethane (2.7 mL) and ethanol (0.3 mL). The sample was syringe filtered (0.22μ, nylon) and solution allowed to evaporate overnight to give a solid that when dried to constant weight in the fume hood gave 12.5 mg (47% recovery).

Preparation of Form Compound I-S$_{14}$ 40.6 mg of Compound I was warmed to the boiling point in 4 mL of 98:2 (v:v) tetrahydrofuran:water. The slurry was syringe filtered and the clear solution was chilled in the freezer overnight. The slurry was allowed to evaporate and the crystalline material at the bottom of the container weighed 12 mg (30% recovery).

Preparation of Form Compound I-S$_{15}$

A) 50.5 mg of Compound I was dissolved in 1 mL of NMP to give a clear solution at room temperature. 12 mL of warm toluene was added all at once to give a solution that was stored at 2-8° C. overnight to give a red-orange solid. The liquid was decanted away from the solid and solid scraped out of the container was allowed to dry to constant weight in the fume hood to give 29 mg of solid (50% recovery).

B) From 20° C., 50 mg of Compound I-A$_0$ in 2.5 mL were heated to an initial temperature of 80° C. at a rate of 4.8° C./min and, after 30 minutes, cooled at a slow (0.28° C./min) rate to a final temperature of 5° C. and kept at that temperature for 18 h. The crystallization experiments were carried out in glass vial (4 mL) well plates, and solid material was isolated by filtration. The solid was dried at 57° C. during 10 hours.

Preparation of Form Compound I-S$_{16}$ 54.9 mg of Compound I was slurried in 5 mL of 1,2-dichloroethane at the boiling point. 0.5 mL of NMP was added and the clear solution that formed was syringe filtered (5μ, nylon) and allowed to cool at room temperature over several hours where a white solid had formed. The mixture was allowed to chill in the freezer overnight. From the freezer the slurry was added to 3-1.5 mL centrifuge tubes and the pellet obtained was dried overnight at room temperature to give 14 mg of solid (26% recovery).

Preparation of Form Compound I-S$_{17}$ 51.2 mg of Compound I was dissolved in 5 mL of 70:30 (v:v) of chloroform:isopropyl acetate. The solution was cooled overnight at 2-8° C. The slurry that resulted was distributed among 3-1.5 mL centrifuge tubes. The pellet was removed to weighing paper and dried to constant weight to give 33 mg of solid (64% recovery).

Preparation of Form Compound I-S$_{18}$ 49.9 mg of Compound I was dissolved with heating in 3 mL of 1,4-dioxane. When warm, 2 mL of cyclohexane gave a turbid solution which was cooled at 2-8° C. overnight.

The slurry that resulted was distributed among 3-1.5 mL centrifuge tubes. The pellet was removed to weighing paper and allowed to dry overnight to give 31 mg of solid (62% recovery).

Preparation of Form Compound I-S$_{19}$

From 20° C., 2 g of Compound I-A$_0$ in 100 mL of dimethyl sulfoxide (DMSO) were heated to an initial temperature of 80° C. at a rate of 4.8° C./min and, after 30 minutes, cooled at a slow (0.28° C./min), rate to a final temperature of 20° C. The crystallization experiments were carried out in glass vial (4 mL) well plates, and solid material was isolated by filtration.

Preparation of Form Compound I-S$_{20}$ 1 g of Compound I-S$_{20}$ was obtaining by stirring with the Solvate S$_{19}$ in 40 ml of isopropyl acetate (40 vol.) during 15 minutes using an ultraturax homogenizer at room temperature.

Form Scale-Up Characterizations

XRPD

The X-ray diffraction measurements of each form were repeated at least two times and a complete reproducibility of the positions of the peaks (2θ) was obtained.

The XRPD diffraction pattern characteristic of Compound I-A$_0$ is shown in FIG. 9. The XRPD diffraction pattern characteristic of Compound I-B$_0$ is shown in FIG. 11. The XRPD diffraction pattern characteristic of Compound I-C$_0$ is shown in FIG. 13. The XRPD diffraction pattern characteristic of Compound I-D$_0$ is shown in FIG. 15. The XRPD diffraction patterns characteristic of Compound I solvates S$_1$-S$_4$, S$_6$-S$_{10}$, and S$_{13}$-S$_{20}$ are shown in FIGS. 17, 19, 21, 23, 25, 27, 29, 31, 33, 35, 36, 38, 40, 42, 44, 46 and 48, respectively. The XRPD diffraction pattern for the amorphous solid (AS) is shown in FIG. 50.

DSC/TGA

Onset, peak DSC and enthalpy of fusion temperatures for forms Compound I-A$_0$, B$_0$, C$_0$ and D$_0$ are shown in Table 41 below.

TABLE 41

Onset, Peak DSC and Enthalpy of Fusion Temperatures for Forms Compound I- A$_0$, B$_0$, C$_0$ and D$_0$

| Form | Principal onset Temp./ ° C. | Peak Temp./ ° C. | enthalpy of fusion ($\Delta H_{fus}$)/J/g |
|---|---|---|---|
| Compound I-A$_0$ | 329 | 333 | 86 |
| Compound I-B$_0$ | 327 | 329 | 48 |
| Compound I-C$_0$ | 329 | 331 | 85 |
| Compound I-D$_0$ | 329 | 330 | 99 |

DSC and TGA patterns for forms Compound I-$A_0$, $B_0$, $C_0$ and $D_0$ are shown in FIGS. 10, 12, 14 and 16, respectively.

DSC and/or TGA patterns for solvates $S_1$-$S_4$, $S_6$-$S_{10}$, and $S_{14}$-$S_{20}$ are shown in FIGS. 18, 20, 22, 24, 26, 28, 30, 32, 34, 37, 39, 41, 43, 45, 47 and 49, respectively.

The DSC profile of Amorphous Solid Compound I (AS) exhibits a very broad exothermic peak which is associated to a release of energy due to a crystallization process which results in the formation of polymorph Compound I-$A_0$ and the broad endothermic peak at 328° C. corresponds to its melting. No glass transition event was observed when the experiment was performed between 20° C. to 160° C. AS exhibits a glass transition temperature ($T_g$) at ca. 155° C. with the heat capacity ($\Delta Cp$) of 0.391 J/g*° C. Freshly prepared AS showed two exothermic peaks due to crystallization of the amorphous phase and its transformation a stable crystal, and melted at 328° C., which is approximately the same temperature as the melting point of the intact crystal.

Figure 51:
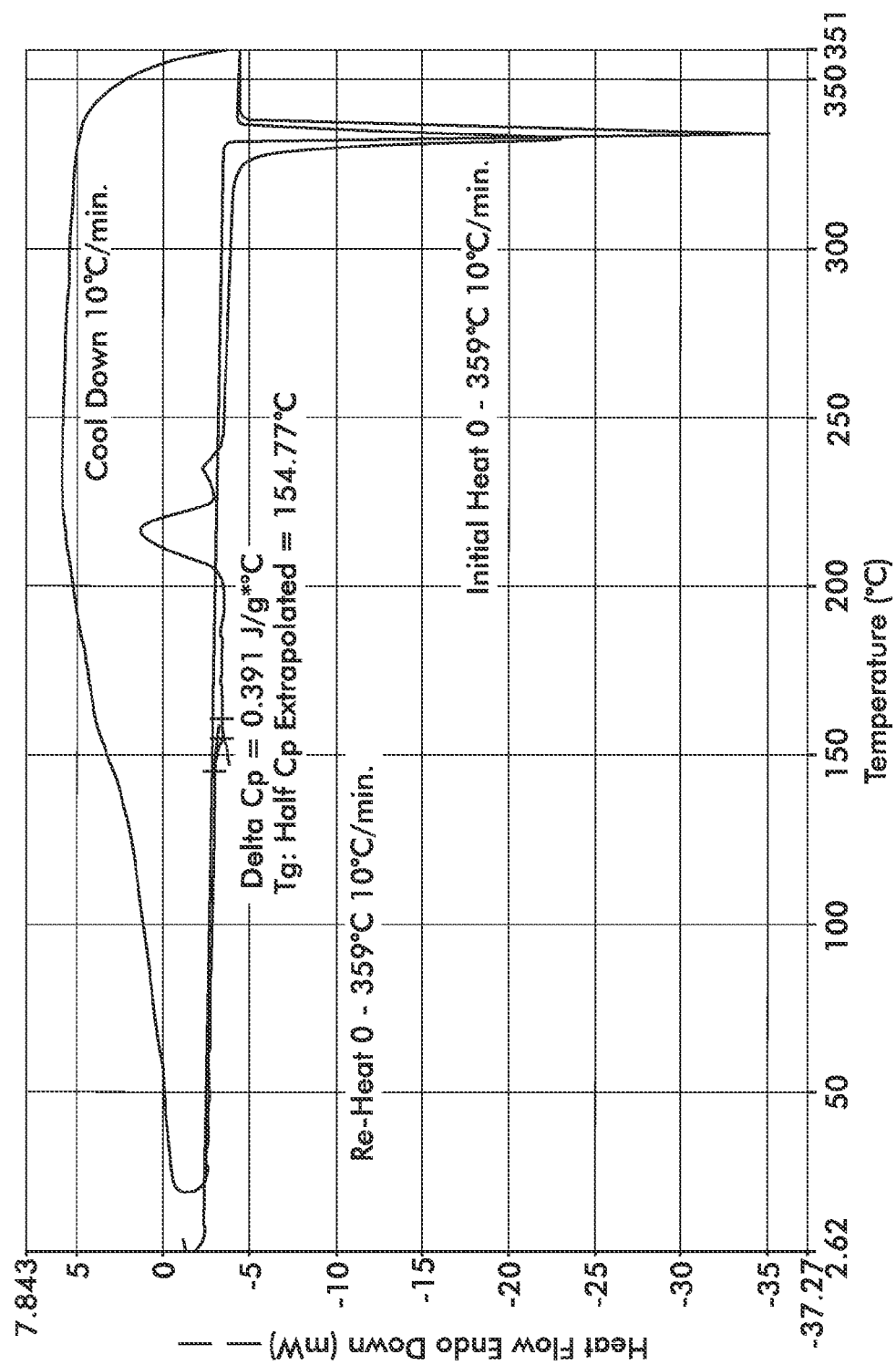
FIG. 51 is a Differential Scanning calorimetry (DSC) Thermogram and Thermo-Gravimetric Analysis (TGA) Thermogram overlay of Amorphous Solid (AS)
Figure 52:
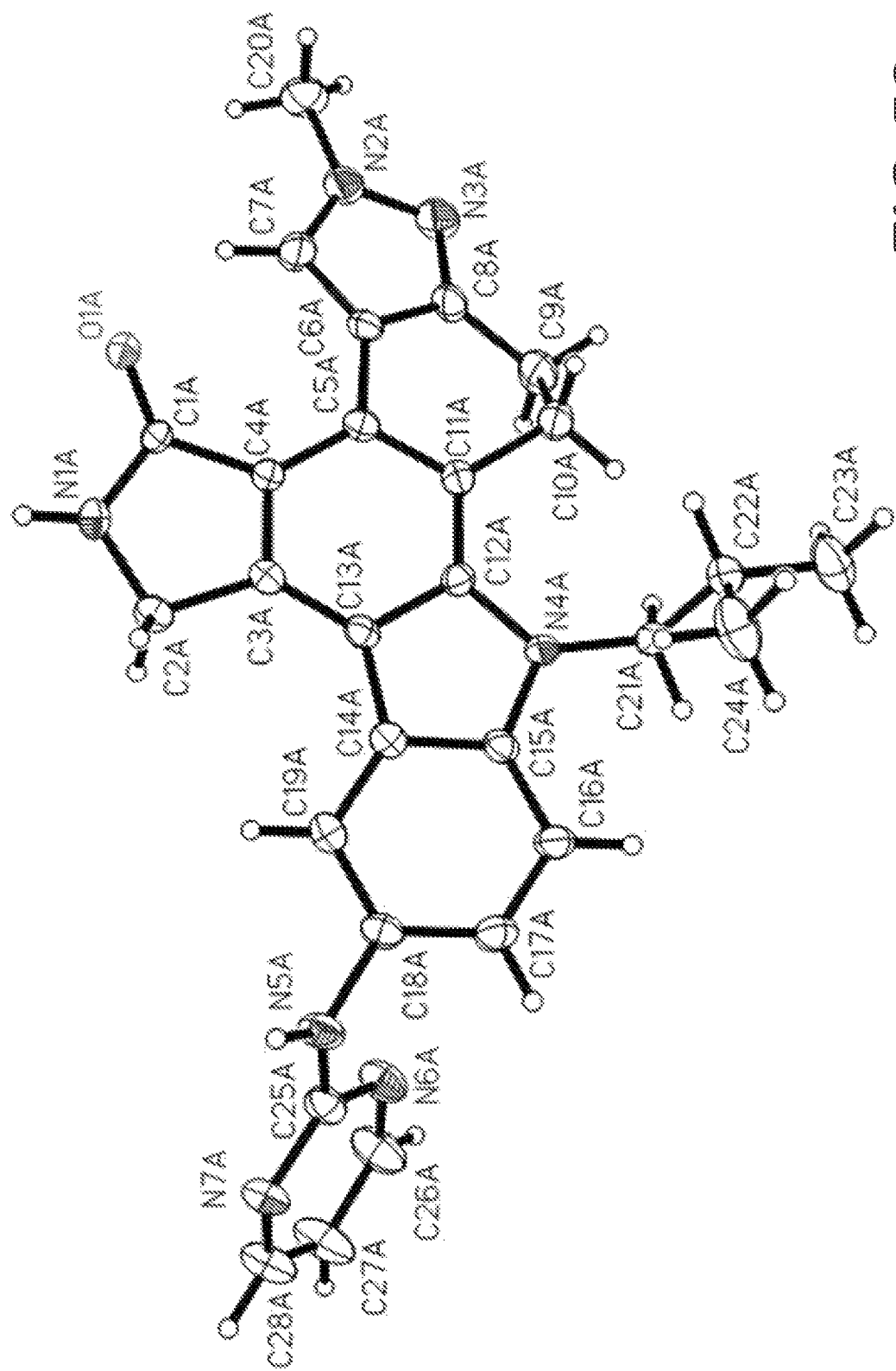
FIG. 52 depicts a view of molecule A of Compound I from the single crystal structure $A_0$, showing the numbering scheme employed

DSC and TGA patterns for Amorphous Solid Compound I (AS) are shown in FIG. 51.

Compound I Form $A_0$ Single Crystal

Figure 53:
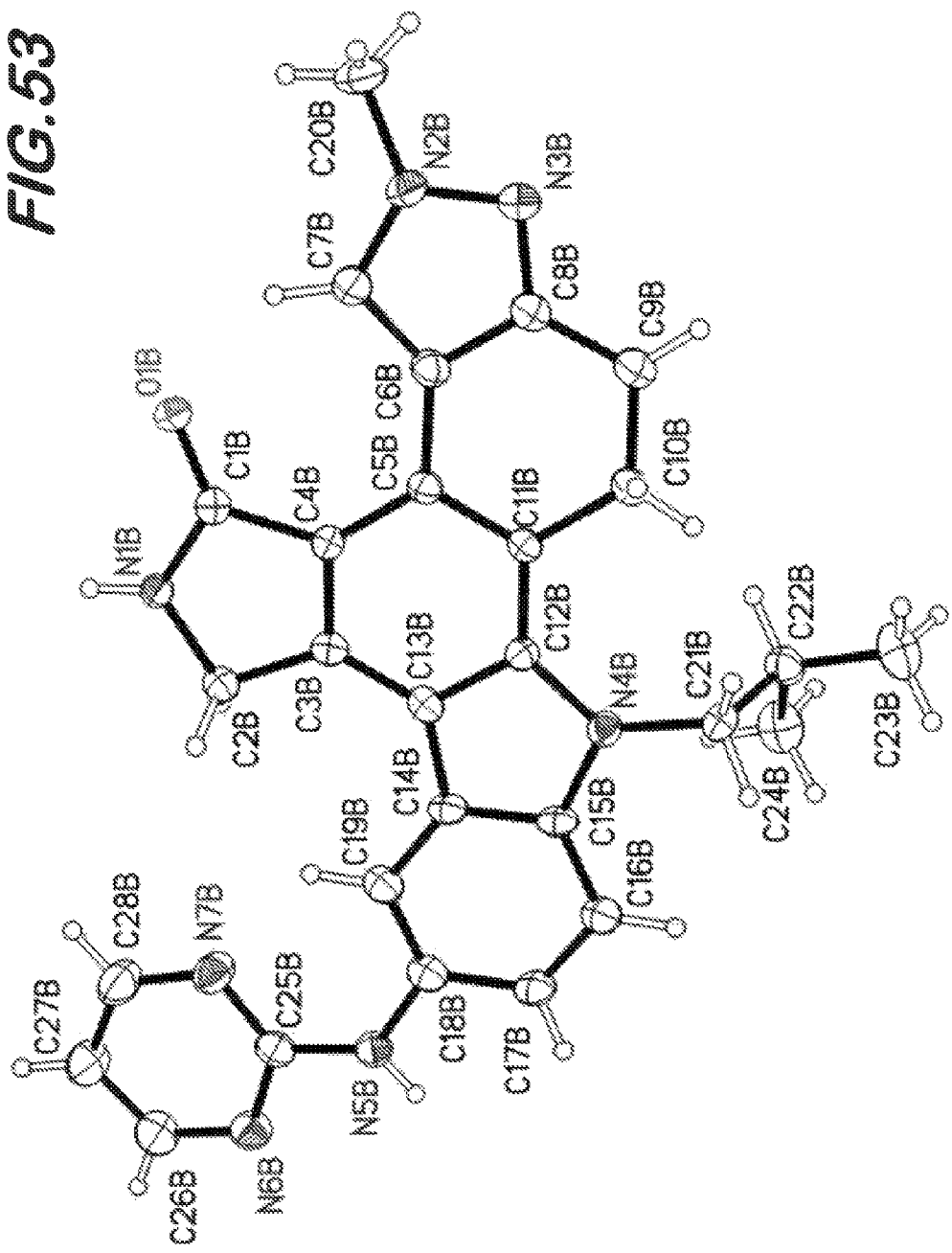
FIG. 53 depicts a view of molecule B of Compound I from the single crystal structure Form $A_0$, showing the numbering scheme employed
Figure 54:
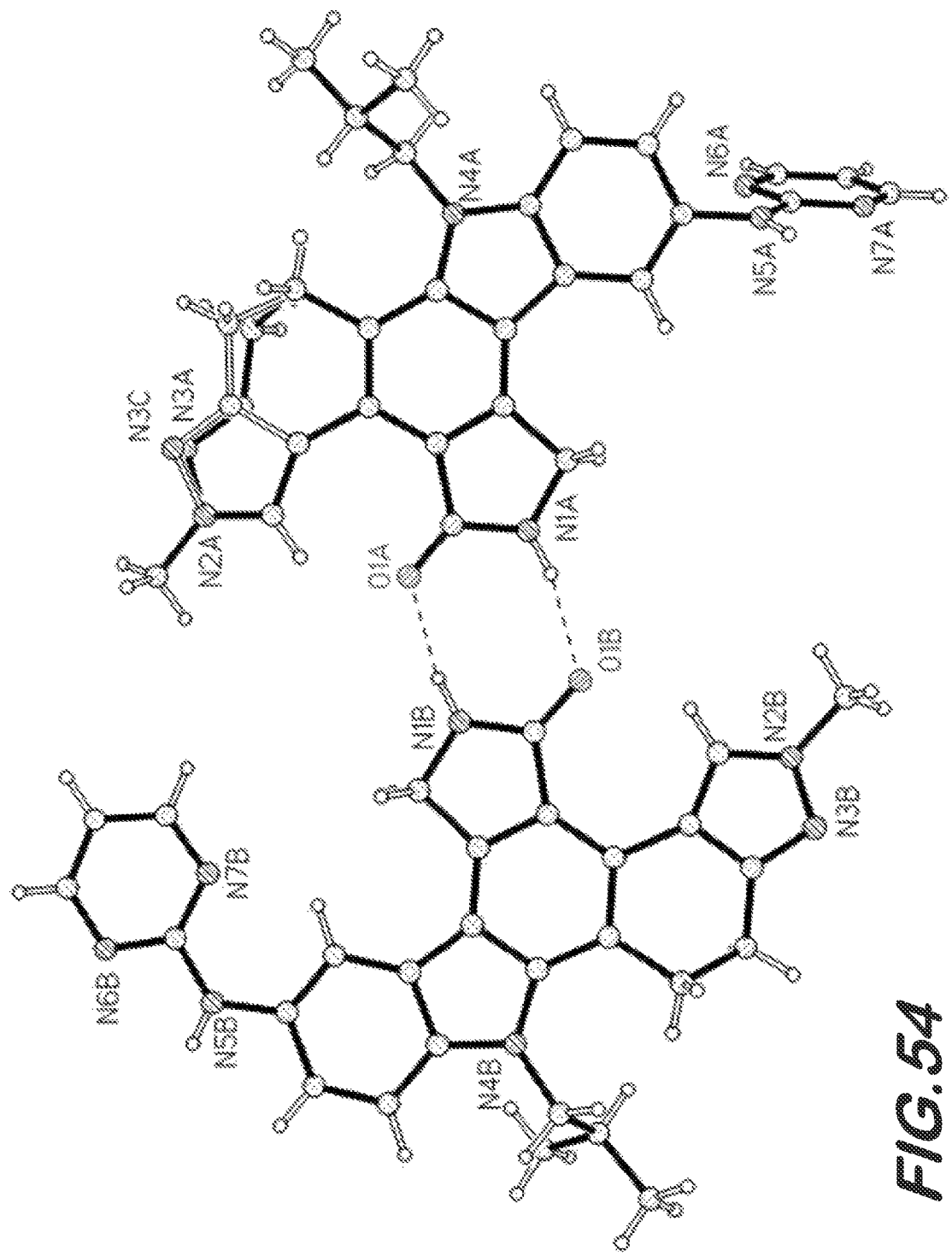
FIG. 54 depicts a view of the hydrogen bonded head-to-head dimer formed by the two independent molecules of Compound I in the single crystal structure Form $A_0$

Single crystals were obtained from PEG/Polaxamer 10 mg dose capsules which were stored for 3 months at 40° C./75% relative humidity (RH). The crystals were isolated and cleaned-up from the formulation mixture as follows: the contents of 8 capsules were dumped on a filter paper in a Buchner funnel and washed with portions of hot DI water until all the matrix material dissolved. A crystal suitable for single crystal analysis was isolated from the cleaned crystalline material. Sample and crystal data for Compound I Form $A_0$ single crystal are shown in Table 42 below:

There are two independent molecules of Compound I in the asymmetric unit. They are linked into dimers by head to head hydrogen bonds between the amide moieties in the central core of the molecule (FIG. 53). In addition, the dimers are linked by hydrogen bonding between the amino-pyrimidine moieties.

TABLE 42

Sample and crystal data for Compound I Form $A_0$ single crystal

|  | $A_0$ |
| --- | --- |
| Crystal system | monoclinic |
| Space group | Cc |
| A (Å) | 27.5221(12) |
| B (Å) | 6.9321(5) |
| C (Å) | 25.994(3) |
| α (°) | 90 |
| β (°) | 106.035(6) |
| γ (°) | 90 |
| Volume | 4766.3(6) |
| Z | 8 |

Compound I Ethanol Solvate Single Crystal

A solution of Compound I $S_1$ in ethanol was allowed to slowly evaporate to dryness under ambient conditions. The rate of evaporation was constrained by use of air tight film covers containing small holes. Crystal data for Compound I Ethanol Solvate single crystal is shown in Table 46 below:

TABLE 46

Crystal data for Compound I Ethanol Solvate single crystal

|  | Ethanol |
| --- | --- |
| Crystal system | triclinic |
| Space group | Pbar1 |

TABLE 46-continued

Crystal data for Compound I Ethanol Solvate single crystal

|  | Ethanol |
| --- | --- |
| A (Å) | 8.131(2) |
| B (Å) | 13.271(3) |
| C (Å) | 13.6390(17) |
| α (°) | 65.179(16) |
| β (°) | 86.51(2) |
| γ (°) | 83.69(2) |
| Volume | 1327.5(5) |
| Z | 2 |

Compound I NMP 1:1 Water Solvate Single Crystal

A solution of Compound I $S_1$ in NMP 1:1 water was allowed to slowly evaporate to dryness under ambient conditions. The rate of evaporation was constrained by use of air tight film covers containing small holes. Crystal data for Compound I NMP 1:1 Water Solvate single crystal is shown in Table 47 below:

TABLE 47

Crystal data for Compound I NMP 1:1 Water Solvate single crystal

|  | NMP 1:1 Water |
| --- | --- |
| Crystal system | triclinic |
| Space group | Pbar1 |
| A (Å) | 8.2359(7) |
| B (Å) | 13.5644(10) |
| C (Å) | 14.4408(11) |
| α (°) | 65.451(7) |
| β (°) | 88.496(7) |
| γ (°) | 87.326(7) |
| Volume | 1465.8(2) |
| Z | 2 |

Compound I Tetrahydrofuran Solvate Single Crystal

A solution of Compound I $S_1$ in tetrahydrofuran was allowed to slowly evaporate to dryness under ambient conditions. The rate of evaporation was constrained by use of air tight film covers containing small holes. Crystal data for Compound I Tetrahydrofuran Solvate single crystal is shown in Table 48 below:

TABLE 48

Crystal data for Compound I Tetrahydrofuran Solvate single crystal

|  | Tetrahydrofuran |
| --- | --- |
| Crystal system | orthorhombic |
| Space group | Pbcn |
| A (Å) | 17.6686(7) |
| B (Å) | 11.0367(5) |
| C (Å) | 29.2660(11) |
| α (°) | 90 |
| β (°) | 90 |
| γ (°) | 90 |
| Volume | 5707.0(4) |
| Z | 8 |

Compound 1 2-Propanol Solvate Single Crystal

A solution of Compound I $S_1$ in 2-propanol was allowed to slowly evaporate to dryness under ambient conditions. The rate of evaporation was constrained by use of air tight film covers containing small holes. Crystal data for Compound I 2-Propanol Solvate single crystal is shown in Table 49 below:

TABLE 49

Crystal data for Compound I 2-Propanol Solvate single crystal

|  | 2-propanol |
| --- | --- |
| Crystal system | triclinic |
| Space group | Pbar1 |
| A (Å) | 8.1404(18) |
| B (Å) | 13.566(3) |
| C (Å) | 13.566(3) |
| α (°) | 66.60(2) |
| β (°) | 86.583(17) |
| γ (°) | 86.583(17) |
| Volume | 1371.4(5) |
| Z | 8 |

Solubility of Various Forms of Compound I in Water and pH1, pH2 Buffers

Solubility was measured by adding 25 mg of the various forms of Compound I or an amount adequate to maintain a saturated solution in water and pH 1, pH 2 (HCl/KCl buffers). Temperature of 25° C. and a stirring rate of 300 rpm were maintained by using a HEL Crystal Scan unit (HEL, UK). Samples were withdrawn at the times indicated, filtered and analyzed by HPLC for Compound I using the method described below.

HPLC Method for Measurement of CEP11981 Content of Solubility Samples

Testing was performed on a calibrated ThermoFinnigan High Performance Liquid Chromatography (HPLC) system designated LC-0410-AD. The system comprises a P4000 pump, AS3000 autosampler, and UV2000 detector. A TCM 2000 temperature control module was used to heat the column. All standard solutions and samples were prepared in Class A glass volumetric flasks and were placed in autosampler vials. Standard weightings were done using a calibrated Mettler analytical balance. The sample preparations were centrifuged using an Eppendorf microcentrifuge. The primary chromatography data was acquired and integrated using ChromQuest software. Microsoft Office Excel 2003 was used for the calculation of results.

Instrument Parameters—MET-0002383

Column: MS C18, 150×4.6 mm ID, 3.5μ Waters, m Xterra packing

Column Temperature: 30° C.

Detector: UV/VIS @ 270 nm

Injection Volume: 25 mL

Run Time: 27 minutes

Flow Rate: 1.0 mL/min

Mobile Phase A: 10 mM Ammonium Acetate (aqueous)

Mobile Phase B: 10 mM Ammonium Acetate in sample solvent

Needle Rinse Methanol

Gradient:

| Time (min) | Mobile Phase A (%) | Mobile Phase B (%) |
| --- | --- | --- |
| 0.0 | 45 | 55 |
| 7.0 | 40 | 60 |
| 11.0 | 40 | 60 |
| 23.0 | 15 | 85 |
| 23.1 | 45 | 55 |
| 27.0 | 45 | 55 |

Solubility Results

| Form Compound I | Water mcg/mL | pH 1 Buffer mcg/mL | pH 2 Buffer mcg/mL |
| --- | --- | --- | --- |
| pTSA-A1 | <1 | 23 | 0.3 |
| pTSA-A2 | 20 | 11 | 5 |
| Form-A0 | <1 | 5 | 0.03 |
| AS | <1 | 20000 | 0.04 |

The different solubilities of the various solid state forms of Compound I can be advantageous when preparing pharmaceutical compositions. For example, selecting one or more specific solid state or crystalline forms of Compound I in combination with one or more excipients can provide a pharmaceutical composition with a particular bioavailability profile.

It is meant to be understood that peak heights (intensities) in a XRPD spectrum may vary and will be dependent on variables such as the temperature, crystal size or morphology, sample preparation, or sample height in the analysis well of the PANalytical X Pert Pro diffractometer or Oxford Instruments Xcalibur3 diffractometer system.

It is also meant to be understood that peak positions may vary when measured with different radiation sources. For example, Cu—Kα$_1$, Mo—Kα, Co—Kα and Fe—Kα radiation, having wavelengths of 1.54060 Å, 0.7107 Å, 1.7902 Å and 1.9373 Å, respectively, may provide peak positions that differ from those measured with Cu—Kα radiation. The wavelength of Cu—Kα radiation is λ=1.54056 Å.

It is further meant to be understood that the term "±0.2 degrees 2-theta" following a series of peak positions means that all of the peaks of the group which it follows are reported in terms of angular positions with a variability of ±0.2 degrees 2-theta. For example, "6.81, 8.52, 9.73, 12.04 and/or 13.25±0.2 degrees 2-theta" means "6.81±0.2 degrees 2-theta, 8.52±0.2 degrees 2-theta, 9.73±0.2 degrees 2-theta, 12.04±0.2 degrees 2-theta and/or 13.25±0.2 degrees 2-theta".

As those skilled in the art will appreciate, numerous modifications and variations of the present invention are possible in view of the above teachings. It is therefore understood that within the scope of the appended claims, the invention can be practiced otherwise than as specifically described herein, and the scope of the invention is intended to encompass all such variations.

We claim:

1. A crystalline form of a Compound I-para-toluenesulfonic acid (pTSA) salt (1:1) where Compound I is

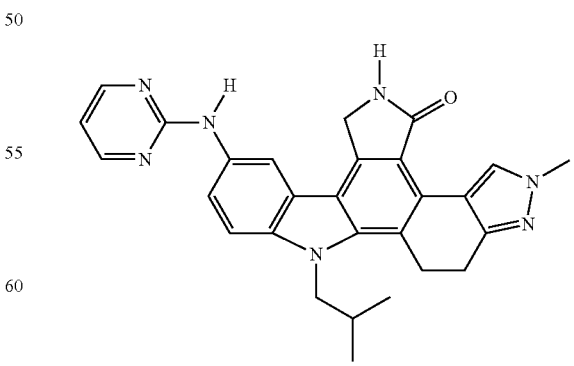

(11-isobutyl-2-methyl-8-(2-pyrimidinylamino)-2,5,6,11,12,13-hexahydro-4H-indazolo[5,4-a]pyrrolo[3,4-c]carbazol-4-one)

having an X-ray powder diffraction pattern comprising one or more of the following peaks: 5.37±0.2 degrees 2-theta, 6.79±0.2 degrees 2-theta, 13.64±0.2 degrees 2-theta, 22.58±0.2 degrees 2-theta and/or 25.54±0.2 degrees 2-theta, when measured using Cu—Kα radiation (λ=1.54056 Å).

2. A crystalline form according to claim 1 having an X-ray powder diffraction pattern comprising a peak at 5.37±0.2 degrees 2-theta and one or more of the following peaks: 6.79±0.2 degrees 2-theta, 13.64±0.2 degrees 2-theta, 22.58±0.2 degrees 2-theta and/or 25.54±0.2 degrees 2-theta, when measured using Cu—Kα radiation (λ=1.54056 Å).

3. A crystalline form according to claim 2 having an X-ray powder diffraction pattern comprising peaks at 5.37±0.2 degrees 2-theta and 6.79±0.2 degrees 2-theta and one or more of the following peaks: 13.64±0.2 degrees 2-theta, 22.58±0.2 degrees 2-theta and/or 25.54±0.2 degrees 2-theta, when measured using Cu—Kα radiation (λ=1.54056 Å).

4. A crystalline form according to claim 3 having an X-ray powder diffraction pattern comprising peaks at 5.37±0.2 degrees 2-theta, 6.79±0.2 degrees 2-theta, and 25.54±0.2 degrees 2-theta and one or more of the following peaks: 13.64±0.2 degrees 2-theta, and/or 22.58±0.2 degrees 2-theta, when measured using Cu—Kα radiation (λ=1.54056 Å).

5. A crystalline form according to claim 4 having an X-ray powder diffraction pattern comprising peaks at 5.37±0.2 degrees 2-theta, 6.79±0.2 degrees 2-theta, 13.64±0.2 degrees 2-theta, 22.58±0.2 degrees 2-theta and 25.54±0.2 degrees 2-theta, when measured using Cu—Kα radiation (λ=1.54056 Å).

6. A crystalline form of a Compound I-para-toluene-sulfonic acid (pTSA) salt (1:2) where Compound I is

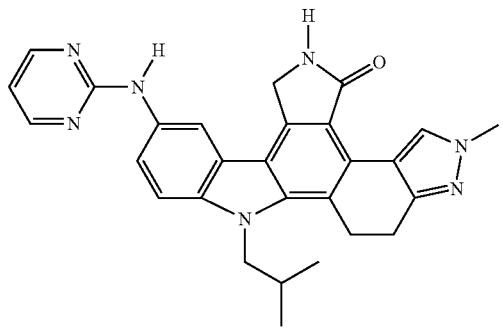 [SMILES: CC(C)Cn1c2ccc(Nc3ncccn3)cc2c2c3c(c4c(c21)CCc1nn(C)cc1-4)C(=O)NC3]

(11-isobutyl-2-methyl-8-(2-pyrimidinylamino)-2,5,6,11,12,13-hexahydro-4H-indazolo[5,4-a]pyrrolo[3,4-c]carbazol-4-one)

having an X-ray powder diffraction pattern comprising one or more of the following peaks: 5.63±0.2 degrees 2-theta, 8.48±0.2 degrees 2-theta, 12.46±0.2 degrees 2-theta, 18.21±0.2 degrees 2-theta and/or 23.95±0.2 degrees 2-theta, when measured using Cu—Kα radiation (λ=1.54056 Å).

7. A crystalline form according to claim 6 having an X-ray powder diffraction pattern comprising a peak at 5.63±0.2 degrees 2-theta and one or more of the following peaks: 8.48±0.2 degrees 2-theta, 12.46±0.2 degrees 2-theta, 18.21±0.2 degrees 2-theta and/or 23.95±0.2 degrees 2-theta, when measured using Cu—Kα radiation (λ=1.54056 Å).

8. A crystalline form according to claim 7 having an X-ray powder diffraction pattern comprising peaks at 5.63±0.2 degrees 2-theta and 8.48±0.2 degrees 2-theta, and one or more of the following peaks: 12.46±0.2 degrees 2-theta, 18.21±0.2 degrees 2-theta and/or 23.95±0.2 degrees 2-theta, when measured using Cu—Kα radiation (λ=1.54056 Å).

9. A crystalline form according to claim 8 having an X-ray powder diffraction pattern comprising peaks at 5.63±0.2 degrees 2-theta, 8.48±0.2 degrees 2-theta, and 12.46±0.2 degrees 2-theta and one or more of the following peaks: 18.21±0.2 degrees 2-theta and/or 23.95±0.2 degrees 2-theta, when measured using Cu—Kα radiation (λ=1.54056 Å).

10. A crystalline form according to claim 9 having an X-ray powder diffraction pattern comprising peaks at 5.63±0.2 degrees 2-theta, 8.48±0.2 degrees 2-theta, 12.46±0.2 degrees 2-theta, 18.21±0.2 degrees 2-theta, and 23.95±0.2 degrees 2-theta, when measured using Cu—Kα radiation (λ=1.54056 Å).

11. A crystalline form of Compound I where Compound I is

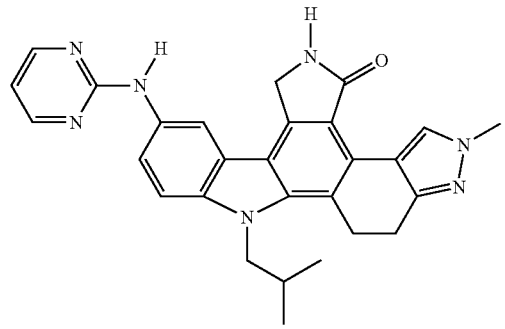 [SMILES: CC(C)Cn1c2ccc(Nc3ncccn3)cc2c2c3c(c4c(c21)CCc1nn(C)cc1-4)C(=O)NC3]

(11-isobutyl-2-methyl-8-(2-pyrimidinylamino)-2,5,6,11,12,13-hexahydro-4H-indazolo[5,4-a]pyrrolo[3,4-c]carbazol-4-one)

having an X-ray powder diffraction pattern comprising one or more of the following peaks: 6.70±0.2 degrees 2-theta, 7.00±0.2 degrees 2-theta, 8.19±0.2 degrees 2-theta, 13.69±0.2 degrees 2-theta, and/or 24.27±0.2 degrees 2-theta when measured using Cu—Kα radiation (λ=1.54056 Å).

12. A crystalline form according to claim 11 having an X-ray powder diffraction pattern comprising a peak at 6.70±0.2 degrees 2-theta and one or more of the following peaks: 7.00±0.2 degrees 2-theta, 8.19±0.2 degrees 2-theta, 13.69±0.2 degrees 2-theta, and/or 24.27±0.2 degrees 2-theta when measured using Cu—Kα radiation (λ=1.54056 Å).

13. A crystalline form according to claim 12 having an X-ray powder diffraction pattern comprising peaks at 6.70±0.2 degrees 2-theta and 24.27±0.2 degrees 2-theta and one or more of the following peaks: 7.00±0.2 degrees 2-theta, 8.19±0.2 degrees 2-theta, and/or 13.69±0.2 degrees 2-theta, when measured using Cu—Kα radiation (λ=1.54056 Å).

14. A crystalline form according to claim 13 having an X-ray powder diffraction pattern comprising peaks at 6.70±0.2 degrees 2-theta, 24.27±0.2 degrees 2-theta, and 13.69±0.2 degrees 2-theta, and one or more of the following peaks: 7.00±0.2 degrees 2-theta, and/or 8.19±0.2 degrees 2-theta, when measured using Cu—Kα radiation (λ=1.54056 Å).

15. A crystalline form according to claim 14 having an X-ray powder diffraction pattern comprising peaks at 6.70±0.2 degrees 2-theta, 7.00±0.2 degrees 2-theta, 8.19±0.2 degrees 2-theta, 13.69±0.2 degrees 2-theta, and 24.27±0.2 degrees 2-theta when measured using Cu—Kα radiation (λ=1.54056 Å).

16. A composition comprising a crystalline para-toluenesulfonic acid (pTSA) salt of Compound I where Compound I is

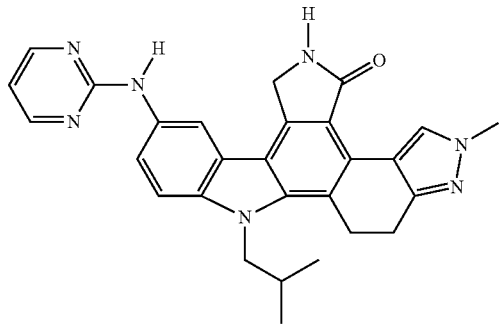 [SMILES: CC(C)Cn1c2ccc(Nc3ncccn3)cc2c2c3c(c4c(c21)CCc1nn(C)cc1-4)C(=O)NC3]

(11-isobutyl-2-methyl-8-(2-pyrimidinylamino)-2,5,6,11,12,13-hexahydro-4H-indazolo[5,4-a]pyrrolo[3,4-c]carbazol-4-one
and at least one pharmaceutically acceptable excipient.

17. A composition according to claim 16 comprising a 1:1 pTSA salt of Compound I having an X-ray powder diffraction pattern comprising one or more of the following peaks: 5.37±0.2 degrees 2-theta, 6.79±0.2 degrees 2-theta, 13.64±0.2 degrees 2-theta, 22.58±0.2 degrees 2-theta and/or 25.54±0.2 degrees 2-theta.

18. A composition according to claim 16 comprising a 1:2 pTSA salt of Compound I having an X-ray powder diffraction pattern comprising one or more of the following peaks: 5.63±0.2 degrees 2-theta, 8.48±0.2 degrees 2-theta, 12.46±0.2 degrees 2-theta, 18.21±0.2 degrees 2-theta and/or 23.95±0.2 degrees 2-theta.

19. A composition comprising crystalline Compound I having an X-ray powder diffraction pattern comprising one or more of the following peaks: 6.70±0.2 degrees 2-theta, 7.00±0.2 degrees 2-theta, 8.19±0.2 degrees 2-theta, 13.69±0.2 degrees 2-theta, and/or 24.27±0.2 degrees 2-theta and at least one pharmaceutically acceptable excipient.

20. A composition according to claim 16 comprising one or more crystalline para-toluenesulfonic acid (pTSA) salts of Compound I.

21. A composition according to claim 16 further comprising an amorphous form of Compound I.

22. A method of treating pathologic angiogenesis comprising administering to a patient in need thereof a therapeutically effective amount of a crystalline para-toluenesulfonic acid (pTSA) salt of Compound I where Compound I is

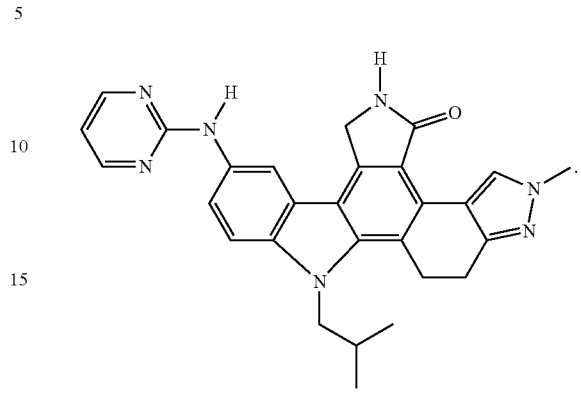

23. A method of treating solid tumors comprising administering to a patient in need thereof a therapeutically effective amount of a crystalline para-toluenesulfonic acid (pTSA) salt of Compound I where Compound I is

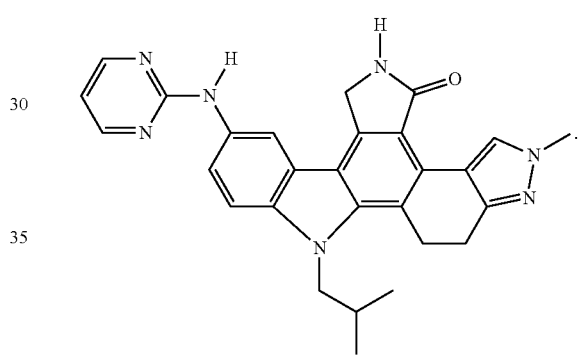

24. A method according to claim 22 comprising the administration of the crystalline salt of claim 1.

25. A method according to claim 23 comprising the administration of the crystalline salt of claim 1.

* * * * *